US008257259B2

(12) United States Patent
Brauker et al.

(10) Patent No.: US 8,257,259 B2
(45) **Date of Patent: *Sep. 4, 2012**

(54) SIGNAL PROCESSING FOR CONTINUOUS ANALYTE SENSOR

(75) Inventors: James H. Brauker, Cement City, MI (US); Victoria E. Carr-Brendel, San Diego, CA (US); Paul V. Goode, Cherry Hill, NJ (US); Apurv Ullas Kamath, San Diego, CA (US); James Patrick Thrower, Oakland, NJ (US); Ben Xavier, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 843 days.

This patent is subject to a terminal disclaimer.

(21) Appl. No.: 12/252,952

(22) Filed: Oct. 16, 2008

(65) Prior Publication Data

US 2009/0043541 A1 Feb. 12, 2009

Related U.S. Application Data

(63) Continuation of application No. 11/007,920, filed on Dec. 8, 2004.

(60) Provisional application No. 60/528,382, filed on Dec. 9, 2003, provisional application No. 60/587,787, filed on Jul. 13, 2004, provisional application No. 60/614,683, filed on Sep. 30, 2004.

(51) Int. Cl.
*A61B 5/00* (2006.01)

(52) U.S. Cl. ........................................ 600/365; 600/347

(58) Field of Classification Search .................. 600/309, 600/345–366

See application file for complete search history.

(56) References Cited

U.S. PATENT DOCUMENTS

| | | | |
|---|---|---|---|
| 3,210,578 | A | 10/1965 | Sherer |
| 3,219,533 | A | 11/1965 | Mullins |
| 3,775,182 | A | 11/1973 | Patton et al. |
| 3,780,727 | A | 12/1973 | King |
| 3,898,984 | A | 8/1975 | Mandel et al. |
| 3,929,971 | A | 12/1975 | Roy |

(Continued)

FOREIGN PATENT DOCUMENTS

| | | |
|---|---|---|
| CA | 2127172 | 7/1998 |

(Continued)

OTHER PUBLICATIONS

Diabetes Educational Video Game Recognized by Software Publishers Association, Press Release, Novo Nordisk, Mar. 14, 1994.

(Continued)

*Primary Examiner* — Navin Natnithithadha

(74) *Attorney, Agent, or Firm* — Knobbe Martens Olson & Bear LLP

(57) ABSTRACT

Systems and methods for dynamically and intelligently estimating analyte data from a continuous analyte sensor, including receiving a data stream, selecting one of a plurality of algorithms, and employing the selected algorithm to estimate analyte values. Additional data processing includes evaluating the selected estimative algorithms, analyzing a variation of the estimated analyte values based on statistical, clinical, or physiological parameters, comparing the estimated analyte values with corresponding measure analyte values, and providing output to a user. Estimation can be used to compensate for time lag, match sensor data with corresponding reference data, warn of upcoming clinical risk, replace erroneous sensor data signals, and provide more timely analyte information encourage proactive behavior and preempt clinical risk.

24 Claims, 29 Drawing Sheets

U.S. PATENT DOCUMENTS

| | | | |
|---|---|---|---|
| 3,943,918 | A | 3/1976 | Lewis |
| 3,964,974 | A | 6/1976 | Banauch et al. |
| 3,979,274 | A | 9/1976 | Newman |
| 4,024,312 | A | 5/1977 | Korpman |
| 4,040,908 | A | 8/1977 | Clark, Jr. |
| 4,073,713 | A | 2/1978 | Newman |
| 4,076,656 | A | 2/1978 | White et al. |
| 4,197,840 | A | 4/1980 | Beck et al. |
| 4,215,703 | A | 8/1980 | Willson |
| 4,240,889 | A | 12/1980 | Yoda et al. |
| 4,253,469 | A | 3/1981 | Aslan |
| 4,255,500 | A | 3/1981 | Hooke |
| 4,259,540 | A | 3/1981 | Sabia |
| 4,374,013 | A | 2/1983 | Enfors |
| 4,388,166 | A | 6/1983 | Suzuki et al. |
| 4,403,984 | A | 9/1983 | Ash et al. |
| 4,415,666 | A | 11/1983 | D'Orazio et al. |
| 4,431,004 | A | 2/1984 | Bessman et al. |
| 4,436,094 | A | 3/1984 | Cerami |
| 4,454,295 | A | 6/1984 | Wittmann et al. |
| 4,494,950 | A | 1/1985 | Fischell |
| 4,506,680 | A | 3/1985 | Stokes |
| RE31,916 | E | 6/1985 | Oswin et al. |
| 4,554,927 | A | 11/1985 | Fussell |
| 4,577,642 | A | 3/1986 | Stokes |
| RE32,361 | E | 2/1987 | Duggan |
| 4,655,880 | A | 4/1987 | Liu |
| 4,663,824 | A | 5/1987 | Kenmochi |
| 4,671,288 | A | 6/1987 | Gough |
| 4,680,268 | A | 7/1987 | Clark, Jr. |
| 4,685,903 | A | 8/1987 | Cable et al. |
| 4,703,756 | A | 11/1987 | Gough et al. |
| 4,711,251 | A | 12/1987 | Stokes |
| 4,721,677 | A | 1/1988 | Clark |
| 4,731,726 | A | 3/1988 | Allen |
| 4,750,496 | A | 6/1988 | Reinhart et al. |
| 4,753,652 | A | 6/1988 | Langer et al. |
| 4,757,022 | A | 7/1988 | Shults et al. |
| 4,759,828 | A | 7/1988 | Young et al. |
| 4,781,798 | A | 11/1988 | Gough |
| 4,787,398 | A | 11/1988 | Garcia et al. |
| 4,805,625 | A | 2/1989 | Wyler |
| 4,810,470 | A | 3/1989 | Burkhardt et al. |
| 4,849,458 | A | 7/1989 | Reed et al. |
| 4,852,573 | A | 8/1989 | Kennedy |
| 4,858,615 | A | 8/1989 | Meinema |
| 4,871,440 | A | 10/1989 | Nagata et al. |
| 4,883,057 | A | 11/1989 | Broderick |
| 4,889,744 | A | 12/1989 | Quaid |
| 4,890,620 | A | 1/1990 | Gough |
| 4,890,621 | A | 1/1990 | Hakky |
| 4,902,294 | A | 2/1990 | Gosserez |
| 4,907,857 | A | 3/1990 | Giuliani et al. |
| 4,919,141 | A | 4/1990 | Zier et al. |
| 4,927,407 | A | 5/1990 | Dorman |
| 4,927,516 | A | 5/1990 | Yamaguchi et al. |
| 4,944,299 | A | 7/1990 | Silvian |
| 4,953,552 | A | 9/1990 | DeMarzo |
| 4,974,592 | A | 12/1990 | Branco |
| 4,975,636 | A | 12/1990 | Desautels |
| 4,984,929 | A | 1/1991 | Rock et al. |
| 4,986,671 | A | 1/1991 | Sun et al. |
| 4,988,341 | A | 1/1991 | Columbus et al. |
| 4,994,167 | A | 2/1991 | Shults et al. |
| 5,002,572 | A | 3/1991 | Picha |
| 5,007,929 | A | 4/1991 | Quaid |
| 5,030,333 | A | 7/1991 | Clark, Jr. |
| 5,034,112 | A | 7/1991 | Murase et al. |
| 5,050,612 | A | 9/1991 | Matsumura |
| 5,059,654 | A | 10/1991 | Hou et al. |
| 5,067,491 | A | 11/1991 | Taylor, II et al. |
| 5,068,536 | A | 11/1991 | Rosenthal |
| 5,077,476 | A | 12/1991 | Rosenthal |
| 5,097,834 | A | 3/1992 | Skrabal |
| 5,101,814 | A | 4/1992 | Palti |
| 5,108,819 | A | 4/1992 | Heller et al. |
| 5,137,028 | A | 8/1992 | Nishimura |
| 5,140,985 | A | 8/1992 | Schroeder et al. |
| 5,160,418 | A | 11/1992 | Mullen |
| 5,165,407 | A | 11/1992 | Wilson et al. |
| 5,190,041 | A | 3/1993 | Palti |
| 5,198,771 | A | 3/1993 | Fidler et al. |
| 5,208,147 | A | 5/1993 | Kagenow et al. |
| 5,235,003 | A | 8/1993 | Ward et al. |
| 5,243,696 | A | 9/1993 | Carr et al. |
| 5,243,983 | A | 9/1993 | Tarr et al. |
| 5,264,104 | A | 11/1993 | Gregg et al. |
| 5,266,179 | A | 11/1993 | Nankai et al. |
| 5,269,891 | A | 12/1993 | Colin |
| 5,271,736 | A | 12/1993 | Picha |
| 5,282,848 | A | 2/1994 | Schmitt |
| 5,285,513 | A | 2/1994 | Kaufman et al. |
| 5,287,753 | A | 2/1994 | Routh et al. |
| 5,299,571 | A | 4/1994 | Mastrototaro |
| 5,304,468 | A | 4/1994 | Phillips et al. |
| 5,307,263 | A | 4/1994 | Brown |
| 5,310,469 | A | 5/1994 | Cunningham et al. |
| 5,312,361 | A | 5/1994 | Zadini et al. |
| 5,314,471 | A | 5/1994 | Brauker et al. |
| 5,316,008 | A | 5/1994 | Suga et al. |
| 5,324,322 | A | 6/1994 | Grill et al. |
| 5,326,356 | A | 7/1994 | Della Valle et al. |
| 5,330,521 | A | 7/1994 | Cohen |
| 5,330,634 | A | 7/1994 | Wong et al. |
| 5,331,555 | A | 7/1994 | Hashimoto et al. |
| 5,337,747 | A | 8/1994 | Neftel |
| 5,342,409 | A | 8/1994 | Mullett |
| 5,343,869 | A | 9/1994 | Pross et al. |
| 5,348,788 | A | 9/1994 | White |
| 5,352,351 | A | 10/1994 | White et al. |
| 5,356,786 | A | 10/1994 | Heller et al. |
| 5,368,224 | A | 11/1994 | Richardson et al. |
| 5,372,133 | A | 12/1994 | Hogen Esch |
| 5,376,070 | A | 12/1994 | Purvis et al. |
| 5,380,536 | A | 1/1995 | Hubbell et al. |
| 5,384,028 | A | 1/1995 | Ito |
| 5,390,671 | A | 2/1995 | Lord et al. |
| 5,391,250 | A | 2/1995 | Cheney, II et al. |
| 5,397,848 | A | 3/1995 | Yang et al. |
| 5,405,510 | A | 4/1995 | Betts et al. |
| 5,411,647 | A | 5/1995 | Johnson et al. |
| 5,411,866 | A | 5/1995 | Luong |
| 5,429,735 | A | 7/1995 | Johnson et al. |
| 5,431,160 | A | 7/1995 | Wilkins |
| 5,434,412 | A | 7/1995 | Sodickson et al. |
| 5,448,992 | A | 9/1995 | Kuperschmidt |
| 5,453,278 | A | 9/1995 | Chan et al. |
| 5,462,051 | A | 10/1995 | Oka et al. |
| 5,462,064 | A | 10/1995 | D'Angelo et al. |
| 5,469,846 | A | 11/1995 | Khan |
| 5,474,552 | A | 12/1995 | Palti |
| 5,484,404 | A | 1/1996 | Schulman et al. |
| 5,491,474 | A | 2/1996 | Suni et al. |
| 5,494,562 | A | 2/1996 | Maley et al. |
| 5,496,453 | A | 3/1996 | Uenoyama et al. |
| 5,497,772 | A | 3/1996 | Schulman et al. |
| 5,502,396 | A | 3/1996 | Desarzens et al. |
| 5,507,288 | A | 4/1996 | Bocker et al. |
| 5,508,203 | A | 4/1996 | Fuller et al. |
| 5,513,636 | A | 5/1996 | Palti |
| 5,518,601 | A | 5/1996 | Foos et al. |
| 5,531,878 | A | 7/1996 | Vadgama et al. |
| 5,540,828 | A | 7/1996 | Yacynych |
| 5,545,220 | A | 8/1996 | Andrews et al. |
| 5,553,616 | A | 9/1996 | Ham et al. |
| 5,568,806 | A | 10/1996 | Cheney, II et al. |
| 5,569,186 | A | 10/1996 | Lord et al. |
| 5,575,930 | A | 11/1996 | Tietje-Girault et al. |
| 5,582,184 | A | 12/1996 | Erickson et al. |
| 5,584,813 | A | 12/1996 | Livingston et al. |
| 5,584,876 | A | 12/1996 | Bruchman et al. |
| 5,586,553 | A | 12/1996 | Halili et al. |
| 5,590,651 | A | 1/1997 | Shaffer et al. |
| 5,593,440 | A | 1/1997 | Brauker et al. |
| 5,624,537 | A | 4/1997 | Turner et al. |
| 5,640,470 | A | 6/1997 | Iyer et al. |
| 5,653,756 | A | 8/1997 | Clarke et al. |

5,653,863 A 8/1997 Genshaw et al.
5,660,163 A 8/1997 Schulman et al.
5,683,562 A 11/1997 Schaffar et al.
5,686,829 A 11/1997 Girault
5,695,623 A 12/1997 Michel et al.
5,711,861 A 1/1998 Ward et al.
5,730,654 A 3/1998 Brown
5,743,262 A 4/1998 Lepper, Jr. et al.
5,749,907 A 5/1998 Mann
5,771,890 A 6/1998 Tamada
5,781,455 A 7/1998 Hyodo et al.
5,782,912 A 7/1998 Brauker et al.
5,787,900 A 8/1998 Butler et al.
5,791,344 A 8/1998 Schulman et al.
5,795,774 A 8/1998 Matsumoto et al.
5,798,065 A 8/1998 Picha
5,800,420 A 9/1998 Gross
5,800,529 A 9/1998 Brauker et al.
5,806,517 A 9/1998 Gerhardt et al.
5,807,375 A 9/1998 Gross et al.
5,807,406 A 9/1998 Brauker et al.
5,811,487 A 9/1998 Schulz, Jr. et al.
5,814,599 A 9/1998 Mitragotri et al.
5,822,715 A 10/1998 Worthington et al.
5,836,887 A 11/1998 Oka et al.
5,836,989 A 11/1998 Shelton
5,851,197 A 12/1998 Marano et al.
5,861,019 A 1/1999 Sun et al.
5,863,400 A 1/1999 Drummond et al.
5,871,514 A 2/1999 Wiklund et al.
5,882,494 A 3/1999 Van Antwerp
5,897,578 A 4/1999 Wiklund et al.
5,899,855 A 5/1999 Brown
5,904,708 A 5/1999 Goedeke
5,913,998 A 6/1999 Butler et al.
5,914,026 A 6/1999 Blubaugh, Jr. et al.
5,917,346 A 6/1999 Gord
5,919,215 A 7/1999 Wiklund et al.
5,928,130 A 7/1999 Schmidt
5,928,155 A 7/1999 Eggers et al.
5,931,814 A 8/1999 Alex et al.
5,933,136 A 8/1999 Brown
5,944,661 A 8/1999 Swette et al.
5,957,854 A 9/1999 Besson et al.
5,957,903 A 9/1999 Mirzaee et al.
5,961,451 A 10/1999 Reber et al.
5,964,993 A 10/1999 Blubaugh et al.
5,965,380 A 10/1999 Heller et al.
5,971,922 A 10/1999 Arita et al.
5,976,085 A 11/1999 Kimball et al.
5,995,860 A 11/1999 Sun et al.
5,999,848 A 12/1999 Gord et al.
6,001,067 A 12/1999 Shults et al.
6,001,471 A 12/1999 Bries et al.
6,011,984 A 1/2000 Van Antwerp et al.
6,016,448 A 1/2000 Busacker et al.
6,023,629 A 2/2000 Tamada
6,027,445 A 2/2000 Von Bahr
6,036,924 A 3/2000 Simons et al.
6,049,727 A 4/2000 Crothall
6,059,946 A 5/2000 Yukawa et al.
6,063,637 A 5/2000 Arnold et al.
6,081,735 A 6/2000 Diab et al.
6,081,736 A 6/2000 Colvin et al.
6,083,523 A 7/2000 Dionne et al.
6,083,710 A 7/2000 Heller et al.
6,088,608 A 7/2000 Schulman et al.
6,091,975 A 7/2000 Daddona et al.
6,093,172 A 7/2000 Funderburk et al.
6,103,033 A 8/2000 Say et al.
6,107,083 A 8/2000 Collins et al.
6,115,634 A 9/2000 Donders et al.
6,120,676 A 9/2000 Heller et al.
6,121,009 A 9/2000 Heller et al.
6,122,536 A 9/2000 Sun et al.
6,123,827 A 9/2000 Wong et al.
6,127,154 A 10/2000 Mosbach et al.
6,134,461 A 10/2000 Say et al.
6,135,978 A 10/2000 Houben et al.
6,142,939 A 11/2000 Eppstein et al.
6,144,869 A 11/2000 Berner et al.
6,162,611 A 12/2000 Heller et al.
6,167,614 B1 1/2001 Tuttle et al.
6,168,568 B1 1/2001 Gavriely
6,175,752 B1 1/2001 Say et al.
6,180,416 B1 1/2001 Kurnik et al.
6,187,062 B1 2/2001 Oweis et al.
6,189,536 B1 2/2001 Martinez et al.
6,201,980 B1 3/2001 Darrow et al.
6,201,993 B1 3/2001 Kruse et al.
6,206,856 B1 3/2001 Mahurkar
6,208,894 B1 3/2001 Schulman et al.
6,212,416 B1 4/2001 Ward et al.
6,212,424 B1 4/2001 Robinson
6,214,185 B1 4/2001 Offenbacher et al.
6,223,083 B1 4/2001 Rosar
6,230,059 B1 5/2001 Duffin
6,231,879 B1 5/2001 Li et al.
6,233,080 B1 5/2001 Brenner et al.
6,233,471 B1 5/2001 Berner et al.
6,241,863 B1 6/2001 Monbouquette
6,248,067 B1 6/2001 Causey, III et al.
6,256,522 B1 7/2001 Schultz
6,259,937 B1 7/2001 Schulman et al.
6,272,364 B1 8/2001 Kurnik
6,272,480 B1 8/2001 Tresp et al.
6,274,285 B1 8/2001 Gries et al.
6,275,717 B1 8/2001 Gross et al.
6,284,478 B1 9/2001 Heller et al.
6,293,925 B1 9/2001 Safabash et al.
6,298,254 B2 10/2001 Tamada
6,299,578 B1 10/2001 Kurnik et al.
6,300,002 B1 10/2001 Webb et al.
6,309,351 B1 10/2001 Kurnik et al.
6,309,884 B1 10/2001 Cooper et al.
6,325,978 B1 12/2001 Labuda et al.
6,326,160 B1 12/2001 Dunn et al.
6,329,161 B1 12/2001 Heller et al.
6,329,929 B1 12/2001 Weijand et al.
6,330,464 B1 12/2001 Colvin, Jr. et al.
6,343,225 B1 1/2002 Clark, Jr.
6,356,776 B1 3/2002 Berner et al.
6,365,670 B1 4/2002 Fry
6,366,794 B1 4/2002 Moussy et al.
6,370,941 B2 4/2002 Nakamura
6,379,301 B1 4/2002 Worthington et al.
6,387,709 B1 5/2002 Mason et al.
6,413,393 B1 7/2002 Van Antwerp et al.
6,416,651 B1 7/2002 Miller
6,424,847 B1 7/2002 Mastrototaro et al.
6,447,448 B1 9/2002 Ishikawa et al.
6,447,542 B1 9/2002 Weadock
6,461,496 B1 10/2002 Feldman et al.
6,466,810 B1 10/2002 Ward et al.
6,471,689 B1 10/2002 Joseph et al.
6,475,750 B1 11/2002 Han et al.
6,477,392 B1 11/2002 Honigs et al.
6,477,395 B2 11/2002 Schulman et al.
6,481,440 B2 11/2002 Gielen et al.
6,484,046 B1 11/2002 Say et al.
6,494,830 B1 12/2002 Wessel
6,498,043 B1 12/2002 Schulman et al.
6,510,329 B2 1/2003 Heckel
6,512,939 B1 1/2003 Colvin et al.
6,520,997 B1 2/2003 Pekkarinen et al.
6,526,298 B1 2/2003 Khalil et al.
6,527,729 B1 3/2003 Turcott
6,537,318 B1 3/2003 Ita et al.
6,541,266 B2 4/2003 Modzelewski et al.
6,544,212 B2 4/2003 Galley et al.
6,545,085 B2 4/2003 Kilgour et al.
6,546,268 B1 4/2003 Ishikawa et al.
6,546,269 B1 4/2003 Kurnik
6,551,496 B1 4/2003 Moles et al.
6,553,241 B2 4/2003 Mannheimer et al.
6,553,244 B2 4/2003 Lesho et al.
6,558,320 B1 5/2003 Causey
6,558,321 B1 5/2003 Burd et al.

| | | | | |
|---|---|---|---|---|
| 6,558,351 | B1 | 5/2003 | Steil et al. | |
| 6,560,471 | B1 | 5/2003 | Heller et al. | |
| 6,561,978 | B1 | 5/2003 | Conn et al. | |
| 6,565,509 | B1 | 5/2003 | Say et al. | |
| 6,569,521 | B1 | 5/2003 | Sheridan et al. | |
| 6,572,545 | B2 | 6/2003 | Knobbe et al. | |
| 6,574,490 | B2 | 6/2003 | Abbink et al. | |
| 6,575,905 | B2 | 6/2003 | Knobbe et al. | |
| 6,579,498 | B1 | 6/2003 | Eglise | |
| 6,579,690 | B1 | 6/2003 | Bonnecaze et al. | |
| 6,585,644 | B2 | 7/2003 | Lebel et al. | |
| 6,585,763 | B1 | 7/2003 | Keilman et al. | |
| 6,589,229 | B1 | 7/2003 | Connelly et al. | |
| 6,591,125 | B1 | 7/2003 | Buse et al. | |
| 6,595,919 | B2 | 7/2003 | Berner et al. | |
| 6,605,072 | B2 | 8/2003 | Struys et al. | |
| 6,607,509 | B2 | 8/2003 | Bobroff et al. | |
| 6,613,379 | B2 | 9/2003 | Ward et al. | |
| 6,618,934 | B1 | 9/2003 | Feldman et al. | |
| 6,633,772 | B2 | 10/2003 | Ford et al. | |
| 6,641,533 | B2 | 11/2003 | Causey et al. | |
| 6,642,015 | B2 | 11/2003 | Vachon et al. | |
| 6,645,181 | B1 | 11/2003 | Lavi et al. | |
| 6,648,821 | B2 | 11/2003 | Lebel et al. | |
| 6,653,091 | B1 | 11/2003 | Dunn et al. | |
| 6,654,625 | B1 | 11/2003 | Say et al. | |
| 6,673,022 | B1 | 1/2004 | Bobo et al. | |
| 6,673,596 | B1 | 1/2004 | Sayler et al. | |
| 6,683,535 | B1 | 1/2004 | Utke | |
| 6,687,522 | B2 | 2/2004 | Tamada | |
| 6,694,191 | B2 | 2/2004 | Starkweather et al. | |
| 6,695,860 | B1 | 2/2004 | Ward et al. | |
| 6,699,188 | B2 | 3/2004 | Wessel | |
| 6,699,218 | B2 | 3/2004 | Flaherty et al. | |
| 6,702,857 | B2 | 3/2004 | Brauker et al. | |
| 6,702,972 | B1 | 3/2004 | Markle | |
| 6,721,587 | B2 | 4/2004 | Gough | |
| 6,731,976 | B2 | 5/2004 | Penn et al. | |
| 6,740,075 | B2 | 5/2004 | Lebel et al. | |
| 6,741,877 | B1 | 5/2004 | Shults et al. | |
| 6,810,290 | B2 | 10/2004 | Lebel et al. | |
| 6,869,413 | B2 | 3/2005 | Langley et al. | |
| 6,892,085 | B2 | 5/2005 | McIvor et al. | |
| 6,895,263 | B2 | 5/2005 | Shin et al. | |
| 6,925,393 | B1 | 8/2005 | Kalatz et al. | |
| 6,931,327 | B2 | 8/2005 | Goode et al. | |
| 6,952,604 | B2 | 10/2005 | DeNuzzio et al. | |
| 6,998,247 | B2 | 2/2006 | Monfre et al. | |
| 7,011,630 | B2 | 3/2006 | Desai et al. | |
| 7,016,713 | B2 * | 3/2006 | Gardner et al. | 600/310 |
| 7,022,072 | B2 | 4/2006 | Fox et al. | |
| 7,025,743 | B2 | 4/2006 | Mann et al. | |
| 7,027,848 | B2 | 4/2006 | Robinson et al. | |
| 7,029,444 | B2 | 4/2006 | Shin et al. | |
| 7,060,059 | B2 | 6/2006 | Keith et al. | |
| 7,074,307 | B2 | 7/2006 | Simpson et al. | |
| 7,098,803 | B2 | 8/2006 | Mann et al. | |
| 7,108,778 | B2 | 9/2006 | Simpson et al. | |
| 7,134,999 | B2 | 11/2006 | Brauker et al. | |
| 7,169,289 | B2 | 1/2007 | Schulein et al. | |
| 7,183,102 | B2 | 2/2007 | Monfre et al. | |
| 7,229,288 | B2 | 6/2007 | Stuart et al. | |
| 7,261,690 | B2 | 8/2007 | Teller et al. | |
| 7,267,665 | B2 | 9/2007 | Steil et al. | |
| 7,276,029 | B2 | 10/2007 | Goode et al. | |
| 7,278,983 | B2 | 10/2007 | Ireland et al. | |
| 7,295,867 | B2 | 11/2007 | Berner et al. | |
| 7,299,082 | B2 | 11/2007 | Feldman et al. | |
| 7,354,420 | B2 | 4/2008 | Steil et al. | |
| 7,359,723 | B2 | 4/2008 | Jones | |
| 7,399,277 | B2 | 7/2008 | Saidara et al. | |
| 7,402,153 | B2 | 7/2008 | Steil et al. | |
| 7,417,164 | B2 | 8/2008 | Suri | |
| 7,426,408 | B2 | 9/2008 | DeNuzzio et al. | |
| 7,433,727 | B2 | 10/2008 | Ward et al. | |
| 7,519,408 | B2 | 4/2009 | Rasdal et al. | |
| 7,519,478 | B2 | 4/2009 | Bartkowiak et al. | |
| 7,523,004 | B2 | 4/2009 | Bartkowiak et al. | |
| 7,583,990 | B2 | 9/2009 | Goode, Jr. et al. | |
| 7,591,801 | B2 | 9/2009 | Brauker et al. | |
| 7,599,726 | B2 | 10/2009 | Goode, Jr. et al. | |
| 7,604,593 | B2 | 10/2009 | Parris et al. | |
| 7,618,368 | B2 | 11/2009 | Brown | |
| 7,618,369 | B2 | 11/2009 | Hayter et al. | |
| 7,624,028 | B1 | 11/2009 | Brown | |
| 7,640,032 | B2 | 12/2009 | Jones | |
| 7,640,048 | B2 | 12/2009 | Dobbles et al. | |
| 7,647,237 | B2 | 1/2010 | Malave et al. | |
| 7,695,434 | B2 | 4/2010 | Malecha | |
| 7,711,493 | B2 | 5/2010 | Bartkowiak et al. | |
| 7,731,659 | B2 | 6/2010 | Malecha | |
| 7,761,126 | B2 * | 7/2010 | Gardner et al. | 600/310 |
| 7,766,830 | B2 | 8/2010 | Fox et al. | |
| 7,927,274 | B2 | 4/2011 | Rasdal et al. | |
| 7,946,985 | B2 | 5/2011 | Mastrototaro et al. | |
| 8,000,901 | B2 | 8/2011 | Brauker et al. | |
| 8,005,524 | B2 | 8/2011 | Brauker et al. | |
| 8,005,525 | B2 | 8/2011 | Goode et al. | |
| 8,010,174 | B2 | 8/2011 | Goode et al. | |
| 2001/0016682 | A1 | 8/2001 | Berner et al. | |
| 2001/0041830 | A1 | 11/2001 | Varalli et al. | |
| 2001/0044588 | A1 | 11/2001 | Mault et al. | |
| 2001/0051768 | A1 | 12/2001 | Schulman et al. | |
| 2002/0016535 | A1 | 2/2002 | Martin et al. | |
| 2002/0019022 | A1 | 2/2002 | Dunn et al. | |
| 2002/0022883 | A1 | 2/2002 | Burg | |
| 2002/0026110 | A1 | 2/2002 | Parris et al. | |
| 2002/0026111 | A1 | 2/2002 | Ackerman | |
| 2002/0042090 | A1 | 4/2002 | Heller et al. | |
| 2002/0042561 | A1 | 4/2002 | Schulman et al. | |
| 2002/0045808 | A1 | 4/2002 | Ford et al. | |
| 2002/0065453 | A1 | 5/2002 | Lesho et al. | |
| 2002/0068860 | A1 | 6/2002 | Clark, Jr. | |
| 2002/0099282 | A1 | 7/2002 | Knobbe et al. | |
| 2002/0111547 | A1 | 8/2002 | Knobbe et al. | |
| 2002/0119711 | A1 | 8/2002 | Van Antwerp et al. | |
| 2002/0151796 | A1 | 10/2002 | Koulik | |
| 2002/0155615 | A1 | 10/2002 | Novikov et al. | |
| 2002/0161288 | A1 | 10/2002 | Shin et al. | |
| 2002/0182241 | A1 | 12/2002 | Boerenstein et al. | |
| 2002/0193679 | A1 | 12/2002 | Malave et al. | |
| 2002/0193885 | A1 | 12/2002 | Legeay et al. | |
| 2002/0198513 | A1 | 12/2002 | Lebel et al. | |
| 2003/0004432 | A1 | 1/2003 | Assenheimer | |
| 2003/0004457 | A1 | 1/2003 | Andersson | |
| 2003/0006669 | A1 | 1/2003 | Pei et al. | |
| 2003/0021729 | A1 | 1/2003 | Moller et al. | |
| 2003/0023171 | A1 | 1/2003 | Sato et al. | |
| 2003/0023317 | A1 | 1/2003 | Brauker et al. | |
| 2003/0028089 | A1 | 2/2003 | Galley et al. | |
| 2003/0032874 | A1 | 2/2003 | Rhodes et al. | |
| 2003/0050546 | A1 | 3/2003 | Desai et al. | |
| 2003/0054428 | A1 | 3/2003 | Monfre et al. | |
| 2003/0060765 | A1 | 3/2003 | Campbell et al. | |
| 2003/0070548 | A1 | 4/2003 | Clausen | |
| 2003/0076082 | A1 | 4/2003 | Morgan et al. | |
| 2003/0078481 | A1 | 4/2003 | McIvor et al. | |
| 2003/0078560 | A1 | 4/2003 | Miller et al. | |
| 2003/0097082 | A1 | 5/2003 | Purdy et al. | |
| 2003/0100040 | A1 | 5/2003 | Bonnecaze et al. | |
| 2003/0100821 | A1 | 5/2003 | Heller et al. | |
| 2003/0117296 | A1 | 6/2003 | Seely | |
| 2003/0120152 | A1 | 6/2003 | Omiya | |
| 2003/0125612 | A1 | 7/2003 | Fox et al. | |
| 2003/0125613 | A1 | 7/2003 | Enegren et al. | |
| 2003/0130616 | A1 | 7/2003 | Steil et al. | |
| 2003/0134347 | A1 | 7/2003 | Heller et al. | |
| 2003/0176183 | A1 | 9/2003 | Drucker et al. | |
| 2003/0187338 | A1 | 10/2003 | Say et al. | |
| 2003/0188427 | A1 | 10/2003 | Say et al. | |
| 2003/0211625 | A1 | 11/2003 | Cohan | |
| 2003/0212317 | A1 | 11/2003 | Kovatchev et al. | |
| 2003/0212346 | A1 | 11/2003 | Yuzhakov et al. | |
| 2003/0212347 | A1 | 11/2003 | Sohrab | |
| 2003/0217966 | A1 | 11/2003 | Tapsak et al. | |
| 2003/0225437 | A1 | 12/2003 | Ferguson | |
| 2003/0231550 | A1 | 12/2003 | Macfarlane | |
| 2003/0235817 | A1 | 12/2003 | Bartkowiak et al. | |

| | | | |
|---|---|---|---|
| 2004/0011671 | A1 | 1/2004 | Shults et al. |
| 2004/0015063 | A1 | 1/2004 | DeNuzzio et al. |
| 2004/0015134 | A1 | 1/2004 | Lavi et al. |
| 2004/0024327 | A1 | 2/2004 | Brodnick |
| 2004/0030285 | A1 | 2/2004 | Lavi et al. |
| 2004/0039298 | A1 | 2/2004 | Abreu |
| 2004/0040840 | A1 | 3/2004 | Mao et al. |
| 2004/0045879 | A1 | 3/2004 | Shults et al. |
| 2004/0068230 | A1 | 4/2004 | Estes et al. |
| 2004/0078219 | A1 | 4/2004 | Kaylor |
| 2004/0106857 | A1 | 6/2004 | Gough |
| 2004/0143173 | A1 | 7/2004 | Reghabi et al. |
| 2004/0146909 | A1 | 7/2004 | Duong et al. |
| 2004/0152187 | A1 | 8/2004 | Haight et al. |
| 2004/0152622 | A1 | 8/2004 | Keith et al. |
| 2004/0167801 | A1 | 8/2004 | Say et al. |
| 2004/0186362 | A1 | 9/2004 | Brauker et al. |
| 2004/0186365 | A1 | 9/2004 | Jin et al. |
| 2004/0199059 | A1 | 10/2004 | Brauker et al. |
| 2004/0219664 | A1 | 11/2004 | Heller et al. |
| 2004/0220517 | A1 | 11/2004 | Starkweather et al. |
| 2005/0010265 | A1 | 1/2005 | Baru Fassio et al. |
| 2005/0027180 | A1 | 2/2005 | Goode et al. |
| 2005/0027181 | A1 | 2/2005 | Goode et al. |
| 2005/0027182 | A1 | 2/2005 | Siddiqui et al. |
| 2005/0027462 | A1 | 2/2005 | Goode et al. |
| 2005/0027463 | A1 | 2/2005 | Goode et al. |
| 2005/0033132 | A1 | 2/2005 | Shults et al. |
| 2005/0038332 | A1 | 2/2005 | Saidara et al. |
| 2005/0043598 | A1 | 2/2005 | Goode et al. |
| 2005/0051427 | A1 | 3/2005 | Brauker et al. |
| 2005/0051440 | A1 | 3/2005 | Simpson et al. |
| 2005/0054909 | A1 | 3/2005 | Petisce et al. |
| 2005/0056552 | A1 | 3/2005 | Simpson et al. |
| 2005/0090607 | A1 | 4/2005 | Tapsak et al. |
| 2005/0096519 | A1 | 5/2005 | DeNuzzio et al. |
| 2005/0101847 | A1 | 5/2005 | Routt et al. |
| 2005/0112169 | A1 | 5/2005 | Brauker et al. |
| 2005/0113653 | A1 | 5/2005 | Fox et al. |
| 2005/0115832 | A1 | 6/2005 | Simpson et al. |
| 2005/0121322 | A1 | 6/2005 | Say |
| 2005/0139489 | A1 | 6/2005 | Oliver et al. |
| 2005/0143635 | A1 | 6/2005 | Kamath et al. |
| 2005/0143675 | A1 | 6/2005 | Neel et al. |
| 2005/0154271 | A1 | 7/2005 | Rasdal et al. |
| 2005/0177398 | A1 | 8/2005 | Watanabe et al. |
| 2005/0187720 | A1 | 8/2005 | Goode et al. |
| 2005/0192557 | A1 | 9/2005 | Brauker et al. |
| 2005/0203360 | A1 | 9/2005 | Brauker et al. |
| 2005/0211571 | A1 | 9/2005 | Schulein et al. |
| 2005/0215872 | A1 | 9/2005 | Berner et al. |
| 2005/0239154 | A1 | 10/2005 | Feldman et al. |
| 2005/0242479 | A1 | 11/2005 | Petisce et al. |
| 2005/0245795 | A1 | 11/2005 | Goode et al. |
| 2005/0245799 | A1 | 11/2005 | Brauker et al. |
| 2006/0015020 | A1 | 1/2006 | Neale et al. |
| 2006/0015024 | A1 | 1/2006 | Brister et al. |
| 2006/0016700 | A1 | 1/2006 | Brister et al. |
| 2006/0019327 | A1 | 1/2006 | Brister et al. |
| 2006/0020186 | A1 | 1/2006 | Brister et al. |
| 2006/0020187 | A1 | 1/2006 | Brister et al. |
| 2006/0020188 | A1 | 1/2006 | Kamath et al. |
| 2006/0020189 | A1 | 1/2006 | Brister et al. |
| 2006/0020190 | A1 | 1/2006 | Kamath et al. |
| 2006/0020191 | A1 | 1/2006 | Brister et al. |
| 2006/0020192 | A1 | 1/2006 | Brister et al. |
| 2006/0036139 | A1 | 2/2006 | Brister et al. |
| 2006/0036140 | A1 | 2/2006 | Brister et al. |
| 2006/0036141 | A1 | 2/2006 | Kamath et al. |
| 2006/0036142 | A1 | 2/2006 | Brister et al. |
| 2006/0036143 | A1 | 2/2006 | Brister et al. |
| 2006/0036144 | A1 | 2/2006 | Brister et al. |
| 2006/0036145 | A1 | 2/2006 | Brister et al. |
| 2006/0040402 | A1 | 2/2006 | Brauker et al. |
| 2006/0074564 | A1 | 4/2006 | Bartkowiak et al. |
| 2006/0100588 | A1 | 5/2006 | Brunnberg et al. |
| 2006/0183984 | A1 | 8/2006 | Dobbles et al. |
| 2006/0183985 | A1 | 8/2006 | Brister et al. |
| 2006/0222566 | A1 | 10/2006 | Brauker et al. |
| 2006/0258929 | A1 | 11/2006 | Goode et al. |
| 2006/0281985 | A1 | 12/2006 | Ward et al. |
| 2007/0016381 | A1 | 1/2007 | Kamath et al. |
| 2007/0032706 | A1 | 2/2007 | Kamath et al. |
| 2007/0049873 | A1 | 3/2007 | Hansen et al. |
| 2007/0066873 | A1 | 3/2007 | Kamath et al. |
| 2007/0203410 | A1 | 8/2007 | Say et al. |
| 2007/0203966 | A1 | 8/2007 | Brauker et al. |
| 2007/0208244 | A1 | 9/2007 | Brauker et al. |
| 2007/0208245 | A1 | 9/2007 | Brauker et al. |
| 2007/0208246 | A1 | 9/2007 | Brauker et al. |
| 2007/0213610 | A1 | 9/2007 | Say et al. |
| 2007/0255126 | A1 | 11/2007 | Moberg et al. |
| 2007/0282180 | A1 | 12/2007 | Caduff et al. |
| 2008/0021666 | A1 | 1/2008 | Goode et al. |
| 2008/0033254 | A1 | 2/2008 | Kamath et al. |
| 2008/0071157 | A1 | 3/2008 | Mcgarraugh et al. |
| 2008/0071158 | A1 | 3/2008 | Mcgarraugh et al. |
| 2008/0072663 | A1 | 3/2008 | Keenan et al. |
| 2008/0139910 | A1 | 6/2008 | Mastrototaro et al. |
| 2008/0183061 | A1 | 7/2008 | Goode et al. |
| 2008/0183399 | A1 | 7/2008 | Goode et al. |
| 2008/0187655 | A1 | 8/2008 | Markle et al. |
| 2008/0188722 | A1 | 8/2008 | Markle et al. |
| 2008/0188725 | A1 | 8/2008 | Markle et al. |
| 2008/0189051 | A1 | 8/2008 | Goode et al. |
| 2008/0194936 | A1 | 8/2008 | Goode et al. |
| 2008/0194937 | A1 | 8/2008 | Goode et al. |
| 2008/0195967 | A1 | 8/2008 | Goode et al. |
| 2008/0287764 | A1 | 11/2008 | Rasdal et al. |
| 2008/0287765 | A1 | 11/2008 | Rasdal et al. |
| 2008/0287766 | A1 | 11/2008 | Rasdal et al. |
| 2008/0305009 | A1 | 12/2008 | Gamsey et al. |
| 2008/0305506 | A1 | 12/2008 | Suri |
| 2008/0306368 | A1 | 12/2008 | Goode et al. |
| 2008/0306434 | A1 | 12/2008 | Dobbles et al. |
| 2008/0306435 | A1 | 12/2008 | Kamath et al. |
| 2008/0306444 | A1 | 12/2008 | Brister et al. |
| 2009/0005666 | A1 | 1/2009 | Shin et al. |
| 2009/0012379 | A1 | 1/2009 | Goode et al. |
| 2009/0018418 | A1 | 1/2009 | Markle et al. |
| 2009/0018426 | A1 | 1/2009 | Markle et al. |
| 2009/0036758 | A1 | 2/2009 | Brauker et al. |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043542 | A1 | 2/2009 | Brauker et al. |
| 2009/0061528 | A1 | 3/2009 | Suri |
| 2009/0062635 | A1 | 3/2009 | Brauker et al. |
| 2009/0076361 | A1 | 3/2009 | Kamath et al. |
| 2009/0081803 | A1 | 3/2009 | Gamsey et al. |
| 2009/0124877 | A1 | 5/2009 | Goode, Jr. et al. |
| 2009/0124878 | A1 | 5/2009 | Goode, Jr. et al. |
| 2009/0156924 | A1 | 6/2009 | Shariati et al. |
| 2009/0177143 | A1 | 7/2009 | Markle et al. |
| 2009/0182217 | A1 | 7/2009 | Li et al. |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0203981 | A1 | 8/2009 | Brauker et al. |
| 2009/0204341 | A1 | 8/2009 | Brauker et al. |
| 2009/0216103 | A1 | 8/2009 | Brister et al. |
| 2009/0240120 | A1 | 9/2009 | Mensinger et al. |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0264719 | A1 | 10/2009 | Markle et al. |
| 2009/0264856 | A1 | 10/2009 | Lebel et al. |
| 2009/0287074 | A1 | 11/2009 | Shults et al. |
| 2009/0299162 | A1 | 12/2009 | Brauker et al. |
| 2009/0299276 | A1 | 12/2009 | Brauker et al. |
| 2010/0010324 | A1 | 1/2010 | Brauker et al. |
| 2010/0010331 | A1 | 1/2010 | Brauker et al. |
| 2010/0010332 | A1 | 1/2010 | Brauker et al. |
| 2010/0016687 | A1 | 1/2010 | Brauker et al. |

| | | | |
|---|---|---|---|
| 2010/0022855 | A1 | 1/2010 | Brauker et al. |
| 2010/0030038 | A1 | 2/2010 | Brauker et al. |
| 2010/0030053 | A1 | 2/2010 | Goode, Jr. et al. |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036224 | A1 | 2/2010 | Goode, Jr. et al. |
| 2010/0036225 | A1 | 2/2010 | Goode, Jr. et al. |
| 2010/0045465 | A1 | 2/2010 | Brauker et al. |
| 2010/0179400 | A1 | 7/2010 | Brauker et al. |
| 2010/0179401 | A1 | 7/2010 | Rasdal et al. |
| 2010/0179407 | A1 | 7/2010 | Goode, Jr. et al. |
| 2010/0179408 | A1 | 7/2010 | Kamath et al. |
| 2010/0179409 | A1 | 7/2010 | Kamath et al. |
| 2010/0234707 | A1 | 9/2010 | Goode, Jr. et al. |
| 2010/0235106 | A1 | 9/2010 | Goode, Jr. et al. |
| 2010/0240975 | A1 | 9/2010 | Goode, Jr. et al. |
| 2010/0240976 | A1 | 9/2010 | Goode, Jr. et al. |
| 2010/0331656 | A1 | 12/2010 | Mensinger et al. |
| 2010/0331657 | A1 | 12/2010 | Mensinger et al. |
| 2011/0009727 | A1 | 1/2011 | Mensinger et al. |
| 2011/0118579 | A1 | 5/2011 | Goode, Jr. et al. |
| 2011/0124997 | A1 | 5/2011 | Goode, Jr. et al. |
| 2011/0130970 | A1 | 6/2011 | Goode, Jr. et al. |
| 2011/0137601 | A1 | 6/2011 | Goode, Jr. et al. |
| 2011/0218414 | A1 | 9/2011 | Kamath et al. |
| 2011/0231107 | A1 | 9/2011 | Brauker et al. |
| 2011/0231140 | A1 | 9/2011 | Goode, Jr. et al. |
| 2011/0231141 | A1 | 9/2011 | Goode, Jr. et al. |
| 2011/0231142 | A1 | 9/2011 | Goode, Jr. et al. |
| 2011/0257895 | A1 | 10/2011 | Brauker et al. |
| 2011/0263958 | A1 | 10/2011 | Brauker et al. |

FOREIGN PATENT DOCUMENTS

| | | |
|---|---|---|
| EP | 0 098 592 | 1/1984 |
| EP | 0 107 634 | 5/1984 |
| EP | 0 127 958 | 12/1984 |
| EP | 0 286 118 | 10/1988 |
| EP | 0 288 793 | 11/1988 |
| EP | 0 320 109 | 6/1989 |
| EP | 0 352 610 | 1/1990 |
| EP | 0 352 631 | 1/1990 |
| EP | 0 353 328 | 2/1990 |
| EP | 0 390 390 | 10/1990 |
| EP | 0 406 473 | 1/1991 |
| EP | 0 440 044 | 8/1991 |
| EP | 0 441 252 | 8/1991 |
| EP | 0 467 078 | 1/1992 |
| EP | 0 563 795 | 10/1993 |
| EP | 0 323 605 | 1/1994 |
| EP | 0 647 849 | 4/1995 |
| EP | 0 424 633 | 1/1996 |
| EP | 0 776 628 | 6/1997 |
| EP | 0 817 809 | 1/1998 |
| EP | 0 838 230 | 4/1998 |
| EP | 0 880 936 | 12/1998 |
| EP | 0 885 932 | 12/1998 |
| EP | 1 077 634 | 2/2001 |
| EP | 1 078 258 | 2/2001 |
| EP | 1 153 571 | 11/2001 |
| EP | 2 226 086 | 8/2010 |
| EP | 2 223 710 | 9/2010 |
| FR | 2656423 | 6/1991 |
| FR | 2760962 | 9/1998 |
| GB | 1 442 303 | 7/1976 |
| GB | 2149918 | 6/1985 |
| JP | 2000-060826 | 2/2000 |
| JP | 2003-108679 | 4/2003 |
| WO | WO 89/02720 | 4/1989 |
| WO | WO 90/00738 | 1/1990 |
| WO | WO 90/10861 | 9/1990 |
| WO | WO 92/13271 | 8/1992 |
| WO | WO 93/14693 | 8/1993 |
| WO | WO 94/22367 | 10/1994 |
| WO | WO 95/07109 | 3/1995 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/28737 | 8/1997 |
| WO | WO 98/24358 | 6/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 99/59657 | 11/1999 |
| WO | WO 00/12720 | 3/2000 |
| WO | WO 00/13002 | 3/2000 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 00/74753 | 12/2000 |
| WO | WO 00/78210 | 12/2000 |
| WO | WO 01/16579 | 3/2001 |
| WO | WO 01/20019 | 3/2001 |
| WO | WO 01/20334 | 3/2001 |
| WO | WO 01/34243 | 5/2001 |
| WO | WO 01/52727 | 7/2001 |
| WO | WO 01/58348 | 8/2001 |
| WO | WO 01/68901 | 9/2001 |
| WO | WO 01/69222 | 9/2001 |
| WO | WO 01/88524 | 11/2001 |
| WO | WO 01/88534 | 11/2001 |
| WO | WO 02/05702 | 1/2002 |
| WO | WO 02/24065 | 3/2002 |
| WO | WO 02/082989 | 10/2002 |
| WO | WO 02/089666 | 11/2002 |
| WO | WO 02/100266 | 12/2002 |
| WO | WO 03/000127 | 1/2003 |
| WO | WO 03/101862 | 12/2003 |
| WO | WO 2004/110256 | 12/2004 |
| WO | WO 2005/011489 | 2/2005 |
| WO | WO 2005/012873 | 2/2005 |
| WO | WO 2005/032400 | 4/2005 |
| WO | WO 2005/057168 | 6/2005 |
| WO | WO 2005/057175 | 6/2005 |
| WO | WO 2005/078424 | 8/2005 |
| WO | WO 2006/050405 | 5/2006 |
| WO | WO 2006/105146 | 10/2006 |
| WO | WO 2006/118713 | 11/2006 |
| WO | WO 2006/131288 | 12/2006 |
| WO | WO 2007/002579 | 1/2007 |
| WO | WO 2007/065285 | 6/2007 |
| WO | WO 2007/114943 | 10/2007 |
| WO | WO 2007/127606 | 11/2007 |
| WO | WO 2007/143225 | 12/2007 |
| WO | WO 2008/076868 | 6/2008 |

OTHER PUBLICATIONS

Jaffari et al. 1995. Recent advances in amperometric glucose biosensors for in vivo monitoring, Physiol. Meas. 16: 1-15.

Jobst et al., (1996) Thin-Film Microbiosensors for Glucose-Lactate Monitoring, Anal Chem. 8(18): 3173-3179.

Mazzola et al., Video Diabetes: A Teaching Tool for Children with Insulin-Dependent Diabetes, Proceedings—7th Annual Symposium on Computer Applications in Medical Care; Washington, D.C.; Dialog:, (Oct. 1983), File 8, Acc# 01624462.

Moussy et al. 1993. Performance of subcutaneously implanted needle-type glucose sensors employing a novel trilayer coating, Anal Chem. 85: 2072-2077.

Moussy, Francis (Nov. 2002) Implantable Glucose Sensor: Progress and Problems, Sensors, 1:270-273.

Nintendo Healthcare, Wired, Dec. 1993.

Samuels, M.P. 2004. The effects of flight and altitude. Arch Dis Child. 89: 448-455.

Thijssen et al. 1984. A Kalman Filter for Calibration, Evaluation of Unknown Samples and Quality Control in Drifting Systems, Part 1. Theory and Simulations, Anal Chim Acta 156: 87-101.

Thijssen et al. 1985. A Kalman Filter for Calibration, Evaluation of Unknown Samples and Quality Control in Drifting Systems, Part 3. Variance Reduction, Anal Chim Acta. 173: 265-272.

Thijssen et al. 1985. A Kalman Filter for Calibration, Evaluation of Unknown Samples and Quality Control in Drifting Systems, Part 4. Flow Injection Analysis, Anal Chim Acta. 174: 27-40.
Thijssen, P.C. 1984. A Kalman Filder for Calibration, Evaluation of Unknown Samples and Quality Control in Drifting Systems, Part 2. Optimal Designs, Anal Chim Acta. 162: 253-262.
Ward et al. 2004. A wire-based dual-analyte sensor for Glucose and Lactate: In Vitro and In Vivo Evaluation, Diab Tech Therapeut. 6(3): 389-401.
EPO Communication dated Sep. 22, 2010 in EP Application No. 04813418.3 filed Nov. 8, 2004.
EPO Search Report dated Mar. 11, 2011 in EP Application No. 10193214.3, filed Dec. 8, 2004.
EPO Search Report dated Apr. 14, 2011 in EP Application No. 10193216.8, filed Dec. 8, 2004.
EPO Search Report dated Mar. 1, 2011 in EP Application No. 10193217.6, filed Dec. 8, 2004.
Electronic File History for U.S. Appl. No. 12/731,046, filed Mar. 24, 2010 (to issue USP 8,005,524 on Aug. 23, 2011) containing Office Action(s) dated Sep. 23, 2010, Mar. 3, 2011 and Jun. 3, 2011 and Applicant(s) Response(s) filed Dec. 21, 2010 and May 23, 2011.
Electronic File History for U.S. Appl. No. 12/565,173, filed Sep. 23, 2009 containing Office Action(s) dated Oct. 29, 2010 and May 12, 2011 and Applicant(s) Response(s) filed Feb. 25, 2011 and Jul. 12, 2011 as of Aug. 17, 2011.
Electronic File History for U.S. Appl. No. 11/007,920, filed Dec. 8, 2004 containing Office Action(s) dated Jun. 24, 2008, Dec. 19, 2008, Mar. 27, 2009, Jul. 27, 2009, Apr. 2, 2011, 12/27/10 and 6/2/2011 and Applicant(s) Response(s) filed Oct. 30, 2007, Sep. 24, 2008, Jan. 15, 2009, Apr. 15, 2009, Aug. 10, 2009, Dec. 22, 2009, May 26, 2010, Mar. 25, 2011 and Aur. 1, 2011 as of Aug. 16, 2011.
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and In Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Candas et al (1994). "An adaptive plasma glucose controller basedon on a nonlinear insulin/glucose model." *IEEE Transactions on Biomedical Engineering*, 41(2): 116-124.
Cass et al. "Ferrocene-mediated enzyme electrodes for amperometric determination of glucose," Anal. Chem., 36:667-71 (1984).
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Davies, et al. 1992. Polymer membranes in clinical sensor applications. I. An overview of membrane function, Biomaterials, 13(14):971-978.
Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson et al. 1992. In vivo evaluation of an electroenzymatic glucose sensor implanted in subcutaneous tissue. Biosensors & Bioelectronics, 7:709-714.
Kamath et al. Calibration of a continuous glucose monitor: effect of glucose rate of change, Eighth Annual Diabetes Technology Meeting, Nov. 13-15, 2008, p. A88.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Lohn et al., A knowledge-based system for real-time validation of calibrations and measurements, Chemometrics and Intelligent Laboratory Systems, 1999 46, 57-66.
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
McKean, et al. Jul. 7, 1988. A Telemetry Instrumentation System for Chronically Implanted Glucose and Oxygen Sensors. Transactions on Biomedical Engineering 35:526-532.
Moatti-Sirat et al. 1992. Towards continuous glucose monitoring: in vivo evaluation of a miniaturized glucose sensor implanted for several days in rat subcutaneous tissue. Diabetologia 35:224-230.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'- bipyridine)chloroosmium(+/2+) complexed poly(1-vinylimidazole) films, Analytical Chemistry, 65:3512-3517.
Pickup et al. "Implantable glucose sensors: choosing the appropriate sensor strategy," Biosensors, 3:335-346 (1987/88).
Pishko et al. "Amperometric glucose microelectrodes prepared through immobilization of glucose oxidase in redox hydrogels," Anal. Chem., 63:2268-72 (1991).
Poitout, et al. 1991. In Vitro and In Vivo Evaluation in Dogs of a Miniaturized Glucose Sensor, ASAIO Transactions, 37:M298-M300.
Prabhu et al. 1981. Electrochemical studies of hydrogen peroxide at a platinum disc electrode, Electrochimica Acta 26(6):725-729.
Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sakakida et al. 1993. Ferrocene-Mediated Needle Type Glucose Sensor Covered with Newly Designed Biocompatible Membran, Sensors and Actuators B 13-14:319-322.
Shaw et al. "In vitro testing of a simply constructed, highly stable glucose sensor suitable for implantation in diabetic patients," Biosensors & Bioelectronics, 6:401-406 (1991).
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1985. Needle-type Glucose Sensor for Wearable Artificial Endocrine Pancreas in Implantable Sensors 197-210.
Shichiri et al., 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sparacino et al., 2008. Continuous glucose monitoring time series and hypo/hyperglycemia prevention: requirements, methods, open problems, Current Diabetes Reviews, 4:181-192.
Sternberg et al. 1988. Study and Development of Multilayer Needle-type Enzyme-based Glucose Microsensors. Biosensors 4:27-40.
Thompson et al., In Vivo Probes: Problems and Perspectives, Department of Chemistry, University of Toronto, Canada, pp. 255-261, 1986.
Turner and Pickup, "Diabetes mellitus: biosensors for research and management," *Biosensors*, 1:85- 115 (1985).
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.
Wilson et al. 1992. Progress toward the development of an implantable sensor for glucose. Clin. Chem. 38(9):1613-1617.
Yang et al (1996). "A glucose biosensor based on an oxygen electrode: In-vitro performances in a model buffer solution and in blood plasma," Biomedical Instrumentation & Technology, 30:55-61.
Office Action dated Mar. 31, 2008 in U.S. Appl. No. 11/077,759.
Office Action dated Jun. 24, 2008 n U.S. Appl. No. 11/007,920.
Office Action dated Jul. 10, 2008 in U.S. Appl. No. 11/077,759.
Office Action dated Jul. 25, 2008 in U.S. Appl. No. 11/077,740.
Office Action dated Aug. 11, 2008 in U.S. Appl. No. 11/360,819.
Office Action dated Aug. 26, 2008 in U.S. Appl. No. 11/334,876.
Office Action dated Oct. 3, 2008 in U.S. Appl. No. 10/789,359.
Office Action dated Dec. 18, 2008 in U.S. Appl. No. 10/633,329.
Office Action dated Dec. 23, 2008 in U.S. Appl. No. 12/102,745.
Office Action dated Dec. 26, 2008 in U.S. Appl. No. 11/360,819.
Office Action dated Jan. 5, 2009 in U.S. Appl. No. 11/038,340.
Office Action dated Jan. 7, 2009 in U.S. Appl. No. 11/157,365.
Office Action dated Jan. 23, 2009 in U.S. Appl. No. 11/077,765.
Office Action dated Jan. 29, 2009, in U.S. Appl. No. 11/360,252.
Office Action dated Apr. 28, 2009 in U.S. Appl. No. 11/077,740.
Office Action dated May 19, 2009 in U.S. Appl. No. 11/038,340.
Office Action dated May 26, 2009 in U.S. Appl. No. 11/077,759.
Office Action dated Jun. 11, 2009 in U.S. Appl. No. 10/633,329.
Office Action dated Jun. 11, 2009 in U.S. Appl. No. 10/633,367.
Office Action dated Jun. 23, 2009 in U.S. Appl. No. 10/648,849.
Office Action dated Jul. 7, 2009 in U.S. Appl. No. 12/102,729.
Office Action dated Jul. 21, 2009 in U.S. Appl. No. 11/077,739.
Office Action dated Jul. 21, 2009 in U.S. Appl. No. 11/157,365.
Office Action dated Jul. 23, 2009, in U.S. Appl. No. 11/360,252.
Official Communication in European App. No. 04813418.3, dated Dec. 1, 2008.
Armour et al. Dec. 1990. Application of Chronic Intravascular Blood Glucose Sensor in Dogs. Diabetes 39:1519-1526.
Aussedat et al. 1997. A user-friendly method for calibrating a subcutaneous glucose sensor-based hypoglycaemic alarm. Biosensors & Bioelectronics 12(11):1061-1071.
Bland et al. 1986. Statistical methods for assessing agreement between two methods of clinical measurement. Lancet 1:307-310.
Bremer et al. 1999. Is blood glucose predictable from previous values? A solicitation for data. Diabetes 48:445-451.
Clarke et al. Sep.-Oct. 1987. Evaluating Clinical Accuracy of Systems for Self-Monitoring of Blood Glucose. Diabetes Care 10(5):622-628.
Csöregi et al. 1994. Amperometric microbiosensors for detection of hydrogen peroxide and glucose based on peroxidase-modified carbon fibers. Electroanalysis 6:925-933.
Guerci et al., Clinical performance of CGMS in type 1 diabetic patents treated by continuous subcutaneous insulin infusion using insulin analogs, Diabetes Care, 26:582-589, 2003.
Koschinsky et al. 1998. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.
Kurnik et al. 1999. Application of the mixtures of experts algorithm for signal processing in a noninvasive glucose monitoring system. Sensors and Actuators B, 60:19-26.
Martin, R. F. 2000. General Deming regression for estimating systematic bias and its confidence interval in method-comparison studies. Clinical Chemistry, 46(1):100-104.
Pickup et al. "In vivo molecular sensing in diabetes mellitus: an implantable glucose sensor with direct electron transfer," Diabetologia, 32:213-217 (1989).
Poitout et al. 1993. A glucose monitoring system for on line estimation in man of blood glucose concentration using a miniaturized glucose sensor implanted in the subcutaneous tissue and a wearable control unit. Diabetologia 36:658-663.
Rinken et al. 1998. Calibration of glucose biosensors by using pre-steady state kinetic data. Biosensors & Bioelectronics, 13:801-807.
Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.
Service et al. 1970. Mean amplitude of glycemic excursions, a measure of diabetic instability. Diabetes, 19: 644-655.
Sokol et al. 1980, Immobilized-enzyme rate-determination method for glucose analysis, Clin. Chem. 26(1):89-92.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Wagner et al. 1998. Continuous amperometric monitoring of glucose in a brittle diabetic chimpanzee with a miniature subcutaneous electrode. Proc. Natl. Acad. Sci. A, 95:6379-6382.
Ward et al. 1999. Assessment of chronically implanted subcutaneous glucose sensors in dogs: The effect of surrounding fluid masses. ASAIO Journal, 45:555-561.
Ward et al. 2000. Rise in background current over time in a subcutaneous glucose sensor in the rabbit: Relevance to calibration and accuracy. Biosensors & Bioelectronics, 15:53-61.
Zhu et al. 2002. Planar amperometric glucose sensor based on glucose oxidase immobilized by chitosan film on prussian blue layer. Sensors, 2:127-136.
Office Action dated Sep. 30, 2002 in U.S. Appl. No. 09/636,369.
Office Action dated Jul. 15, 2008 in U.S. Appl. No. 10/633,367.
Office Action dated Dec. 21, 2004 in U.S. Appl. No. 10/632,537.
Office Action dated Oct. 20, 2004 in U.S. Appl. No. 10/632,537.
Office Action dated Jun. 17, 2008 in U.S. Appl. No. 11/038,340.
Office Action dated May 29, 2008 in U.S. Reexam. No. 95/001,039.
Office Action dated Feb. 12, 2007 in U.S. Appl. No. 10/633,404.
Office Action dated Jun. 17, 2008 in U.S. Reexam. No. 95/001,038.
Office Action dated Jun. 12, 2008 in U.S. Appl. No. 10/633,329.
Office Action dated Feb. 4, 2008 in U.S. Appl. No. 10/633,329.
Office Action dated Jul. 30, 2007 in U.S. Appl. No. 10/633,329.
Office Action dated Mar. 26, 2007 in U.S. Appl. No. 10/633,329.
Office Action dated Oct. 5, 2006 in U.S. Appl. No. 10/633,329.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Sep. 19, 2008 in U.S. Appl. No. 11/077,765.
Office Action dated Jan. 10, 2008 in U.S. Appl. No. 11/077,714.
Office Action dated Jun. 26, 2008 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Jun. 30, 2008 in U.S. Appl. No. 11/360,252.
IPRP for PCT/US04/041095 filed Dec. 8, 2004.
ISR and WO for PCT/US04/041095 filed Dec. 8, 2004.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www. Answers.com/topic/xenogenic.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Baker et al. 1993. Dynamic concentration challenges for biosensor characterization. Biosensors & Bioelectronics 8:433-441.
Baker et al. 1996. Dynamic delay and maximal dynamic error in continuous biosensors. Anal Chem 68(8):1292-1297.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bindra et al. 1989. Pulsed amperometric detection of glucose in biological fluids at a surface-modified gold electrode. Anal Chem 61:2566-2570.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bolinder et al. 1992. Microdialysis measurement of the absolute glucose concentration in subcutaneous adipose tissue allowing glucose monitoring in diabetic patients. Diabetologia 35:1177-1180.
Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.
Bott, A. W. 1997. A Comparison of Cyclic Voltammetry and Cyclic Staircase Voltammetry Current Separations 16:1, 23-26.
Bott, A. 1998. Electrochemical methods for the determination of glucose. Current Separations 17(1):25-31.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Brunstein et al. 1989. Preparation and validation of implantable electrodes for the measurement of oxygen and glucose. Biomed Biochim. Acta 48(11/12):911-917.
Cai et al. 2004. A wireless, remote query glucose biosensor based on a pH-sensitive polymer. Anal Chem 76(4):4038-4043.
Cameron et al. 1997. Micromodular Implants to provide electrical stimulation of paralyzed muscles and limbs. IEEE Transactions on Biomedical Engineering 44(9):781-790.
Campanella et al. 1993. Biosensor for direct determination of glucose and lactate in undiluted biological fluids. Biosensors & Bioelectronics 8:307-314.
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chen et al. 2002. Defining the period of recovery of the glucose concentration after its local perturbation by the implantation of a miniature sensor. Clin. Chem. Lab. Med. 40:786-789.
Chia et al. 2004. Glucose sensors: toward closed loop insulin delivery. Endocrinol Metab Clin North Am 33:175-95.
Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioel.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-impintable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 1.
Danielsson et al. 1988. Enzyme thermistors, Methods in Enzymology, 137:181-197.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.

Deutsch et al., "Time series analysis and control of blood glucose levels in diabetic patients". Computer Methods and Programs in Biomedicine 41 (1994) 167-182.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8:121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ei-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fabietti et al. 2007. Clinical validation of a new control-oriented model of insulin and glucose dynamcs in subjects with type 1 diabetes, Diabetes Technology & Therapeutics, 9(4):327-338.
Fahy et al., An analysis: hyperglycemic intensive care patients need continuous glocuse monitoring—easier said than done, Journal of Diabetese Science and Technology, 2(2):201-204, Mar. 2008.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA® blood chemistry monitor for glucose in healthy and diabetic volunteers, Journal of Diabetese Science and Technology, 2(2):182-193, Mar. 2008.
Garg et al. 1999. Correlation of fingerstick blood glucose measurements with GlucoWatch biographer glucose results in young subjects with type 1 diabetes. Diabetes Care 22(10):1708-1714.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*
Heise et al. 2003. Hypoglycemia warning signal and glucose sensors: Requirements and concepts. Diabetes Technology & Therapeutics 5:563-571.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.

Jablecki et al. 2000. Simulations of the frequency response of implantable glucose sensors. Analytical Chemistry 72:1853-1859.
Jaremko et al. 1998. Advances toward the implantable artificial pancreas for treatment of diabetes. Diabetes Care 21(3):444-450.
Jensen et al. 1997. Fast wave forms for pulsed electrochemical detection of glucose by incorporation of reductive desorption of oxidation products. Analytical Chemistry 69(9):1776-1781.
Jeong et al. 2003. In vivo calibration of the subcutaneous amperometric glucose sensors using a non-enzyme electrode. Biosensors and Bioelectronics 19:313-319.
Jeutter, D. C. 1982. A transcutaneous implanted battery recharging and biotelemeter power switching system. IEEE Trans Biomed Eng 29:314-321.
Jeutter et al. 1993. Design of a radio-linked implantable cochlear prosthesis using surface acoustic wave devices. IEEE Transactions on ultrasonics, ferroelectrics and frequency control 40(5):469-477.
Johnson (1991). "Reproducible electrodeposition of biomolecules for the fabrication of miniature electroenzymatic biosensors," *Sensors and Actuators B*, 5:85-89.
Joung et al. 1998. An energy transmission system for an artificial heart using leakage inductance compensation of transcutaneous transformer. IEEE Transactions on Power Electronics 13(6):1013-1022.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kang et al. 2003. In vitro and short-term in vivo characteristics of a Kel-F thin film modified glucose sensor. Anal Sci 19:1481-1486.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Kerner, W. 2001. Implantable glucose sensors: Present status and future developments. Exp. Clin. Endocrinol. Diabetes 109(Suppl 2):S341-346.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Krouwer, J. S. 2002. Setting performance goals and evaluating total analytical error for diagnostic assays. Clinical Chemistry 48(6):919-927.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors&Beioelectronics, 9:491-500.
Kunjan et al., Automated blood sampling and glocuse sensing in critical care settings, Journal of Diabetes Science and Technology 2(3):194-200, Mar. 2008.
Kurtz et al. 2005. Recommendations for blood pressure measurement in humans and experimental animals, Part 2: Blood pressure measurement in experimental animals, A statement for professionals from the subcommittee of professional and public education of.
LaCourse et al. 1993. Optimization of waveforms for pulsed amperometric detection of carbohydrates based on pulsed voltammetry. Analytical Chemistry 65:50-52.
Ladd et al., Structure Determination by X-ray Crystallography, 3rd ed. Plenum, 1996, Ch. 1, pp. xxi-xxiv and 1-58.
Lehmann et al. May 1994. Retrospective valication of a physiological model of glucose-iunsulin interaaction in tyhpe 1 diabetes mellitus, Med. Eng. Phys. 16:193-202.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Anal. Chem. 56:2896-2904.
Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. *Diabetes Technology & Therapeutics*, 10(4): 257-265.
Lynch et al. 2001. Estimation-based model predictive control of blood glucose in type I diabetics: A simulation study. Proceedings of the IEEE 27th Annual Northeast Bioengineering Conference, pp. 79-80.
Lynn, P. A. 1971. Recursive digital filters for biological signals. Med. & Biol. Engng. 9:37-43.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Mancy et al. 1962. A galvanic cell oxygen analyzer. Journal of Electroanalytical Chemistry 4:65-92.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal* 7(12): 1507-1512.
Mastrototaro, J. J. 2000. The MiniMed continuous glucose monitoring system. Diabetes Technol Ther 2(Suppl 1):S13-8.
Mastrototaro et al. 2003. Reproducibility of the continuous glucose monitoring system matches previous reports and the intended use of the product. Diabetes Care 26:256; author reply p. 257.
Matsuki. 1994. Energy transfer system utilizing amorphous wires for implantable medical devices. IEEE Transactions on Magnetics 31(2):1276-1282.
Matsumoto et al. 1998. A micro-planar amperometeric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.
Memoli et al. 2002. A comparison between different immobilised glucoseoxidase-based electrodes. J Pharm Biomed Anal 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.
Metzger et al. Jul. 2002. Reproducibility of glucose measurements using the glucose sensor. Diabetes Care 25(6):1185-1191.
Meyerhoff et al. 1992. On line continuous monitoring of subcutaneous tissue glucose in men by combining portable glucosensor with microdialysis. Diabetologia 35:1087-1092.
Miller et al. 1993. Development of an autotuned transcutaneous energy transfer system ASAIO Journal 39:M706-M710.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al., Reduction of acetaminophen interference in glucose sensors by a composite Nafion membrane: demonstration in rats and man, Diabetologia 37(6):610-616, Jun. 1994.
Monsod et al. 2002. Do sensor glucose levels accurately predict plasma glucose concentrations during hypoglycemia and hyperinsulinemia? Diabetes Care 25(5):889-893.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Moussy et al. 1994. A miniaturized Nafion-based glucose sensor: In vitro and in vivo evaluation in dogs. Int. J. Artif. Organs 17(2):88-94.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Neuburger et al. 1987. Pulsed amperometric detection of carbohydrates at gold electrodes with a two-step potential waveform. Anal. Chem. 59:150-154.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panteleon et al. 2003. The role of the independent variable to glucose sensor calibration. Diabetes Technology & Therapeutics 5(3):401-410.
Parker et al. 1999. A model-based algorithm for blood glucose control in type I diabetic patients. IEEE Trans. Biomed. Eng. 46(2):148-157.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358: 2117-2126.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Phillps. 1995. A high capacity transcutaneous energy transmission system. ASAIO Journal 41:M259-M262.
Pichert et al. 2000. Issues for the coming age of continuous glucose monitoring Diabetes Educ 26(6):969-980.
Pickup et al. 1989. Potentially-implantable, amperometric glucose sensors with mediated electron transfer: improving the operating stability. Biosensors 4:109-119.
Pickup et al. 1993. Responses and Calibration of Amperometric Glucose Sensors Implanted in the Subcutaneous Tissue of Man. ACTA Diabetol, pp. 143-148.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pitzer et al. 2001. Detection of hypoglycemia with the GlucoWatch biographer. Diabetes Care 24(5):881-885.
Poirier et al. 1998. Clinical and statistical evaluation of self-monitoring blood glucose meters. Diabetes Care 21(11):1919-1924.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. 1992. Subcutaenous glucose monitoring by means of electrochemical sensors: fiction or reality? J. Biomed. Eng. 14:33-40.
Rebrin et al. 1999. Subcutaneous glucose predicts plasma glucose independent of insulin: Implications for continuous monitoring. Am. J. Physiol. 277:E561-71.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assitance improves glycemic control and glucose stability in pump-treated patients. Diab. Thechnol. & Therapeut., 10:194-199.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1992. Calibration of a wearable glucose sensor. The International Journal of Artificial Organs 15(1):55-61.
Schmidt et al. 1993. Glucose concentration in subcutaneous extracellular space. Diabetes Care 16(5):695-700.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1987. Measurements of glucose control. Diabetes Care, 10: 225-237.
Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Smith et al. 1998. An externally powered, multichannel, implantable stimulator-telemeter for control of paralyzed muscle. IEEE Transactions on Biomedical Engineering 45(4):463-475.
Sokolov et al. 1995. Metrological opportunities of the dynamic mode of operating an enzyme amperometric biosensor. Med. Eng. Phys. 17(6):471-476.
Sproule et al. 2002. Fuzzy pharmacology: Theory and applications. Trends in Pharmacological Sciences, 23(9):412-417.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1996. Does fall in tissue glucose precede fall in blood glucose? Diabetologia 39:609-612.
Street et al. 1988. A note on computing robust regression estimates via iteratively reweighted least squares. The American Statistician 42(2):152-154.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tamura, T. et al. 2000. Preliminary study of continuous glucose monitoring with a microdialysis technique and a null method—a numerical analysis. Frontiers Med. Biol. Engng. 10(2):147-156.
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995.—Abstract—Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Tilbury et al. 2000. Receiver operating characteristic analysis for intelligent medical systems—A new approach for finding confidence intervals. IEEE Transactions on Biomedical Engineering 47(7):952-963.
Torjman et al., Glucose monitoring in acute care: technologies on the horizon, Journal of Deabetes Science and Technology, 2(2):178-181, Mar. 2008.
Trajanoski et al. 1998. Neural predictive controller for insulin delivery using the subcutaneous route. IEEE Transactions on Biomedical Engineering 45(9):1122-1134.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Unger et al. 2004. Glucose control in the hospitalized patient. Emerg Med 36(9):12-18.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Valdes et al. 2000. In vitro and in vivo degradation of glucose oxidase enzyme used for an implantable glucose biosensor. Diabetes Technol. Ther. 2:367-376.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).

Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zavalkoff et al. 2002. Evaluation of conventional blood glucose monitoring as an indicator of integrated glucose values using a continuous subcutaneous sensor. Diabetes Care 25(9):1603-1606.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt+Ir electrodes in physiological buffer and its applicability to $H_2O_2$-based biosensors. *J. Electroanal. Chem.*, 345:253-271.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2O_2$ electrode." *Biosensors & Bioelectronics*, 9: 295-300.
Ziaie et al. 1997. A single-channel implantable microstimulator for functional neuromuscular stimulation. IEEE Transactions on Biomedical Engineering 44(10):909-920.
Office Action dated Jul. 30, 2009 in U.S. Appl. No. 12/102,654.
Office Action dated Mar. 10, 2010 in U.S. Appl. No. 12/102,654.
Office Action dated Nov. 9, 2009 in U.S. Appl. No. 11/038,340.
Office Action mailed Jun. 5, 2008 in U.S. Appl. No. 10/838,909.
Office Action mailed Mar. 16, 2009 in U.S. Appl. No. 10/838,909.
Office Action dated Dec. 29, 2009 in U.S. Appl. No. 11/077,739.
Office Action dated Mar. 1, 2010 in U.S. Appl. No. 11/077,739.
Office Action dated Feb. 3, 2010 in U.S. Appl. No. 11/077,765.
Office Action dated Jan. 21, 2010 in U.S. Appl. No. 11/157,365.
Office Action dated Aug. 25, 2009 in U.S. Appl. No. 11/334,876.
Office Action dated Apr. 7, 2010 in U.S. Appl. No. 11/360,819.
Assolant-Vinet et al. 1986. New Immoblized Enzyme Membranes for Tailor-Made Biosensors, Anal Letters 19(7&8): 875-885.
Bardeletti et al. 1986. A Reliable L-Lactate Electrode with a New Membrane for Enzyme Immobilization for Amperometric Assay of Lactate. Analyt Chim Acta, 187: 47-54.
Bertrand et al. 1981. Multipurpose Electrode with Different Enzyme Systems Bound to Collagen Films. Anal Chim Acta 126: 23-34.
Clarke et al. Oct. 2005. Evaluating the Clinical Accuracy of Two Continuous Glucose Sensors Using Continuous Glucose-Error Grid Analysis, Diabetes Care, 28(10) 2412-2417.
Coulet et al. (1981) Enzymes immobilized on collagen membranes: A tool for fundamental research and enzyme engineering. J Chromatography 215: 65-72.
Coulet, P.R. 1992. Polymeric membranes and coupled enzymes in the design of biosensors. J Membr Science 68: 217-228.
Gough. (May 2001) The implantable glucose sensor: An example of bioengineering design. Introduction to Bioengineering, Chapter 3, pp. 57-66.
Kamath et al. 2009. Analysis of time lags and other sources of error of the DexCom SEVEN continous glucose monitor. Diab Tech Thera. 11(11): 689-695.
Peguin et al. 1989. Pyruvate Oxidase and Oxaloacetate Decarbozylase Enzyme Electrodes—Simultaneous Determination of Transaminases with a Two-electrode-based Analyzer, Anal Chim Acta 222: 83-93.
Schaffar, Bernhard P.H. (Dec. 2001). Thick film biosensors for metabolites in undiluted whole blood and plasma samples, Anal Bioanal Chem. 372: 254-260.
Smith et al. 1991. A Comparison of Islet Transplantation and Subcutaneous Insulin Injections for the Treatment of Diabetes Mellitus, Comput Biol Med. 21(6): 417-427.
Sternberg et al. 1988. Covalent enzyme coupling on cellulose acetate membranes for glucose sensor development. Anal. Chem. 60: 2781-2786.
Street et al. Dec. 2004. Islet Graft Assessment in the Edmonton Protocol: Implications for Predicting Long-Term Clinical Outcome, Diabetes, 53: 3107-3114.
Takatsu et al. 1987. Solid State Biosensors Using Thin-Film Electrodes. Sens Actuators 11: 309-317.
Wang, J. "Electrochemical Glucose Biosensors" American Chemical Society, Chemical Reviews, Published on Web Dec. 23, 2007, p. est. 11.1, pp. 1-12; 10.1021/cr068123a.
Wolpert, Howard. Mar. 2008. Establishing a continuous glucose monitoring program. J Diab Scie Tech., 2(2): 307-310.
Yang et al. 1995. Glucose Biosensors with enzyme entrapped in polymer coating, Biomed Instrum Technol. 29(2): 125-133.
Office Action dated Jul. 29, 2010 in U.S. Appl. No. 12/364,786.
Office Action dated Oct. 29, 2009 in U.S. Appl. No. 11/360,819.
Office Action dated Sep. 2, 2010 in U.S. Appl. No. 11/360,819.
ISR dated Jan. 16, 2002 for PCT/US01/23850 filed Jul. 30, 2001.
IPER dated Jun. 4, 2003 for PCT/US01/23850 filed Jul. 30, 2001.
ISR and WO dated Nov. 29, 2004 for PCT/US04/24263, filed Jul. 27, 2004.
ISR and WO dated Oct. 7, 2008 for PCT/US08/66600, filed Jun. 11, 2008.
IPRP dated Dec. 17, 2009 for PCT/US08/66600, filed Jun. 11, 2008.
ISR and WO dated Jul. 20, 2007 for PCT/US06/24132 filed Jun. 20, 2006.
IPRP dated Dec. 24, 2007 for PCT/US06/24132, filed Jun. 20, 2006.
IPRP dated Feb. 6, 2006 for PCT/US04/24263, filed Jul. 27, 2004.
ISR and WO dated Nov. 4, 2005 for PCT/US05/024993 filed Jul. 13, 2005.
IPRP dated Jan. 16, 2007 for PCT/US05/024993 filed Jul. 13, 2005.
ISR and WO dated Jan. 9, 2006 for PCT/US04/38724 filed Nov. 17, 2004.
IPRP dated Mar. 5, 2009 for PCT/US04/38724 filed Nov. 17, 2004.
ISR and WO for PCT/US06/034284, filed Sep. 1, 2006.
IPRP for PCT/US06/034284, filed Sep. 1, 2006.
ISR and WO dated Aug. 8, 2008 for PCT/US08/058158, filed Mar. 25, 2008.
IPRP dated Sep. 29, 2009 for PCT/US08/058158, filed Mar. 25, 2008.
EPO Communication dated Aug. 3, 2010 for EP 10163675.1, Filed Feb. 24, 2005.

EPO Communication dated Mar. 17, 2011 for EP 10163675.1, filed Feb. 24, 2005.
EPO Communication dated Aug. 19, 2009 in European App. No. 05771646.6, filed Jul. 13, 2005.
EPO Communication dated Aug. 17, 2011 in European App. No. 05771646.6, filed Jul. 13, 2005.
Japanese Office Action dated Aug. 31, 2010 for Application No. 2006-522016, filed Jul. 27, 2004.
JIPO Office Action dated Jun. 28, 2011 for JP Application No. 2006-522016, filed Jul. 27, 2004.
Electronic File History for U.S. Appl. No. 12/545,180, filed Sep. 23, 2009 containing Office Action dated Dec. 9, 2011 as of Dec. 22, 2011.
Electronic File History for U.S. Appl. No. 12/565,166, filed Sep. 23, 2009 containing Office Action dated Dec. 12, 2011 as of Dec. 22, 2011.
Electronic File History for U.S. Appl. No. 12/565,199, filed Sep. 23, 2009 containing Office Action(s) dated Nov. 14, 2011 and Dec. 131, 2011 as of Dec. 22, 2011.
Electronic File History for U.S. Appl. No. 12/577,668, filed Oct. 12, 2009 containing Office Action dated Nov. 28, 2011 as of Dec. 22, 2011.
Electronic File History for U.S. Appl. No. 12/577,691, filed Oct. 12, 2009 containing Office Action dated Nov. 25, 2011 as of Dec. 22, 2011.
Electronic File History for U.S. Appl. No. 12/253,064, filed Oct. 16, 2008 containing Office Actions dated Sep. 6, 2011 and Dec. 13, 2011 and Applicant(s) Response filed Dec. 7, 2011 as of Dec. 22, 2011.
Electronic File History for U.S. Appl. No. 12/424,403, filed Apr. 15, 2009 containing Office Action dated Dec. 9, 2011 and Applicants Response filed Oct. 9, 2009 as of Dec. 22, 2011.
Electronic File History of U.S. Appl. No. 12/098,353, filed Apr. 4, 2008 containing Office Action(s) dated Aug. 26, 2010 and May 4, 2011 and Applicant Respons(es) filed Nov. 24, 2010 and Jun. 3, 2011 as of Jun. 3, 2011.
Electronic File History of U.S. Appl. No. 12/579,385, filed Oct. 14, 2009 containing Office Action(s) dated Aug. 23, 2010, Feb. 17, 2011 and Jul. 14, 2011 and Applicant(s) Response(s) filed Nov. 16, 2010, Apr. 18, 2011 and Jul. 25, 2011 as of Jul. 25, 2011.
Electronic File History of U.S. Appl. No. 12/536,852, filed Aug. 6, 2009 (now U.S. Patent No. 7,976,492 issued Jul. 12, 2011) containing Office Action(s) dated Jun. 25, 2010, Oct. 18, 2010, and Feb. 25, 2011 and Applicant(s) Response(s) filed Aug. 3, 2010, Dec. 8, 2010, and May 11, 2011.
Electronic File History of U.S. Appl. No. 12/133,738, filed Jun. 5, 2008 containing Office Action(s) dated Aug. 23, 2010, Sep. 10, 2010 and Feb. 14, 2011 and Applicant(s) Response(s) filed Aug. 31, 2010, Dec. 7, 2010 and May 16, 2011 as of May 18, 2011.
Electronic File History of U.S. Appl. No. 12/133,761, filed Jun. 5, 2008 containing Office Action(s) dated Aug. 23, 2010, Sep. 7, 2010 and Feb. 14, 2011 and Applicant Response(s) filed Aug. 25, 2010, Dec. 6, 2010, Apr. 14, 2011 and May 16, 2011 as of May 19, 2011.
Electronic File History of U.S. Appl. No. 12/133,786, filed Jun. 5, 2008 containing Office Action(s) dated Aug. 23, 2010, Sep. 8, 2010 and Feb. 14, 2011 and Applicant Response(s) filed Aug. 25, 2010, Dec. 7, 2010, Apr. 13, 2011 and May 13, 2011 as of May 19, 2011.
Electronic File History for U.S. Appl. No. 11/007,920, filed Dec. 8, 2004 containing Office Action(s) dated Jun. 24, 2008, Dec. 19, 2008, Mar. 27, 2009, Jul. 27, 2009, Apr. 2, 2010, Dec. 27, 2010, Jun. 2, 2011 and Nov. 23, 2011 and Applicant(s) Response(s) filed Oct. 30, 2007, Sep. 24, 2008, Jan. 15, 2009, Apr. 15, 2009, Aug. 10, 2009, Dec. 22, 2009, May 26, 2010, Mar. 25, 2011 and Aug. 1, 2011 as of Dec. 22, 2011.
Office Action dated Oct. 6, 2011 in U.S. Appl. No. 11/734,184, filed Apr. 11, 2007.
Response filed Mar. 6, 2012 in U.S. Appl. No. 11/734,184, filed Apr. 11, 2007.
US 7,530,950, 05/2009, Brister et al. (withdrawn)

* cited by examiner

SIGNAL PROCESSING FOR CONTINUOUS ANALYTE SENSOR

RELATED APPLICATION

This application is a continuation of U.S. application Ser. No. 11/007,920, filed Dec. 8, 2004, which claims the benefit of U.S. Provisional Application No. 60/528,382, filed Dec. 9, 2003, U.S. Provisional Application No. 60/587,787, filed Jul. 13, 2004, and U.S. Provisional Application No. 60/614,683, filed Sep. 30, 2004. Each above-referenced application is hereby incorporated by reference herein in its entirety.

FIELD OF THE INVENTION

The present invention relates generally to systems and methods for measuring and analyzing data obtained from a continuous analyte sensor. More particularly, the present invention relates to dynamic and intelligent estimation of analyte values from a continuous analyte sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically comprises uncomfortable finger pricking methods. Due to the lack of comfort and convenience, a person with diabetes will normally only measure his or her glucose levels two to four times per day. Unfortunately, these time intervals are so far apart that the person with diabetes will likely find out too late, sometimes incurring dangerous side effects, of a hyper- or hypo-glycemic condition. In fact, it is not only unlikely that a person with diabetes will take a timely SMBG value, but the person with diabetes will not know if their blood glucose value is going up (higher) or down (lower) based on conventional methods, inhibiting their ability to make educated insulin therapy decisions.

Some attempts have been made to continuously measure the glucose concentration in a person with diabetes. Typically, these continuous glucose sensors have required a reference glucose monitor (for example, SMBG) to provide reference glucose values in order to calibrate and/or interpret data from the continuous glucose monitor. While the use of these reference glucose values can be helpful, they can also cause numerous inconsistencies and instabilities in the data output of the continuous glucose sensor. As one example, a time lag can be caused by an interstitial fluid sample measured by an implantable glucose sensor as compared with a blood sample measured by an external reference glucose monitor, which can cause inaccurate calibration, outlier detection, and data output. Additionally, the static use of algorithms may not adequately represent physiological trends in a human, for example.

SUMMARY OF THE INVENTION

There exists a need for improvements in data processing of continuous glucose sensors in order to better handle the inconsistencies and instabilities that occur in glucose measurements and associated data analysis.

Accordingly, in a first embodiment, a method for estimating an analyte value from a continuous analyte sensor is provided, the method comprising receiving a data stream from the continuous analyte sensor for a first time period, thereby obtaining a measured analyte value; estimating at least one analyte value for a second time period based on the data stream; and comparing the estimated analyte value with the measured analyte value.

In an aspect of the first embodiment, the step of receiving a data stream comprises receiving a data stream that has been algorithmically smoothed.

In an aspect of the first embodiment, the step of receiving the data stream comprises receiving a raw data stream.

In an aspect of the first embodiment, the step of estimating at least one analyte value further comprises selecting an algorithm from a plurality of algorithms based on an analysis of the data stream prior to estimating at least one analyte value.

In an aspect of the first embodiment, the step of selecting an algorithm is conditional upon at least one value selected from the group consisting of analyte concentration, rate of change, acceleration, and an individual historical pattern of the data stream.

In an aspect of the first embodiment, the step of selecting an algorithm comprises employing the plurality of algorithms on the data stream and determining which of the plurality of algorithms best correlates with the data stream.

In an aspect of the first embodiment, the algorithm is selected from the group consisting of polynomial regression, autoregressive algorithms, Fourier transform, Wavelet transform, neural network-based mapping, fuzzy logic based pattern matching, and Genetic-Algorithms based pattern matching.

In an aspect of the first embodiment, the step of selecting an algorithm further comprises applying a physiological boundary to the selected algorithm.

In an aspect of the first embodiment, the method further comprises evaluating the selected algorithm by applying an evaluation function prior to employing the selected algorithm to estimate the analyte value, wherein the evaluation function is selected from the group consisting of a data association function, a curvature formula, and a physiological boundary.

In an aspect of the first embodiment, the step of analyzing a variation comprises analyzing a variation of the estimated analyte value based on a parameter selected from a statistical parameter, a clinical parameter, or a physiological parameter.

In an aspect of the first embodiment, the step of analyzing a variation comprises determining a physiological variation from the estimated analyte value.

In an aspect of the first embodiment, the step of analyzing a variation comprises determining a statistical variation from the estimated analyte value based on a statistical parameter.

In an aspect of the first embodiment, the step of comparing comprises determining a deviation between the estimated analyte value and the measured analyte value.

In an aspect of the first embodiment, the step of analyzing a variation comprises analyzing a variation of the estimated analyte value based on the deviation determined by the step of comparing.

In an aspect of the first embodiment, the method further comprises a step of recognizing a pattern by monitoring a physiological parameter over time.

In an aspect of the first embodiment, the step of analyzing a variation comprises analyzing a variation in the physiological parameter to determine a variation of the estimated analyte value.

In an aspect of the first embodiment, the step of analyzing a variation comprises determining a variation of the estimated analyte value based on a clinical risk of the estimated analyte value to the user.

In an aspect of the first embodiment, the method further comprises providing output based on the estimated analyte data.

In an aspect of the first embodiment, the output displays an estimated analyte value to the user.

In an aspect of the first embodiment, the output displays an estimated path of analyte values for a future time period.

In an aspect of the first embodiment, the output displays an estimated analyte value at a future point in time.

In an aspect of the first embodiment, the output displays an estimated future time period of clinical risk.

In an aspect of the first embodiment, the time period of clinical risk is determined when an estimated analyte value falls outside of a normal analyte threshold.

In an aspect of the first embodiment, the analyte is blood glucose and the normal analyte threshold is from about 100 mg/dL to about 160 mg/dL.

In an aspect of the first embodiment, the normal analyte threshold is from about 80 mg/dL to about 200 mg/dL.

In an aspect of the first embodiment, the normal analyte threshold is from about 55 mg/dL to about 220 mg/dL.

In an aspect of the first embodiment, the output displays at least one clinically acceptable target analyte value.

In an aspect of the first embodiment, the target analyte value is customizable by the user.

In an aspect of the first embodiment, the target analyte value is based on an individual physiological pattern.

In an aspect of the first embodiment, a parameter utilized in determining a therapy recommendation is customizable by the user.

In an aspect of the first embodiment, the output comprises an icon that has a shape representative of the analyzed variation of the estimated analyte value.

In an aspect of the first embodiment, the output comprises a dynamic visual representation of the analyzed variation of estimated analyte value.

In an aspect of the first embodiment, the output prompts the user to obtain a reference analyte value.

In an aspect of the first embodiment, the output provides at least one alarm selected from the group consisting of a visual alarm, an audible alarm, and a tactile alarm, wherein the alarm is provided based on a clinical risk associated with the estimated analyte value.

In an aspect of the first embodiment, the alarm is based on at least one parameter selected from the group consisting of an analyte value, a rate of change, acceleration of a rate of change, and an individual physiological pattern.

In an aspect of the first embodiment, the output continuously provides estimated analyte values.

In an aspect of the first embodiment, the output selectively provides the estimated analyte value based on an event trigger.

In an aspect of the first embodiment, the output provides a clinical risk zone that is displayed on a screen.

In an aspect of the first embodiment, the clinical risk zone comprises at least one of a shaded region, a colored region, and a patterned region.

In an aspect of the first embodiment, the clinical risk zone is bounded by a threshold.

In an aspect of the first embodiment, the output provides the estimated analyte value and the variation of the estimated analyte value on a trend graph.

In an aspect of the first embodiment, the output provides the estimated analyte value and the variation of the estimated analyte value on a gradient bar.

In an aspect of the first embodiment, the output is sent to a personal computer.

In an aspect of the first embodiment, the output is sent to a modem.

In an aspect of the first embodiment, the output is sent to an insulin pen.

In an aspect of the first embodiment, the output is sent to an insulin pump.

In a second embodiment, a method for estimating an analyte value from a continuous analyte sensor is provided, the method comprising receiving a data stream from the continuous analyte sensor for a time period; estimating at least one analyte value for a future time based on the data stream; analyzing a variation of the estimated analyte value based on a parameter selected from the group consisting of a statistical parameter, a clinical parameter, or a physiological parameter; and providing an output based on the estimated analyte value and the variation of the estimated analyte value.

In an aspect of the second embodiment, the method further comprises evaluating the selected algorithm by applying an evaluation function prior to employing the selected algorithm to estimate the analyte value, wherein the evaluation function is selected from the group consisting of a data association function, a curvature formula, and a physiological boundary.

In a third embodiment, a method for estimating an analyte value from a continuous analyte sensor is provided, the method comprising receiving a data stream from the continuous analyte sensor for a time period; selecting at least one algorithm from a plurality of algorithms based on an analysis of the data stream; evaluating the algorithm based on at least one parameter selected from the group consisting of a statistical parameter, a physiological parameter, and a clinical parameter; and employing the selected algorithm based on the step of evaluating to estimate at least one analyte value.

In an aspect of the third embodiment, the method further comprises evaluating the selected algorithm by applying an evaluation function prior to employing the selected algorithm to estimate the analyte value, wherein the evaluation function is selected from the group consisting of a data association function, a curvature formula, and a physiological boundary.

In an aspect of the third embodiment, the method further comprises analyzing a variation of the estimated analyte value based on a parameter selected from a statistical parameter, a clinical parameter, and a physiological parameter.

In an aspect of the third embodiment, the output further comprises a therapy recommendation to help the user obtain a target analyte value.

In a fourth embodiment, a method for matching a data pair using data from a continuous analyte sensor with data from a reference analyte source is provided, the method comprising receiving a data stream from the continuous analyte sensor, the data comprising at least one sensor data point; receiving reference data from a reference analyte monitor, the data comprising at least one reference data point; estimating at least one analyte value for a time period during which no data exists based on the data stream; and creating at least one matched data pair by matching the reference data to the analyte value.

In an aspect of the fourth embodiment, the step of receiving the data stream comprises receiving a data stream that has been algorithmically smoothed.

In an aspect of the fourth embodiment, the step of receiving reference data comprises downloading reference data via a cabled connection.

In an aspect of the fourth embodiment, the step of receiving reference data comprises downloading reference data via a wireless connection.

In an aspect of the fourth embodiment, the step of receiving reference data from a reference analyte monitor comprises receiving within a receiver an internal communication from a reference analyte monitor integral with the receiver.

In an aspect of the fourth embodiment, the algorithm is selected from the group consisting of polynomial regression, autoregressive algorithms, Fourier transform, Wavelet transform, neural network-based mapping, fuzzy logic based pattern matching, and Genetic-Algorithm matching.

In an aspect of the fourth embodiment, the method further comprises evaluating the selected algorithm by applying an evaluation function prior to employing the selected algorithm to estimate the analyte value, wherein the evaluation function is selected from the group consisting of a data association function, a curvature formula, and a physiological boundary.

In an aspect of the fourth embodiment, the method further comprises comparing the estimated analyte value with the corresponding measured analyte value to determine a time lag between the estimated analyte value and the corresponding measured analyte value.

In a fifth embodiment, a method for compensating for a time lag of continuous analyte sensor data by estimating an analyte value for a present time from which the continuous analyte sensor data is delayed is provided, the method comprising receiving a data stream from the continuous analyte sensor, wherein the data stream comprises a physiological time lag from the present time or a computational time lag from the present time; continuously estimating or periodically estimating analyte values for a present time period based on the data stream to compensate for the physiological time lag or the computational time lag in the analyte sensor data; and continuously providing or periodically providing an output to a user based on the estimated analyte values, such that the output of the estimated analyte values provides present time analyte values to the user.

In an aspect of the fifth embodiment, the analyte value estimation step further comprises selecting an algorithm from a plurality of algorithms based on analysis of the data stream prior to estimating the analyte values.

In an aspect of the fifth embodiment, the algorithm selection is conditional upon at least one value selected from the group consisting of analyte concentration, rate of change, acceleration, and an individual historical pattern of the data stream.

In an aspect of the fifth embodiment, the method further comprises evaluating the selected algorithm by applying a data association function, a curvature formula, or physiological boundaries prior to employing the selected algorithm to estimate analyte values.

In an aspect of the fifth embodiment, the method further comprises analyzing a variation of the estimated analyte values based on parameters selected from the group consisting of statistical parameters, clinical parameters, and physiological parameters.

In an aspect of the fifth embodiment, the step of analyzing a variation comprises determining a physiological variation from estimated analyte values.

In an aspect of the fifth embodiment, the step of analyzing a variation comprises determining a statistical variation from the estimated analyte values based on a statistical parameter.

In an aspect of the fifth embodiment, the method further comprises comparing the estimated analyte values with the measured analyte values to determine a deviation between the estimated analyte values and the measured analyte values.

In an aspect of the fifth embodiment, the step of analyzing a variation comprises analyzing a variation of the estimated analyte values based on the deviation determined by the step of comparing.

In an aspect of the fifth embodiment, the output displays estimated analyte values to the user.

In an aspect of the fifth embodiment, the output further comprises a therapy recommendation to help the user obtain a target analyte value.

In an aspect of the fifth embodiment, the output comprises an icon that has a shape representative of the analyzed variation of the estimated analyte value.

In a sixth embodiment, a method for estimating analyte values from a continuous analyte sensor is provided, the method comprising receiving a data stream from the continuous analyte sensor for a time period; and estimating one or more analyte values for a time period based on the data stream, wherein analyte estimation comprises performing an algorithm to estimate analyte values and applying physiological boundaries to the estimated analyte values.

In an aspect of the sixth embodiment, the analyte value estimation step further comprises selecting an algorithm from a plurality of algorithms based on analysis of the data stream prior to estimating the analyte values.

In an aspect of the sixth embodiment, the algorithm selection is conditional upon at least one of analyte concentration, rate of change, acceleration, and individual historical patterns of the data stream.

In an aspect of the sixth embodiment, the algorithm is selected from the group consisting of polynomial regression, autoregressive algorithms, Fourier transform, Wavelet transform, neural network-based mapping, fuzzy logic based pattern matching, and Genetic-Algorithm matching.

In an aspect of the sixth embodiment, the method further comprises evaluating the selected algorithm by applying a data association function, a curvature formula, or physiological boundaries prior to employing the selected algorithm to estimate analyte values.

In an aspect of the sixth embodiment, the method further comprises analyzing a variation of the estimated analyte values based on statistical, clinical, or physiological parameters.

In an aspect of the sixth embodiment, the time period of clinical risk is determined when an estimated analyte value falls outside of a normal analyte threshold.

In an aspect of the sixth embodiment, the output selectively provides estimated analytes value based on an event trigger.

In a seventh embodiment, a method for displaying analyte data from a continuous analyte sensor is provided, the method comprising receiving a data stream from the continuous analyte sensor for a time period; calibrating the data stream using a conversion function to determine at least one calibrated analyte value; analyzing a variation of at least one calibrated analyte value based on a parameter selected from the group consisting of a statistical parameter, a clinical parameter, and a physiological parameter; and providing an output based on the calibrated analyte value and the variation of the calibrated analyte value.

In an aspect of the seventh embodiment, the output comprises a numerical representation of a calibrated analyte value and a variation of the calibrated analyte value.

In an aspect of the seventh embodiment, the output comprises a numerical representation of a range of possible analyte values.

In an aspect of the seventh embodiment, the output further comprises an arrow representing a rate of change of the calibrated analyte values.

In an eighth embodiment, a system for estimating analyte data from a continuous analyte sensor is provided, the system comprising an input module operatively connected to the continuous analyte sensor that receives a data stream comprising a plurality of time spaced sensor data points from the analyte sensor; and a processor module comprising programming that estimates at least one analyte value for a time period based on the data stream and compares the estimated analyte value with a corresponding measured analyte value.

In an aspect of the eighth embodiment, the input module is adapted to receive a data stream that has been algorithmically smoothed.

In an aspect of the eighth embodiment, the input module is adapted to receive a raw data stream.

In an aspect of the eighth embodiment, the programming to estimate an analyte value further comprises programming to select an algorithm from a plurality of algorithms based on analysis of the data stream prior to estimating the analyte value.

In an aspect of the eighth embodiment, the processor module further comprises programming to select the algorithm conditional upon at least one parameter selected from the group consisting of an analyte concentration, a rate of change, acceleration of a rate of change, and an individual historical pattern of the data stream.

In an aspect of the eighth embodiment, the processor module runs the plurality of algorithms on the data stream and determines which of the plurality of algorithms best correlates with the data stream.

In an aspect of the eighth embodiment, the processor module comprises programming to apply a physiological boundary to the selected algorithm.

In an aspect of the eighth embodiment, the processor module further comprises programming to evaluate the selected algorithm by applying a data association function, a curvature formula, or physiological boundaries prior to employing the selected algorithm to estimate analyte values.

In an aspect of the eighth embodiment, the processor module further comprises programming to analyze a variation of the estimated analyte value based on a parameter selected from the group consisting of statistical parameters, clinical parameters, and physiological parameters.

In an aspect of the eighth embodiment, the programming to analyze a variation comprises determining a physiological variation from the estimated analyte value.

In an aspect of the eighth embodiment, the programming to analyze a variation comprises determining statistical variation from the estimated analyte value based on statistical parameters.

In an aspect of the eighth embodiment, the programming to compare the estimated analyte value with the measured analyte value further comprises determining a deviation between the estimated analyte value and the measured analyte value.

In an aspect of the eighth embodiment, the programming to analyze a variation comprising analyzing a variation of the estimated analyte values based on the deviation determined by the comparison step.

In an aspect of the eighth embodiment, the processor module further comprises programming to recognize a pattern by monitoring a physiological pattern over time.

In an aspect of the eighth embodiment, the programming to analyze a variation comprises analyzing the physiological pattern to determine a variation of the estimated analyte value.

In an aspect of the eighth embodiment, the programming to analyze a variation comprises determining the variation of the estimated analyte value based on a clinical risk of the estimated analyte value to the user.

In an aspect of the eighth embodiment, the system further comprises an output module comprising programming to output data based on the estimated analyte data.

In a ninth embodiment, a system for estimating analyte values from a continuous analyte sensor, the system comprising an input module operatively connected to the continuous analyte sensor that receives a data stream comprising a plurality of time spaced sensor data points from the analyte sensor; a processor module comprising programming that estimates at least one analyte value for a future time based on the data stream, and analyzes a variation of the estimated analyte value based on a parameter selected from the group consisting of a statistical parameter, a clinical parameter, and a physiological parameter; and an output module associated with the processor module and comprising programming to output analyte data based on at least one estimated analyte value and the variation of the estimated analyte value.

In an aspect of the ninth embodiment, the input module is adapted to receive a data stream that has been algorithmically smoothed.

In an aspect of the ninth embodiment, the input module is adapted to receive a raw data stream.

In an aspect of the ninth embodiment, the programming to estimate an analyte value further comprises programming to select an algorithm from a plurality of algorithms based on analysis of the data stream prior to estimating the analyte value.

In an aspect of the ninth embodiment, the programming to select an algorithm is conditional upon at least one parameter selected from the group consisting of an analyte concentration, a rate of change, an acceleration of a rate of change, and an individual historical pattern of the data stream.

In an aspect of the ninth embodiment, the programming to select an algorithm further comprises employing the plurality of algorithms on the data stream and determining which of the plurality of algorithms best correlates with the data stream.

In an aspect of the ninth embodiment, the algorithms are selected from the group consisting of polynomial regression, autoregressive algorithms, Fourier transform, Wavelet transform, neural network-based mapping, fuzzy logic based pattern matching, and Genetic-Algorithm matching.

In an aspect of the ninth embodiment, the processor module further comprises programming to apply a physiological boundary to the selected algorithm.

In an aspect of the ninth embodiment, the processor module further comprises programming to evaluate the selected algorithm by applying a data association function, a curvature formula, or physiological boundaries prior to employing the selected algorithm to estimate the analyte value.

In an aspect of the ninth embodiment, the programming to analyze a variation comprises determining a physiological variation from the estimated analyte value.

In an aspect of the ninth embodiment, the programming to analyze a variation comprises determining statistical variation from the estimated analyte value based on a statistical parameter.

In an aspect of the ninth embodiment, the processor module compares the estimated analyte value with the measured analyte value to determine a deviation between the estimated analyte value and the measured analyte value.

In an aspect of the ninth embodiment, the programming to analyze a variation comprises analyzing a variation of the estimated analyte value based on the deviation.

In an aspect of the ninth embodiment, the processor module further comprises programming to recognize a pattern by monitoring a physiological pattern over time.

In an aspect of the ninth embodiment, the programming to analyze a variation comprises analyzing the physiological pattern to determine a variation of the estimated analyte value.

In an aspect of the ninth embodiment, the programming to analyze a variation comprises determining the variation of the estimated analyte value based the clinical risk of the estimated analyte value to the user.

In an aspect of the ninth embodiment, the output displays estimated analyte value to the user.

In a tenth embodiment, a system for estimating analyte values from a continuous analyte sensor is provided, the system comprising an input module operatively connected to the continuous analyte sensor that receives a data stream comprising a plurality of time spaced sensor data points from the analyte sensor; and a processor module comprising programming that selects an algorithm from a plurality of algorithms based on an analysis of the data stream, that evaluates the algorithm based on a parameter selected from the group consisting of statistical parameters, physiological parameters, and clinical parameters, and that employs a selected algorithm based on the algorithm evaluation to estimate at least one analyte value.

In an eleventh embodiment, a system for matching data pairs from a continuous analyte sensor with data from a reference analyte source, the system comprising a sensor input module operatively connected to the continuous analyte sensor that receives a data stream comprising a plurality of time spaced sensor data points from the analyte sensor; a reference input module receiving reference data from a reference analyte monitor, including at least one reference data point; and a processor module comprising programming that estimates at least one analyte value for a time period during which no data exists based on the data stream and creates at least one matched data pair by matching reference analyte data to the estimated analyte value.

In a twelfth embodiment, a system for compensating for a time lag of continuous analyte sensor data by estimating an analyte value for a present time from which the continuous analyte sensor data is delayed is provided, the system comprising an input module operatively connected to the continuous analyte sensor that receives a data stream comprising a plurality of time spaced sensor data points from the analyte sensor; a processor module comprising programming that continuously estimates or periodically estimates analyte values for the present time period based on the data stream to compensate for the physiological or computational time lag in the analyte sensor data; and an output module associated with the processor module and comprising programming to continuously provide or periodically provide an output to the user based on the estimated analyte values, such that output of the estimated analyte values provides present time analyte values to the user.

In a thirteenth embodiment, a system for estimating analyte values from a continuous analyte sensor is provided, the system comprising an input module operatively connected to the continuous analyte sensor that receives a data stream comprising a plurality of time spaced sensor data points from the analyte sensor; and a processor module comprising programming that estimates at least one analyte value for a time period based on the data stream, wherein the analyte estimation comprises performing an algorithm to estimate an analyte value and applying a physiological boundary to the estimated analyte value.

In a fourteenth embodiment, a system for displaying analyte data from a continuous analyte sensor is provided, the system comprising an input module operatively connected to the continuous analyte sensor that receives a data stream comprising a plurality of time spaced sensor data points from the analyte sensor; a processor module comprising programming that calibrates the data stream using a conversion function to determine a calibrated analyte value and analyze a variation of the calibrated analyte value based on statistical, clinical, or physiological parameters; and an output module associated with the processor module and comprising programming to output data based on the calibrated analyte value and the variation of calibrated analyte value.

DETAILED DESCRIPTION OF CERTAIN EMBODIMENTS

Figure 1:
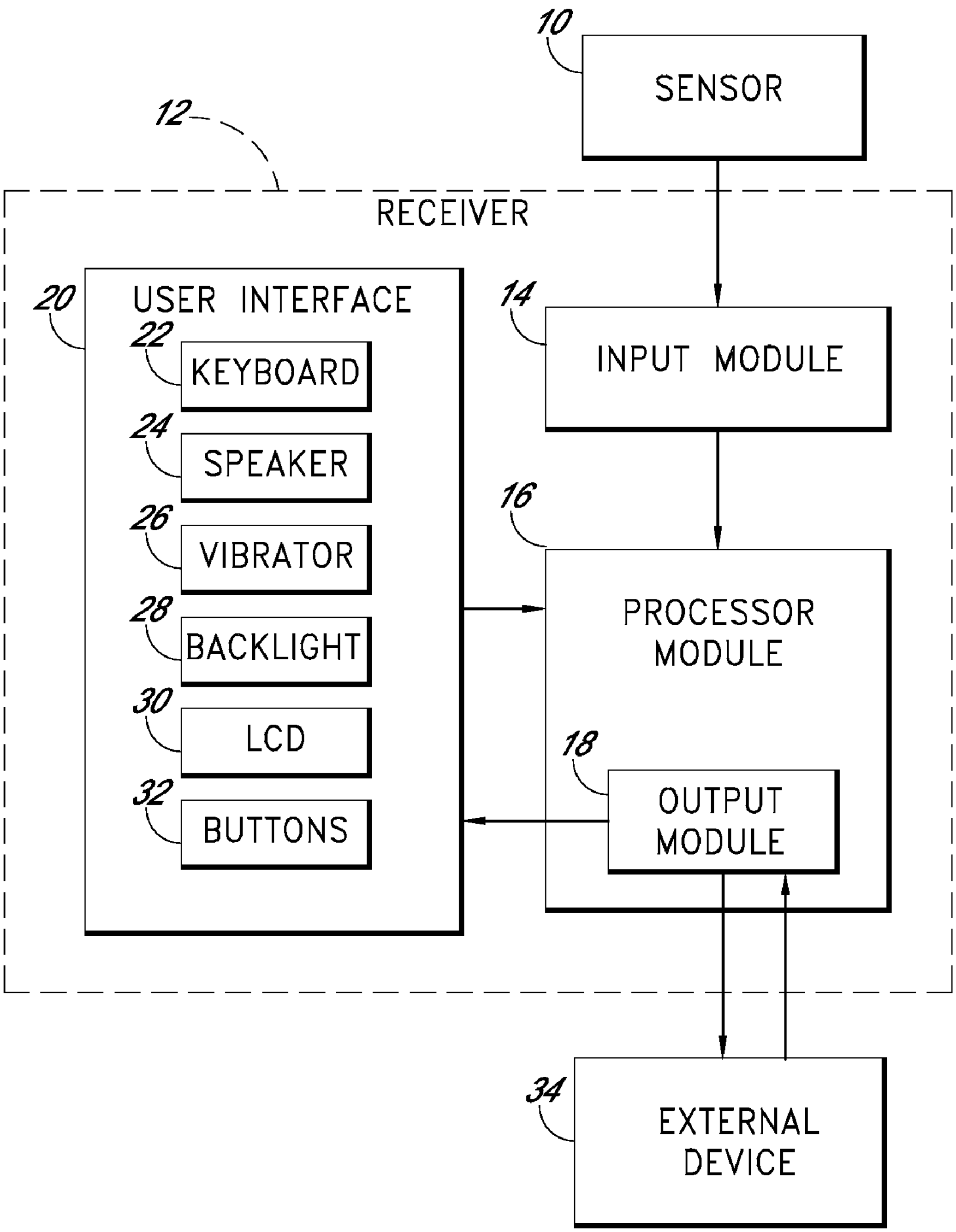
FIG. 1 is a block diagram that illustrates the configuration of the medical device in one embodiment, including a continuous analyte sensor, a receiver, and an external device.

The following description and examples illustrate some exemplary embodiments of the disclosed invention in detail.

Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "analyte," as used herein, is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica, enterovirus, Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum, poliovirus, Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous analyte sensor," as used herein, is a broad term and is used in its ordinary sense, including, but not limited to, a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte sensing," as used herein, is a broad term and is used in its ordinary sense, including, but not limited to, the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor," as used herein, are broad terms and are used in their ordinary sense, including, but not limited to, a device that measures a concentration of an analyte and can be used as a reference for the continuous analyte sensor, for example a self-monitoring blood glucose meter (SMBG) can be used as a reference for a continuous glucose sensor for comparison, calibration, or the like.

The term "biological sample," as used herein, is a broad term and is used in its ordinary sense, including, but not limited to, sample of a host body, for example, blood, interstitial fluid, spinal fluid, saliva, urine, tears, sweat, or the like.

The term "host," as used herein, is a broad term and is used in its ordinary sense, including, but not limited to, mammals such as humans.

The term "processor," as used herein, is a broad term and is used in its ordinary sense, including, but not limited to, a computer system, state machine, or the like that performs arithmetic and logic operations using logic circuitry that responds to and processes the basic instructions that drive a computer.

The term "ROM," as used herein, is a broad term and is used in its ordinary sense, including, but not limited to, read-only memory, which is a type of data storage device manufactured with fixed contents. ROM is broad enough to include EEPROM, for example, which is electrically erasable programmable read-only memory (ROM).

The term "RAM," as used herein, is a broad term and is used in its ordinary sense, including, but not limited to, a data storage device for which the order of access to different locations does not affect the speed of access. RAM is broad enough to include SRAM, for example, which is static random access memory that retains data bits in its memory as long as power is being supplied.

The term "A/D Converter," as used herein, is a broad term and is used in its ordinary sense, including, but not limited to, hardware and/or software that converts analog electrical signals into corresponding digital signals.

The term "RF transceiver," as used herein, is a broad term and is used in its ordinary sense, including, but not limited to, a radio frequency transmitter and/or receiver for transmitting and/or receiving signals.

The terms "raw data stream" and "data stream," as used herein, are broad terms and are used in their ordinary sense, including, but not limited to, an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The terms "calibrated data" and "calibrated data stream," as used herein, are broad terms, and are used in their ordinary sense, including, but not limited to, data that has been transformed from its raw state to another state using a function, for example a conversion function, to provide a meaningful value to a user. The terms "smoothed data" and "filtered data," as used herein, are broad terms and are used in their ordinary sense, including, but not limited to, data that has been modified to make it smoother and more continuous and/or to remove or diminish outlying points, for example, by performing a moving average of the raw data stream.

The term "counts," as used herein, is a broad term and is used in its ordinary sense, including, but not limited to, a unit of measurement of a digital signal. In one example, a raw data stream measured in counts is directly related to a voltage (for example, converted by an A/D converter), which is directly related to current from a working electrode.

The term "electronic circuitry," as used herein, is a broad term and is used in its ordinary sense, including, but not limited to, the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat," as used herein, is a broad term and is used in its ordinary sense, including, but not limited to, an electrical system that controls the potential between the working and reference electrodes of a two-electrode cell or three-electrode cell at a preset value. The potentiostat forces whatever current is necessary to flow between the working and counter electrodes to keep the desired potential, as long as the needed cell voltage and current do not exceed the compliance limits of the potentiostat.

The term "electrical potential," as used herein, is a broad term and is used in its ordinary sense, including, but not limited to, the electrical potential difference between two points in a circuit, which is the cause of the flow of a current.

The terms "operably connected" and "operably linked," as used herein, are broad terms and are used in their ordinary sense, including, but not limited to, one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "algorithm," as used herein, is a broad term and is used in its ordinary sense, including, but not limited to, the computational processes (for example, programs) involved in transforming information from one state to another, for example using computer processing.

The term "estimation algorithm," as used herein, is a broad term and is used in its ordinary sense, including, but not limited to, the processing involved in estimating analyte values from measured analyte values for a time period during which no data exists (e.g., for a future time period or during data gaps). This term is broad enough to include one or a plurality of algorithms and/or computations. This term is also broad enough to include algorithms or computations based on mathematical, statistical, clinical, and/or physiological information.

The term "regression," as used herein, is a broad term and is used in its ordinary sense, including, but not limited to, finding a line in which a set of data has a minimal measurement (for example, deviation) from that line. Regression can be linear, non-linear, first order, second order, and so forth. One example of regression is least squares regression.

The terms "recursive filter" and "auto-regressive algorithm," as used herein, are broad terms and are used in their ordinary sense, including, but not limited to, an equation in which includes previous averages are part of the next filtered output. More particularly, the generation of a series of observations whereby the value of each observation is partly dependent on the values of those that have immediately preceded it. One example is a regression structure in which lagged response values assume the role of the independent variables.

The terms "velocity" and "rate of change," as used herein, are broad terms and are used in their ordinary sense, including, but not limited to, time rate of change; the amount of change divided by the time required for the change. In one embodiment, these terms refer to the rate of increase or decrease in an analyte for a certain time period.

The term "acceleration" as used herein, is a broad term and is used in its ordinary sense, including, but not limited to, the rate of change of velocity with respect to time. This term is broad enough to include deceleration.

The term "variation," as used herein, is a broad term and is used in its ordinary sense, including, but not limited to, a divergence or amount of change from a point, line, or set of data. In one embodiment, estimated analyte values can have a variation including a range of values outside of the estimated analyte values that represent a range of possibilities based on known physiological patterns, for example.

The term "deviation," as used herein, is a broad term and is used in its ordinary sense, including, but not limited to, a statistical measure representing the difference between different data sets. The term is broad enough to encompass the deviation represented as a correlation of data.

The terms "statistical parameters" and "statistical," as used herein, are broad terms and are used in their ordinary sense, including, but not limited to, information computed from the values of a sampling of data. For example, noise or variability in data can be statistically measured.

The term "statistical variation," as used herein, is a broad term and is used in its ordinary sense, including, but not limited to, divergence or change from a point, line, or set of data based on statistical information. The term "statistical information" is broad enough to include patterns or data analysis resulting from experiments, published or unpublished, for example.

The term "clinical risk," as used herein, is a broad term and is used in its ordinary sense, including, but not limited to, an identified danger or potential risk to the health of a patient based on a measured or estimated analyte concentration, its rate of change, and/or its acceleration. In one exemplary embodiment, clinical risk is determined by a measured glucose concentration above or below a threshold (for example, 80-200 mg/dL) and/or its rate of change.

The term "clinically acceptable," as used herein, is a broad term and is used in its ordinary sense, including, but not limited to, an analyte concentration, rate of change, and/or acceleration associated with that measured analyte that is considered to be safe for a patient. In one exemplary embodiment, clinical acceptability is determined by a measured glucose concentration within a threshold (for example, 80-200 mg/dL) and/or its rate of change.

The terms "physiological parameters" and "physiological boundaries," as used herein, are broad terms and are used in their ordinary sense, including, but not limited to, the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/$min^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The terms "individual physiological patterns" and "individual historical patterns," as used herein, are broad terms and are used in their ordinary sense, including, but not limited to, patterns obtained by monitoring a physiological characteristic, such as glucose concentration, in a mammal over a time period. For example, continual or continuous monitoring of glucose concentration in humans can recognize a "normal" pattern of turnaround at the human's lowest glucose levels.

The term "physiological variation," as used herein, is a broad term and is used in its ordinary sense, including, but not limited to, divergence or change from a point, line, or set of data based on known physiological parameters and/or patterns.

The terms "data association" and "data association function," as used herein, are broad terms and are used in their ordinary sense, including, but not limited to, a statistical analysis of data and particularly its correlation to, or deviation from, a particular line. A data association function is used to show data association. For example, a measured glucose data stream as described herein can be analyzed mathematically to determine its correlation to, or deviation from, an estimated data stream for a corresponding time period; this correlation or deviation is the data association. Examples of data association functions include, but are not limited to, linear regression, non-linear mapping/regression, rank (for example, non-parametric) correlation, least mean square fit, mean absolute deviation (MAD), and/or mean absolute relative difference (MARD).

The terms "clinical error grid," "clinical error analysis" and "error grid analysis," as used herein, are broad terms and are used in their ordinary sense, including, but not limited to, an analysis method that assigns a specific level of clinical risk to an error between two time corresponding analyte measurements. Examples include Clarke Error Grid, Consensus Grid, mean absolute relative difference, rate grid, or other clinical cost functions.

The term "Clarke Error Grid," as used herein, is a broad term and is used in its ordinary sense, including, but not limited to, an error grid analysis, which evaluates the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose," Diabetes Care, Volume 10, Number 5, September-October 1987, which is incorporated by reference herein in its entirety.

The term "rate grid", as used herein, is a broad term and is used in its ordinary sense, including, without limitation, to refer to an error grid analysis, which evaluates the clinical significance of the difference between a reference glucose value and a continuous sensor generated glucose value, taking into account both single-point and rate-of-change values. One example of a rate grid is described in Kovatchev, B. P.; Gonder-Frederick, L. A.; Cox, D. J.; Clarke, W. L. Evaluating the accuracy of continuous glucose-monitoring sensors: continuous glucose-error grid analysis illustrated by TheraSense Freestyle Navigator data. *Diabetes Care* 2004, 27, 1922-1928.

The term "curvature formula," as used herein, is a broad term and is used in its ordinary sense, including, but not limited to, a mathematical formula that can be used to define a curvature of a line. Some examples of curvature formulas include Euler and Rodrigues' curvature formulas.

The term "time period," as used herein, is a broad term and is used in its ordinary sense, including, but not limited to, an amount of time including a single point in time and a path (for example, range of time) that extends from a first point in time to a second point in time.

The term "measured analyte values," as used herein, is a broad term and is used in its ordinary sense, including, but not limited to, an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "estimated analyte values," as used herein, is a broad term and is used in its ordinary sense, including, but not limited to, an analyte value or set of analyte values, which have been algorithmically extrapolated from measured analyte values. Typically, estimated analyte values are estimated for a time period during which no data exists. However, estimated analyte values can also be estimated during a time period for which measured data exists, but is to be replaced by algorithmically extrapolated data due to a time lag in the measured data, for example.

The term "alarm," as used herein, is a broad term and is used in its ordinary sense, including, but not limited to, audible, visual, or tactile signals that are triggered in response to detection of clinical risk to a patient. In one embodiment, hyperglycemic and hypoglycemic alarms are triggered when present or future clinical danger is assessed based on continuous analyte data.

The terms "target analyte values" and "analyte value goal," as used herein, are broad terms and are used in their ordinary sense, including, but not limited to, an analyte value or set of analyte values that are clinically acceptable. In one example, a target analyte value is visually or audibly presented to a patient in order to aid in guiding the patient in understanding how they should avoid a clinically risky analyte concentration.

The terms "therapy" and "therapy recommendations," as used herein, are broad terms and are used in their ordinary sense, including, but not limited to, the treatment of disease or disorder by any method. In one exemplary embodiment, a patient is prompted with therapy recommendations such as "inject insulin" or "consume carbohydrates" in order to avoid a clinically risky glucose concentration.

The terms "customize" and "customization," as used herein, are broad terms and are used in their ordinary sense, including, but not limited to, to make changes or specifications to a program so that it meets an individual's needs.

The term "computer," as used herein, is broad term and is used in its ordinary sense, including, but not limited to, machine that can be programmed to manipulate data.

The term "modem," as used herein, is a broad term and is used in its ordinary sense, including, but not limited to, an electronic device for converting between serial data from a computer and an audio signal suitable for transmission over a telecommunications connection to another modem.

The term "insulin pen," as used herein, is a broad term and is used in its ordinary sense, including, but not limited to, an insulin injection device generally the size of a pen that includes a needle and holds a vial of insulin. It can be used instead of syringes for giving insulin injections.

The term "insulin pump," as used herein, is a broad term and is used in its ordinary sense, including, but not limited to, a device that delivers a continuous supply of insulin into the body. The insulin flows from the pump through a plastic tube (called a catheter) that is connected to a needle inserted into the skin and taped in place, for example.

Overview

Certain embodiments provide a continuous analyte sensor that measures a concentration of analyte within a host and provides a data stream representative of the concentration of the analyte in the host, and a receiver that processes the data stream received from the analyte sensor for output as a meaningful value to a user or device. In some embodiments, the analyte sensor is integral with the receiver, while in other embodiments, the analyte sensor is operatively linked to the receiver, for example, via a wired link or a wireless link.

Data processing associated with various embodiments calculates estimated analyte values from measured analyte values that can be useful to 1) compensate for a time lag associated with the analyte concentration measured sensor as compared to a reference source, for example, 2) estimate approaching clinical risk and warn a patient or doctor in an effort to avoid the clinical risk, 3) ensure accurate calibration of sensor data with reference data by dynamically and intelligently matching reference data with corresponding sensor data, for example, 4) replace data during periods of high signal noise or inaccurate data, and/or 5) provide future estimated analyte values that encourage more timely proactive behavior by a patient. The systems and methods calculate estimated analyte values based on algorithms that dynamically and intelligently determine which estimative algorithm best fits the present data stream, for example, using first or second order regression, considering physiological boundaries, evaluating the estimative algorithm for data association, determining possible variations around the estimated analyte values due to statistical, clinical, or physiological considerations, and/or comparing the estimated analyte values with time corresponding measured analyte values.

Some embodiments further generate data output, which can be in the form of real-time output to a user on screen or other user interface, for example, on the receiver. Data output can include real-time measured analyte values, estimated analyte values, possible variations of estimated analyte values, targets or goals for analyte values, or the like. Additionally or alternatively, data output can be sent to a device external from the receiver, for example, a computer, modem, or medical device. In some embodiments, input from the user or from another device, such as insulin injections (time and amount), meal times, exercise, personalized therapy recommendations, or the like, can be input into the receiver and processed to provide more customized data analysis and/or data output.

Accordingly, the systems and methods calculate estimated analyte values in a timely, accurate, and reliable manner based on measured analyte values, which can be helpful for proactively caring for a patient's condition. Estimated analyte values can provide information useful in warning a patient of upcoming clinical risk. Additionally, targets and/or goals set for a patient's analyte values, based on present analyte conditions, and can be useful in proactively avoiding clinical risk. Furthermore, therapy recommendations can be provided that are useful in guiding a patient away from clinical risk.

Continuous Analyte Sensor

The systems and methods of the preferred embodiments provide an analyte sensor that measures a concentration of analyte of interest or a substance indicative of the concentration or presence of the analyte. The analyte sensor uses any known method, including invasive, minimally invasive, and non-invasive sensing techniques, to provide an output signal indicative of the concentration of the analyte of interest. In some embodiments, the analyte sensor is a continuous device, for example a subcutaneous, transdermal, or intravascular device. In some embodiments, the device can take a plurality of intermittent measurements. The analyte sensor can use any method of analyte-measurement, including enzymatic, chemical, physical, electrochemical, spectrophotometric, polarimetric, calorimetric, radiometric, or the like. Generally, the analyte sensor can be any sensor capable of determining the level of any analyte in the body, for example glucose, oxygen, lactase, hormones, cholesterol, medicaments, viruses, or the like. It should be understood that the devices and methods described herein can be applied to any device capable of continually or continuously detecting a concentration of analyte and providing an output signal that represents the concentration of that analyte.

In one preferred embodiment, the analyte sensor is an implantable glucose sensor, such as described with reference to U.S. Pat. No. 6,001,067 and co-pending U.S. patent application Ser. No. 10/633,367 entitled, "SYSTEM AND METHODS FOR PROCESSING ANALYTE SENSOR DATA," filed Aug. 1, 2003, which are incorporated herein by reference in their entirety. In another preferred embodiment, the analyte sensor is a transcutaneous glucose sensor, such as described with reference to U.S. Provisional Patent Application 60/587,787 and 60/614,683. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. All of the above patents are incorporated by reference herein in their entirety.

FIG. 1 is a block diagram that illustrates the configuration of the medical device in one embodiment, including a continuous analyte sensor, a receiver, and an external device. In general, the continuous analyte sensor 10 is any sensor configuration that provides an output signal indicative of a concentration of an analyte. The output signal is sent to a receiver 12 and received by an input module 14, which is described in more detail below. The output signal is typically a raw data stream that is used to provide a useful value of the measured analyte concentration to a patient or doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in co-pending U.S. patent application Ser. No. 10/632,537 entitled, "SYSTEMS AND METHODS FOR REPLACING SIGNAL ARTIFACTS IN A GLUCOSE SENSOR DATA STREAM, "filed Aug. 22, 2003, which is incorporated herein by reference in its entirety.

Receiver

Referring again to FIG. 1, the receiver 12, which is operatively linked to the sensor 10, receives a data stream from the sensor 10 via the input module 14. In one embodiment, the input module includes a quartz crystal operably connected to an RF transceiver (not shown) that together function to receive and synchronize data streams from the sensor 10. However, the input module 14 can be configured in any manner that is capable of receiving data from the sensor. Once received, the input module 14 sends the data stream to a processor 16 that processes the data stream, such as described in more detail below.

The processor 16 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware and software that performs the processing described herein, for example read-only memory (ROM) provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

An output module 18, which is integral with and/or operatively connected with the processor 16, includes programming for generating output based on the data stream received from the sensor 10 and its processing incurred in the processor 16. In some embodiments, output is generated via a user interface 20.

The user interface 20 comprises a keyboard 22, speaker 24, vibrator 26, backlight 28, liquid crystal display (LCD) screen 30, and one or more buttons 32. The components that comprise the user interface 20 include controls to allow interaction of the user with the receiver. The keyboard 22 can allow, for example, input of user information about himself/herself, such as mealtime, exercise, insulin administration, customized therapy recommendations, and reference analyte values. The speaker 24 can produce, for example, audible signals or alerts for conditions such as present and/or estimated hyper- and hypoglycemic conditions in a person with diabetes. The vibrator 26 can provide, for example, tactile signals or alerts for reasons such as described with reference to the speaker, above. The backlight 28 can be provided, for example, to aid the user in reading the LCD 30 in low light conditions. The LCD 30 can be provided, for example, to provide the user with visual data output, such as described in more detail below with reference to FIGS. 20 to 26, however other screen formats are possible. In some embodiments, the LCD is a touch-activated screen. The buttons 32 can provide for toggle, menu selection, option selection, mode selection, and reset, for example. In some alternative embodiments, a microphone can be provided to allow for voice-activated control.

In some embodiments, estimated analyte values, such as described, for example with reference to FIGS. 3 to 14, can be displayed on the LCD 30. In some embodiments, a variation of estimated analyte values, such as described, for example with reference to FIGS. 15 to 17, can be displayed on the LCD 30. In some embodiments, target analyte values, such as described, for example with reference to FIGS. 22 to 24, can be displayed on the LCD 30. In some embodiments, therapy recommendations, such as described in the preferred embodiments, for example with reference to FIG. 24, can be displayed on the screen 30.

In some embodiments, prompts or messages can be displayed on the user interface to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

Additionally, data output from the output module 18 can provide wired or wireless, one- or two-way communication between the receiver 12 and an external device 34. The external device 34 can be any device that wherein interfaces or communicates with the receiver 12. In some embodiments, the external device 34 is a computer, and the receiver 12 is able to download historical data for retrospective analysis by the physician, for example. In some embodiments, the external device 34 is a modem, and the receiver 12 is able to send alerts, warnings, emergency messages, or the like, via telecommunication lines to another party, such as a doctor or family member. In some embodiments, the external device 34 is an insulin pen, and the receiver 12 is able to communicate therapy recommendations, such as insulin amount and time to the insulin pen. In some embodiments, the external device 34 is an insulin pump, and the receiver 12 is able to communicate therapy recommendations, such as insulin amount and time to the insulin pump. The external device 34 can include other technology or medical devices, for example pacemakers, implanted analyte sensor patches, other infusion devices, telemetry devices, or the like.

The user interface 20 including keyboard 22, buttons 32, a microphone (not shown), and the external device 34 can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input, which can be helpful in data processing as will be understood by one skilled in the art.

Calibration

Figure 2:
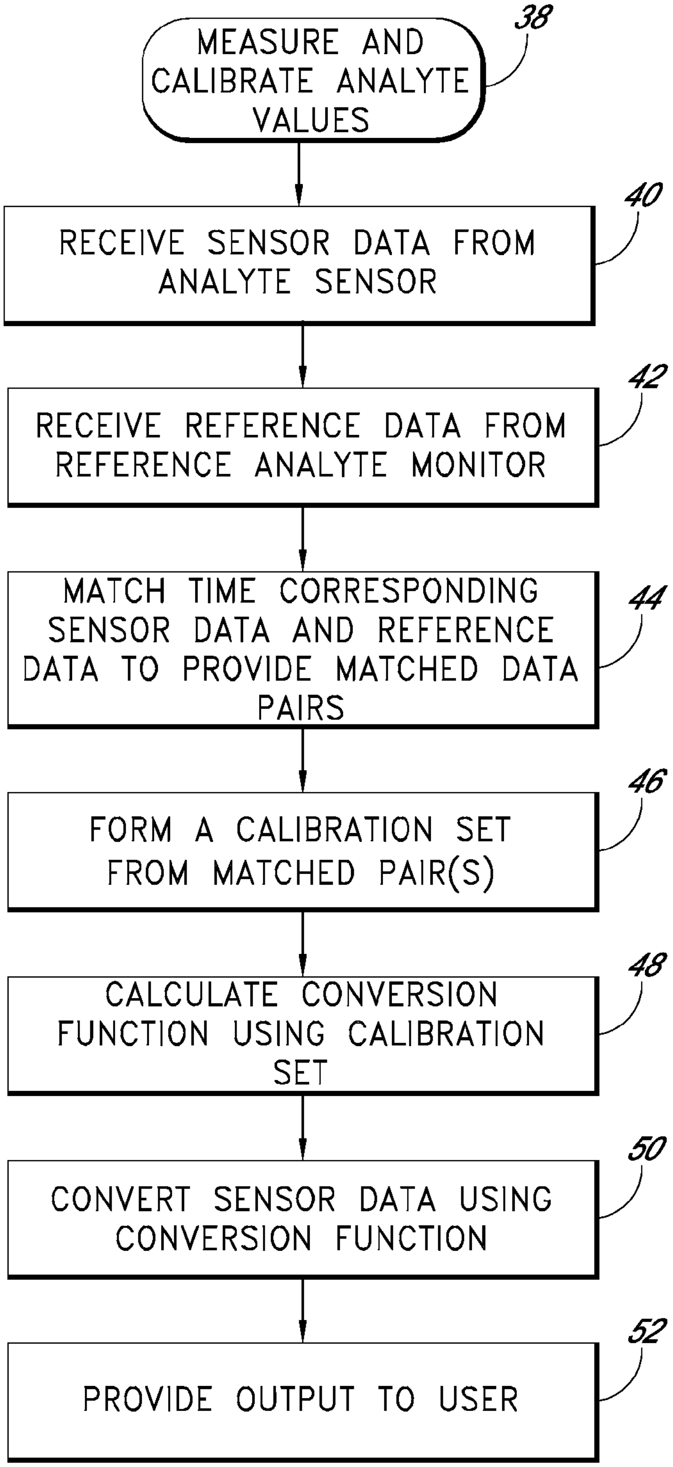
FIG. 2 is a flow chart that illustrates the process of measurement and calibration of the continuous analyte sensor in one embodiment.

Reference is now made to FIG. 2, which is a flow chart that illustrates the process 38 of calibration and data output of measured analyte values in one embodiment. Calibration of the analyte sensor 10 generally includes data processing that converts the data stream received from the continuous analyte sensor into measured analyte values that are meaningful to a user. In one embodiment, the analyte sensor is a continuous glucose sensor and one or more reference glucose values are used to calibrate the data stream from the sensor 10. The calibration can be performed on a real-time basis and/or retrospectively recalibrated. However in alternative embodiments, other calibration techniques can be utilized, for example using another constant analyte (for example, folic acid, ascorbate, urate, or the like) as a baseline, factory calibration, periodic clinical calibration, oxygen calibration (for example, using a plurality of sensor heads), or the like can be used.

At a block 40, the calibration process 38 receives continuous sensor data (for example, a data stream), including one or more time-spaced sensor data points, hereinafter referred to as "data stream," "sensor data," or "sensor analyte data." The calibration process 38 receives the sensor data from the continuous analyte sensor 10, which can be in communication (for example, wired or wireless) with the receiver 12. Some or all of the sensor data point(s) can be smoothed or replaced by estimated signal values such as described with reference to co-pending U.S. patent application Ser. No. 10/632,537 entitled, "SYSTEMS AND METHODS FOR REPLACING SIGNAL ARTIFACTS IN A GLUCOSE SENSOR DATA STREAM," filed Aug. 22, 2003, which is incorporated herein by reference in its entirety. During the initialization of the sensor, for example, prior to initial calibration, the receiver 12 receives and stores the sensor data, however it may not display any data to the user until initial calibration and optionally stabilization of the sensor 10 has been determined.

At a block 42, the calibration process 38, receives analyte values from a reference analyte monitor, including one or more reference glucose data points, hereinafter referred as "reference data" or "reference analyte data." In an example wherein the analyte sensor is a continuous glucose sensor, the reference analyte monitor can be a self-monitoring blood glucose (SMBG) meter. However, in alternative embodiments, the reference analyte monitor can be any source capable of providing a corresponding analyte value. Additionally, in some alternative embodiments, wherein the continuous analyte sensor is self-calibrating, a calibrating reference value can be provided by a source internal to the continuous sensor, for example oxygen, folic acid, or other subcutaneous fluid constants.

In some embodiments, the calibration process 38 monitors the continuous analyte sensor data stream to determine a preferred time for capturing reference analyte concentration values for calibration of the continuous sensor data stream. In an example wherein the analyte sensor is a continuous glucose sensor, when data (for example, observed from the data stream) changes too rapidly, the reference glucose value may not be sufficiently reliable for calibration due to unstable glucose changes in the host. In contrast, when sensor glucose data are relatively stable (for example, relatively low rate of change), a reference glucose value can be taken for a reliable calibration. In one embodiment, the calibration process 38 can prompt the user via the user interface to "calibrate now" when the analyte sensor is considered stable.

In some embodiments, the calibration process 38 can prompt the user via the user interface 20 to obtain a reference analyte value for calibration at intervals, for example when analyte concentrations are at high and/or low values. In some additional embodiments, the user interface 20 can prompt the user to obtain a reference analyte value for calibration based upon certain events, such as meals, exercise, large excursions in analyte levels, faulty or interrupted data readings, or the like. In some embodiments, the estimative algorithms can provide information useful in determining when to request a reference analyte value. For example, when estimated analyte values indicate approaching clinical risk, the user interface 20 can prompt the user to obtain a reference analyte value.

In some embodiments, certain acceptability parameters can be set for reference values. In an example wherein the analyte sensor is a glucose sensor, the receiver may only accept reference glucose data between about 40 and about 400 mg/dL.

In some embodiments, the calibration process 38 performs outlier detection on the reference data and time corresponding sensor data. Outlier detection compares a reference analyte value with a time corresponding measured analyte value to ensure a predetermined statistically, physiologically, or clinically acceptable correlation between the corresponding data exists. In an example wherein the analyte sensor is a glucose sensor, the reference glucose data is matched with substantially time corresponding calibrated sensor data and the matched data are plotted on a Clarke Error Grid to determine whether the reference analyte value is an outlier based on clinical acceptability, such as described in more detail with reference U.S. patent application Ser. No. 10/633,367 entitled, "SYSTEM AND METHODS FOR PROCESSING ANALYTE SENSOR DATA," filed Aug. 1, 2003, which is incorporated herein by reference in its entirety. In some embodiments, outlier detection compares a reference analyte value with a corresponding estimated analyte value, such as described in more detail with reference to FIGS. 7 and 8, and the matched data is evaluated using statistical, clinical, and/or physiological parameters to determine the acceptability of the matched data pair. In alternative embodiments, outlier detection can be determined by other clinical, statistical, and/or physiological boundaries.

At a block 44, the calibration process 38 matches reference analyte data (for example, one or more reference glucose data points) with substantially time corresponding sensor analyte data (for example, one or more sensor glucose data points) to provide one or more matched data pairs. In one embodiment, one reference data point is matched to one time corresponding sensor data point to form a matched data pair. In another embodiment, a plurality of reference data points are averaged (for example, equally or non-equally weighted average, mean-value, median, or the like) and matched to one time corresponding sensor data point to form a matched data pair. In another embodiment, one reference data point is matched to a plurality of time corresponding sensor data points averaged to form a matched data pair. In yet another embodiment, a plurality of reference data points are averaged and matched to a plurality of time corresponding sensor data points averaged to form a matched data pair.

In one embodiment, a time corresponding sensor data comprises one or more sensor data points that occur, for example, 15±5 min after the reference glucose data timestamp (for example, the time that the reference glucose data is obtained). In this embodiment, the 15 minute time delay has been chosen to account for an approximately 10 minute delay introduced by the filter used in data smoothing and an approximately 5 minute membrane-related time lag (for example, the time necessary for the glucose to diffuse through a membrane(s) of a glucose sensor). In alternative embodiments, the time corresponding sensor value can be more or less than in the above-described embodiment, for example ±60 minutes. Variability in time correspondence of sensor and reference data can be attributed to, for example, a longer or shorter time delay introduced during data smoothing, or if the configuration of the glucose sensor 10 incurs a greater or lesser physiological time lag. In some embodiments, estimated sensor data can be used to provide data points that occur about 1 second to about 60 minutes, or more, after a reference analyte value is obtained, which data can be used to match with reference analyte data, such as described in more detail below with reference to FIGS. 7 and 8.

At a block 46 the calibration process 38 forms an initial calibration set from a set of one or more matched data pairs, which are used to determine the relationship between the reference analyte data and the sensor analyte data, such as described in more detail with reference to a block 48, below.

The matched data pairs, which make up the initial calibration set, can be selected according to predetermined criteria. In some embodiments, the number (n) of data pair(s) selected for the initial calibration set is one. In other embodiments, n data pairs are selected for the initial calibration set wherein n is a function of the frequency of the received reference glucose data points. In one exemplary embodiment, six data pairs make up the initial calibration set. In another embodiment, the calibration set includes only one data pair.

In some embodiments, the data pairs are selected only within a certain glucose value threshold, for example wherein the reference glucose value is between about 40 and about 400 mg/dL. In some embodiments, the data pairs that form the initial calibration set are selected according to their time stamp.

At the block 48, the calibration process 38 calculates a conversion function using the calibration set. The conversion function substantially defines the relationship between the reference analyte data and the sensor analyte data. A variety of known methods can be used with the preferred embodiments to create the conversion function from the calibration set. In one embodiment, wherein a plurality of matched data points form the initial calibration set, a linear least squares regression is performed on the initial calibration set. Co-pending U.S. patent application Ser. No. 10/633,367 entitled, "SYSTEM AND METHODS FOR PROCESSING ANALYTE SENSOR DATA," filed Aug. 1, 2003, which is incorporated herein by reference in its entirety describes methods for calibration.

In one embodiment, the conversion function can be used to estimate analyte values for a future time period by forward projection. In alternative preferred embodiments, such as described with reference to the flow chart of FIG. 2 and with reference to FIGS. 3 to 19, the processor can provide intelligent estimation, including dynamic determination of an algorithm, physiological boundaries, evaluation of the estimative algorithm, analysis of variations associated with the estimation, and comparison of measured analyte values with time corresponding estimated analyte values.

At a block 50, the calibration process 38 uses the conversion function to transform sensor data into substantially measured analyte values, also referred to as calibrated data, as sensor data is continuously (or intermittently) received from the sensor. For example, the offset value at any given point in time can be subtracted from the raw value (for example, in counts) and divided by the slope to obtain a measured glucose value:

$$\text{Glucose Concentration} = \frac{(\text{raw value} - \text{offset})}{\text{slope}}$$

In some alternative embodiments, the sensor and/or reference glucose data are stored in a database for retrospective analysis. The calibrated data can be used to compare with the estimated analyte values, such as described in more detail with reference to FIG. 10 in order to determine a deviation of the measure value from the estimated analyte values for the corresponding time period.

At a block 52, the calibration process 38 generates output via the user interface 20 and/or the external device 34. In one embodiment, the output is representative of measured analyte values, which are determined by converting the sensor data into a meaningful analyte value such as described in more detail with reference to block 50, above. User output can be in the form of a numeric estimated analyte value, an indication of directional trend of analyte concentration, and/or a graphical representation of the measured analyte data over a period of time, for example. Other representations of the measured analyte values are also possible, for example audio and tactile. Additionally or alternatively, the output is representative of estimated analyte values, such as described in more detail with reference to FIGS. 20 to 26.

In one embodiment, the measured analyte value is represented by a numeric value. In other exemplary embodiments, the user interface graphically represents the measured analyte trend values over a predetermined time period (for example, one, three, and nine hours, respectively). In alternative embodiments, other time periods can be represented. In alternative embodiments, pictures, animation, charts, graphs, and numeric data can be selectively displayed.

Accordingly, after initial calibration of the sensor, continuous analyte values can be displayed on the user interface 20 so that the user can regularly and proactively care for his/her diabetic condition within the bounds set by his/her physician. Both the reference analyte data and the sensor analyte data from the continuous analyte sensor can be displayed to the user. In an embodiment wherein the continuous analyte sensor functions as an adjunctive device to a reference analyte monitor, the user interface 20 can display numeric reference analyte data, while showing the sensor analyte data only in a graphical representation so that the user can see the historical and present sensor trend information as well as the most recent reference analyte data value. In an embodiment wherein the continuous analyte sensor functions as a non-adjunctive device to the reference analyte monitor, the user interface can display the reference analyte data and/or the sensor analyte data. The user can toggle through menus and screens using the buttons in order to view alternate data and/or screen formats, for example.

In alternative embodiments, the output module displays the estimated analyte values in a manner such as described in more detail with reference to FIGS. 20 to 26, for example. In some embodiments, the measured analyte value, an estimated future analyte value, a rate of change, and/or a directional trend of the analyte concentration is used to control the administration of a constituent to the user, including an appropriate amount and time, in order to control an aspect of the user's biological system. One such example is a closed loop glucose sensor and insulin pump, wherein the glucose data (for example, estimated glucose value, rate of change, and/or directional trend) from the glucose sensor is used to determine the amount of insulin, and time of administration, that can be given to a person with diabetes to evade hyperglycemic and hypoglycemic conditions. Output to external devices is described in more detail with reference to FIGS. 27 to 30, for example.

Dynamic and Intelligent Analyte Value Estimation

Estimative algorithms can be applied continuously, or selectively turned on/off based on conditions. Conventionally, a data stream received from a continuous analyte sensor can provide an analyte value and output the same to the host, which can be used to warn a patient or doctor of existing clinical risk. Conventionally, a data stream received from an analyte sensor can provide historical trend analyte values, which can be used to educate a patient or doctor of individual historical trends of the patient's analyte concentration. However, the data stream cannot, without additional processing, provide future analyte values, which can be useful in preventing clinically risky analyte values, compensating for time lag, and ensuring proper matching of sensor and reference analyte, for example such as described below. Timelier reporting of analyte values and prevention of clinically risky analyte values, for example, prevention of hyper- and hypoglycemic conditions in a person with diabetes, can decrease health complications that can result from clinically risky situations.

Figure 3:
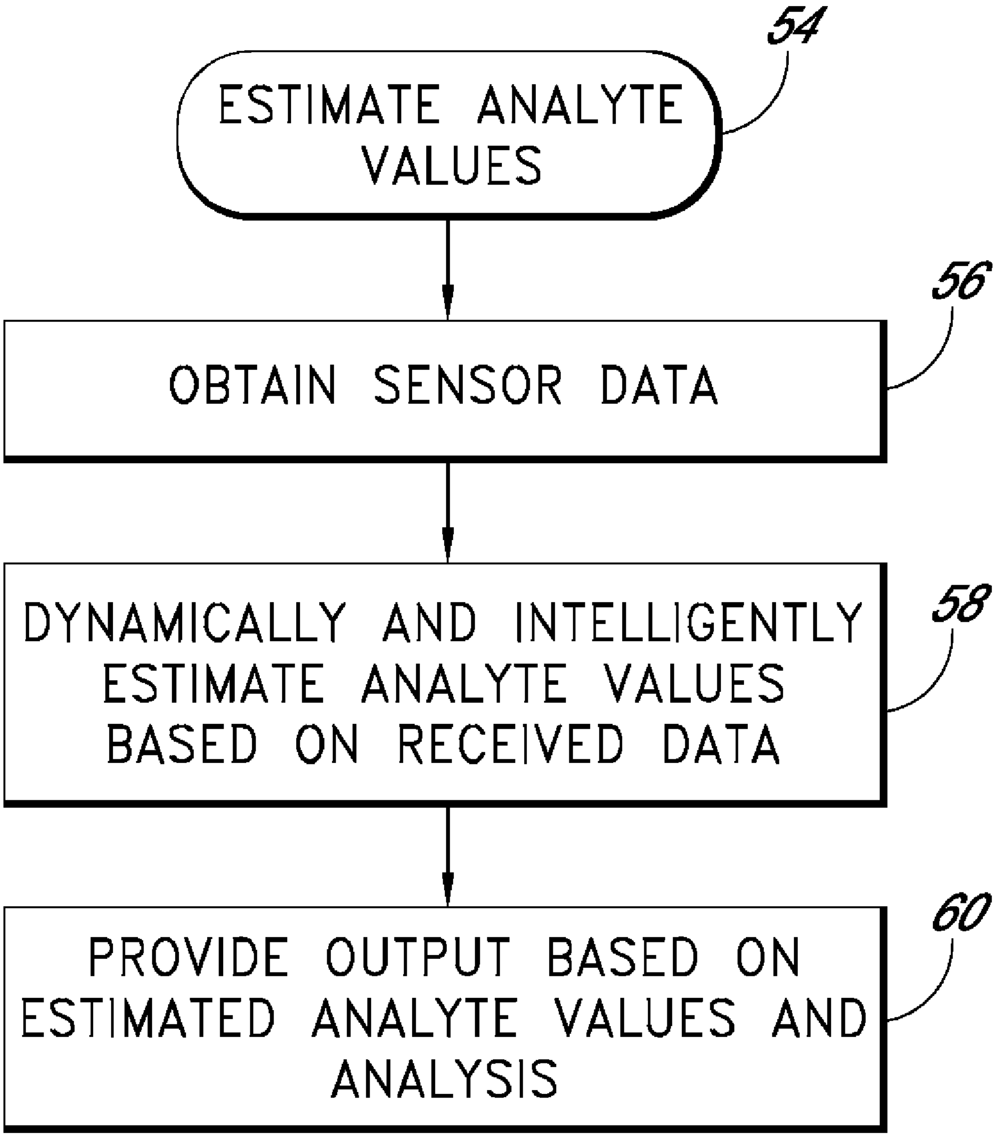
FIG. 3 is a flow chart that illustrates the process of estimation of analyte values based on measured analyte values in one embodiment.

FIG. 3 is a flow chart that illustrates the process 54 of estimating analyte values and outputting estimated analyte values in one embodiment. In contrast to the process of FIG. 2, estimation is used to calculate analyte data for time during which no data exists (for example, data gaps or future data) or to replace data when large inaccuracies are believed to exist within data (for example, signal noise due to transient ischemia). Estimation of analyte values can be performed instead of, or in combination with, calibration of measured analyte values, such as described with reference to FIG. 2, above.

The estimating analyte values process 54 can be applied continuously, or selectively turned on/off based on conditions. The determination of when to apply estimative algorithms is discussed in more detail below. In some embodiments, estimation can be applied only during approaching clinical risk to warn a patient or doctor in an effort to avoid the clinical risk, for example when the measured glucose concentration is outside of a clinically acceptable threshold (for example, 100 to 200 mg/dL) and/or the glucose concentration is increasing or decreasing at a certain rate of change (for example, 3 mg/dL/min), such as described in more detail with reference to FIG. 4, for example. In some embodiments estimation can be applied continuously, dynamically, or intermittently to compensate for a time lag associated with the analyte sensor, which time lag can be consistent, dynamic, and/or intermittent, such as described in more detail below with reference to FIGS. 5 to 6, for example. In some embodiments, estimation can be applied to aid in dynamically and intelligently matching reference data with corresponding sensor data to ensure accurate outlier detection and/or calibration of sensor data with reference data, such as described in more detail with reference to FIGS. 7 and 8, for example. In some embodiments, estimation can be applied continuously (or intermittently) in order to provide analyte data that encourages more timely proactive behavior in preempting clinical risk.

At a block 56, the estimate analyte values process 54 obtains sensor data, which can be raw, smoothed, and/or otherwise processed. In some embodiments, estimation can be applied to a raw data stream received from an analyte sensor, such as described at the block 40. In some embodiments, estimation can be applied to calibrated data, such as described at the block 50.

At a block 58, the estimate analyte values process 54 dynamically and intelligently estimates analyte values based on measured analyte values using estimative algorithms. In some embodiments, dynamic and intelligent estimation includes selecting an algorithm from a plurality of algorithms to determine an estimative algorithm (for example, first or second order regression) that best fits the present measured analyte values, such as described in more detail with reference to FIGS. 9 and 10, for example. In some embodiments, dynamic and intelligent estimation further includes constraining and/or expanding estimated analyte values using physiological parameters, such as described in more detail with reference to FIGS. 11 and 12, for example. In some embodiments, dynamic and intelligent estimation further includes evaluating the selected estimative algorithms, for example using a data association function, such as described in more detail with reference to FIGS. 9, 10, 13, and 14. In some embodiments, dynamic and intelligent estimation includes analyzing a possible variation associated with the estimated analyte values, for example using statistical, clinical, or physiological variations, such as described in more detail with reference to FIGS. 15 to 17. In some embodiments, dynamic and intelligent estimation includes comparing previously estimated analyte values with measured analyte values for a corresponding time period, determining the deviation, such as described with reference to FIGS. 18 and 19, for example. In some embodiments, the resulting deviation from the comparison can be used to determine a variation for future estimated analyte values. In some embodiments, the resulting deviation from the comparison can be used to determine a confidence level in the estimative algorithms. In some embodiments, the resulting deviation from the comparison can be used to show evidence of the benefits of displaying estimated analyte values on patient behavior, namely how well the patient responds to the estimated analyte values and alters his/her behavior in order to better control analyte levels.

At a block 60, the output module 18 provides output to the user interface 20 and/or the external device 34. In some embodiments, output of estimated analyte values is combined with output of measured analyte values, such as described at the block 52, for example combined on an LCD screen, or by toggling between screens. In some embodiments, a target analyte value or range of analyte values is output to the user interface alone, or in combination with the estimated analyte values, in order to provide a goal towards which the user can aim, such as described with reference to FIGS. 22 to 24, for example. In some embodiments, an approaching clinical risk is output in the form of a visual, audible, or tactile prompt, such as described with reference to FIGS. 20 to 22, for example. In some embodiments, therapy recommendations are output to aid the user in determining corrective action that can be performed in an effort to avoid or minimize clinical risk such as described with reference to FIG. 24, for example. In some embodiments, a visual representation of possible variations of the estimated analyte values, which variation can be due to statistical, clinical, or physiological considerations, such as described with reference to FIGS. 24 to 26, for example. In some embodiments, the output prompts a user to obtain a reference analyte value (not shown). In some embodiments, output is sent to an external device such as described with reference to FIGS. 27 to 30, for example.

Figure 4:
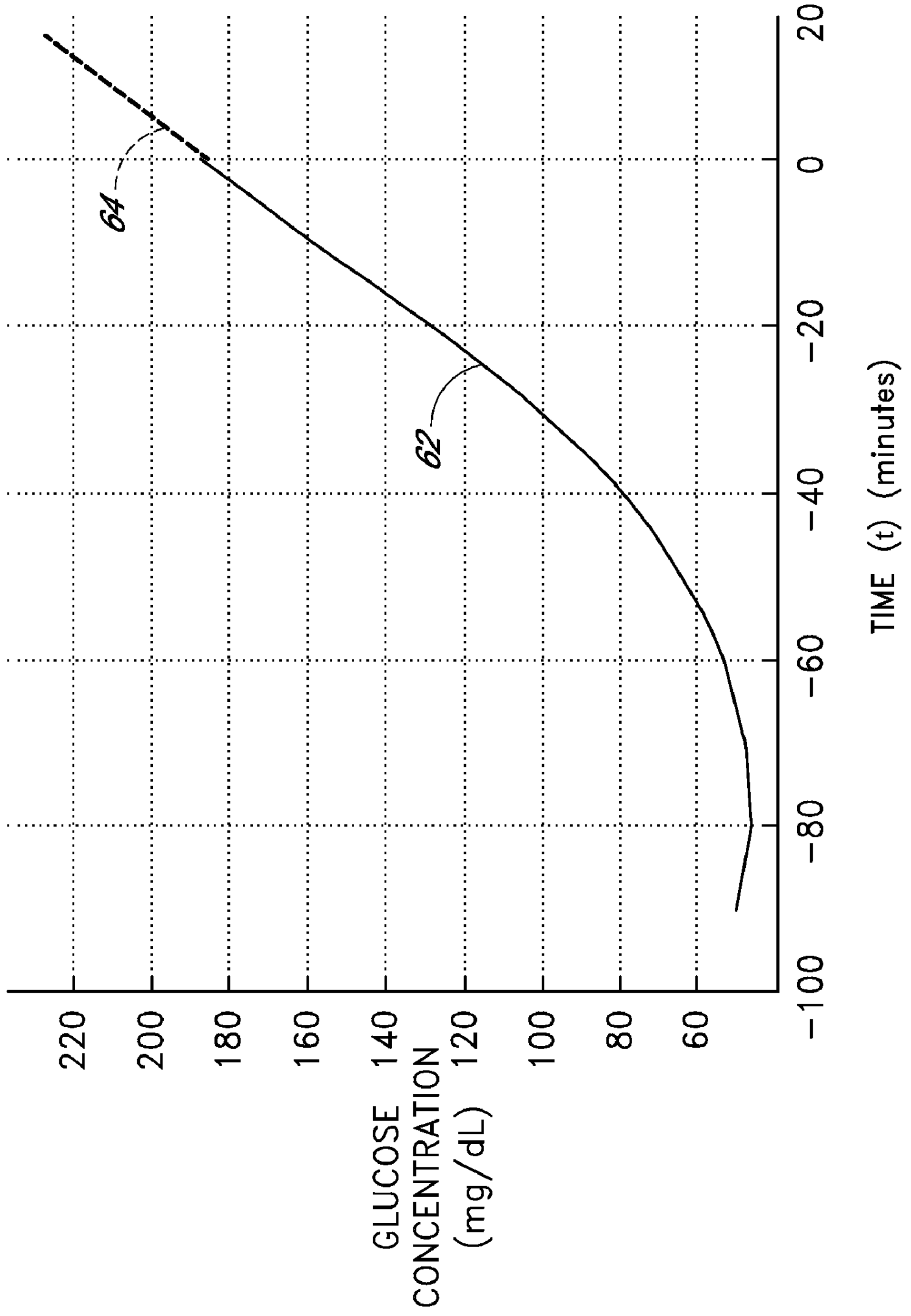
FIG. 4 is a graph that illustrates the case where estimation is triggered by an event wherein a patient's blood glucose concentration passes above a predetermined threshold.

FIG. 4 is a graph that illustrates one embodiment, wherein estimation is triggered by an event such as a patient's blood glucose concentration rising above a predetermined threshold (for example, 180 mg/dL). The x-axis represents time in minutes; the y-axis represents glucose concentration in mg/dL. The graph shows an analyte trend graph, particularly, the graph shows measured glucose data 62 for about 90 minutes up to time (t)=0. In this embodiment, the measured glucose data 62 has been smoothed and calibrated, however smoothing and/or calibrating may not be required in some embodiments. At t=0, estimation of the preferred embodiments is invoked and 15-minute estimated glucose data 64 indicates that the glucose concentration will likely rise above 220 mg/dL. The estimated glucose data 64 can be useful in providing alarms (e.g., hyper- and hypoglycemic alerts) and/or displaying on the user interface of the receiver, for example. Alarms may not require estimative algorithms in some embodiments, for example when zero, first, and/or second order calculations can be made to dynamically assess the static value, rate of change, and/or rate of acceleration of the analyte data in some embodiment.

In some embodiments, estimative algorithms are selectively applied when the reference and/or sensor analyte data indicates that the analyte concentration is approaching clinical risk. The concentration of the analyte values, the rate of change of the analyte values, and/or the acceleration of the analyte values can provide information indicative of approaching clinical risk. In an example wherein the analyte sensor is a glucose sensor, thresholds (for example, 100 to 200 mg/dL) can be set that selectively turn on estimative algorithms that then dynamically and intelligently estimate upcoming glucose values, and optionally possible variations of those estimated glucose values, to appropriately forewarn of an upcoming patient clinical risk (for example, hypo- or hyperglycemia). Additionally, the rate of change and/or acceleration can be considered to more intelligently turn on and calculate necessary estimation and for alarms (e.g., hyper- and hypoglycemic alarms). For example, if a person with diabetes has a glucose concentration of 100 mg/dL, but is trending upwardly, has slow or no rate of change, or is decelerating downwardly, estimation and/or alarms may not be necessary.

Figure 5:
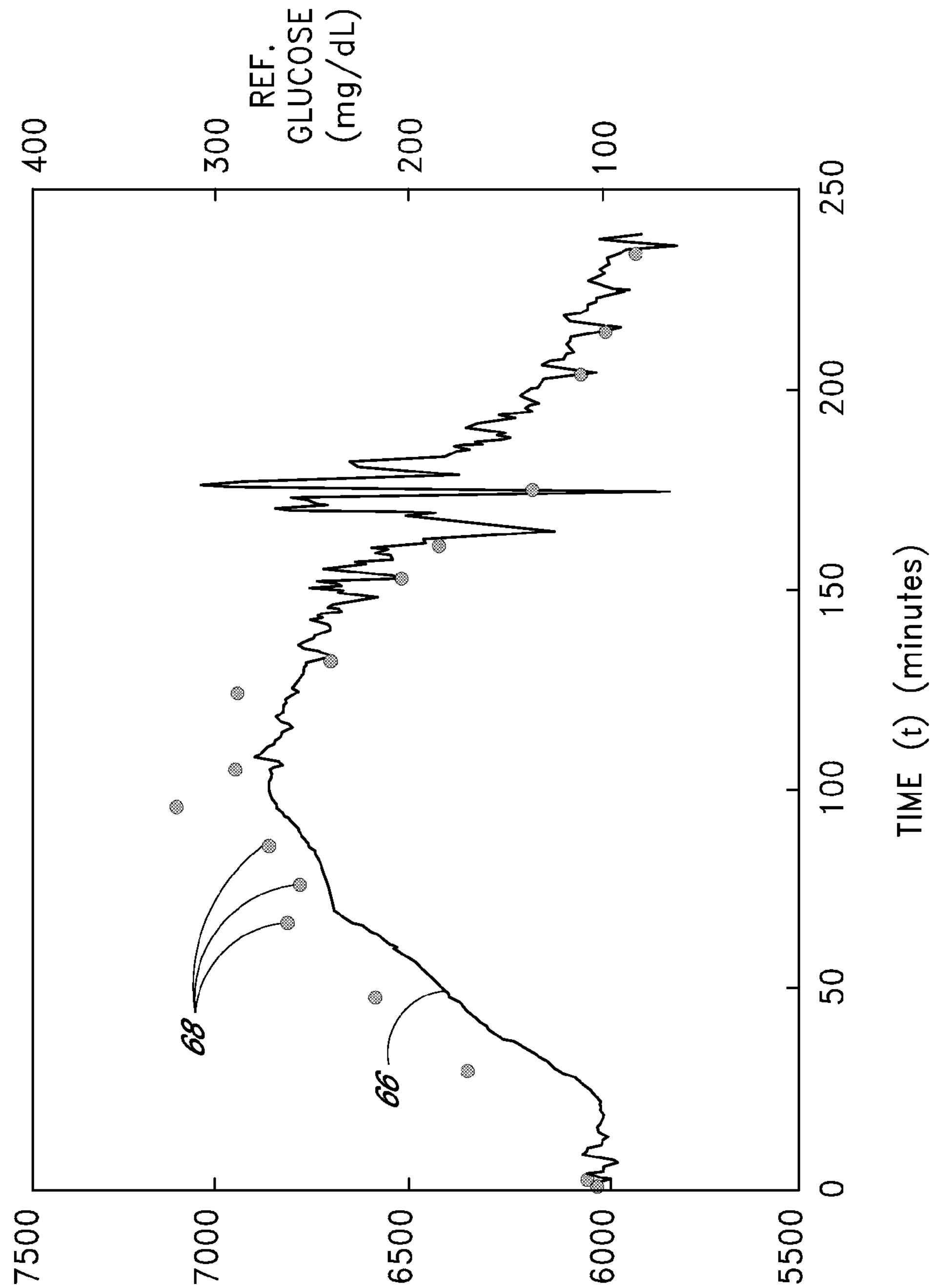
FIG. 5 is a graph that illustrates a raw data stream and corresponding reference analyte values.

FIG. 5 is a graph that illustrates a raw data stream and the corresponding reference analyte values. The x-axis represents time in minutes, the first y-axis represents sensor glucose data measured in counts, and the second y-axis represents reference glucose data in mg/dL. A raw data stream 66 was obtained for a host from a continuous glucose sensor over a 4-hour time period. In this example, the raw data stream 66 has not been smoothed, calibrated, or otherwise processed and is represented in counts. Reference glucose values 68 were obtained from the host using a reference glucose monitor during the same 4-hour time period. The raw data stream 66 and reference glucose values 68 were plotted on the graph of FIG. 5 accordingly during the 4-hour time period. While not wishing to be bound by theory, the visible difference between the reference and sensor glucose data is believed to be caused at least in part by a time lag, such as described in more detail below.

A data stream received from an analyte sensor can include a time lag within the measured analyte concentration, for example, as compared to corresponding reference analyte values. In some embodiments, a time lag can be associated with a difference in measurement samples (for example, an interstitial fluid sample measured by an implantable analyte sensor as compared with a blood sample measured by an external reference analyte monitor). In some embodiments, a time lag can be associated with diffusion of the analyte through a membrane system, for example such as has been observed in some implantable electrochemically-based glucose sensors. Additionally in some embodiments, a time lag can be associated with processing of the data stream, for example, a finite impulse response filter (FIR) or infinite impulse response (IIR) filter can be applied intermittently or continuously to a raw data stream in the sensor (or in the receiver) in order to algorithmically smooth the data stream, which can produce a time lag (for example, as shown in measured glucose data 68 of FIG. 4B). In some embodiments, wherein the analyte sensor is a subcutaneously implantable sensor, there may be a variable time lag associated with the tissue ingrowth at the biointerface at the tissue-device interface. Additionally, time lags can be variable upon a host's metabolism. In some embodiments, a time lag of the reference analyte data may be associated with an amount of time a user takes to test and report a reference analyte value. Accordingly, the preferred embodiments provide for estimation of analyte values based on measured analyte values, which can be used to compensate for a time lag such as described above, allow for output of analyte values that represent estimated present analyte values without a time lag.

Accordingly, some embodiments selectively apply estimative algorithms based on a measured, estimated, or predetermined time lag associated with the continuous analyte sensor. In some embodiments, estimative algorithms continuously run in order to continuously compensate for a time lag between reference and sensor data, such as described in more detail below. In some embodiments, estimative algorithms run during outlier detection in order to intelligently and dynamically match corresponding reference and sensor data for more accurate outlier inclusion or exclusion, such as described in more detail below. In some embodiments, estimative algorithms run during matching of data pairs for consideration in the calibration set in order to intelligently and dynamically match corresponding reference and sensor glucose data for better calibration, such as described in more detail below.

Figure 6:
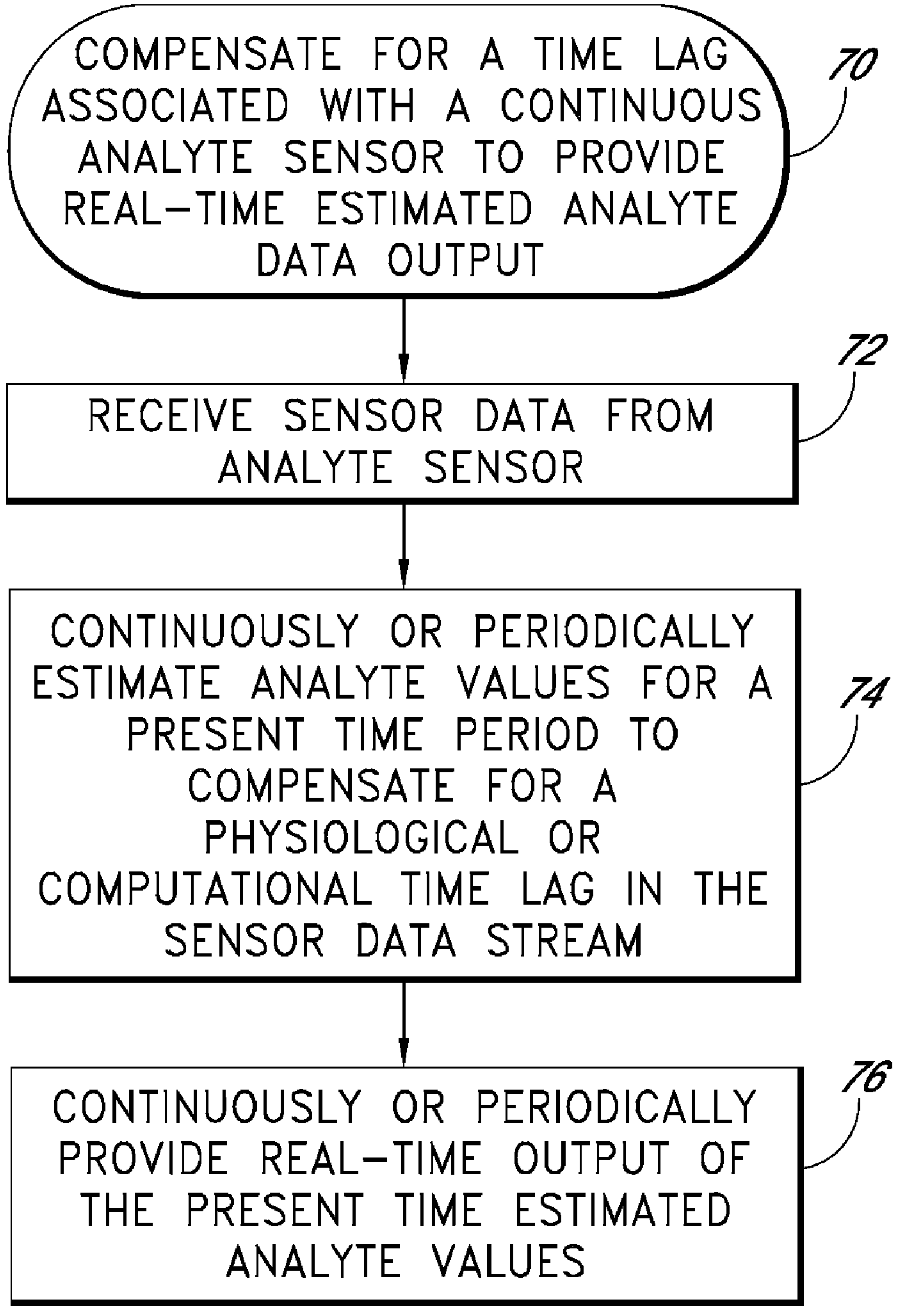
FIG. 6 is a flow chart that illustrates the process of compensating for a time lag associated with a continuous analyte sensor to provide real-time estimated analyte data output in one embodiment.

FIG. 6 is a flow chart that illustrates the process 70 of compensating for a time lag associated with a continuous analyte sensor to provide real-time estimated analyte data output in one embodiment. For the reasons described above, the system includes programming that continuously or periodically (e.g., when a user activates the LCD screen) compensates for a time lag in the system to provide a better real-time estimate to the user, for example.

At block 72, the time lag compensation process 70 obtains sensor data, which can be raw, smoothed, and/or otherwise processed. In some embodiments, estimation can be applied to a raw data stream received from an analyte sensor, such as described at the block 40. In some embodiments, estimation can be applied to calibrated data, such as described at the block 50.

At block 74, the time lag compensation process 70 continuously or periodically estimates analyte values for a present time period to compensate for a physiological or computational time lag in the sensor data stream. For example, if a 20-minute time lag is known inherent within the continuous analyte sensor, the compensation can be a 20-minute projected estimation to provide true present time (or "real time") analyte values. Some embodiments can continuously run estimation to compensate for time lag, while other embodiments can perform time lag compensation estimation only when the user interface (e.g., LCD screen) is activated by a user. Known estimation algorithms and/or the dynamic and intelligent estimation algorithms of the preferred embodiments (e.g., such as described with reference to block 58 and FIGS. 9 to 19) can be used in estimating analyte values herein.

At block 76, the time lag compensation process 70 continuously or periodically provides output of the present time estimated analyte values, such as described in more detail above. Output can be sent to the user interface 20 or to an external device 34.

Figure 7:
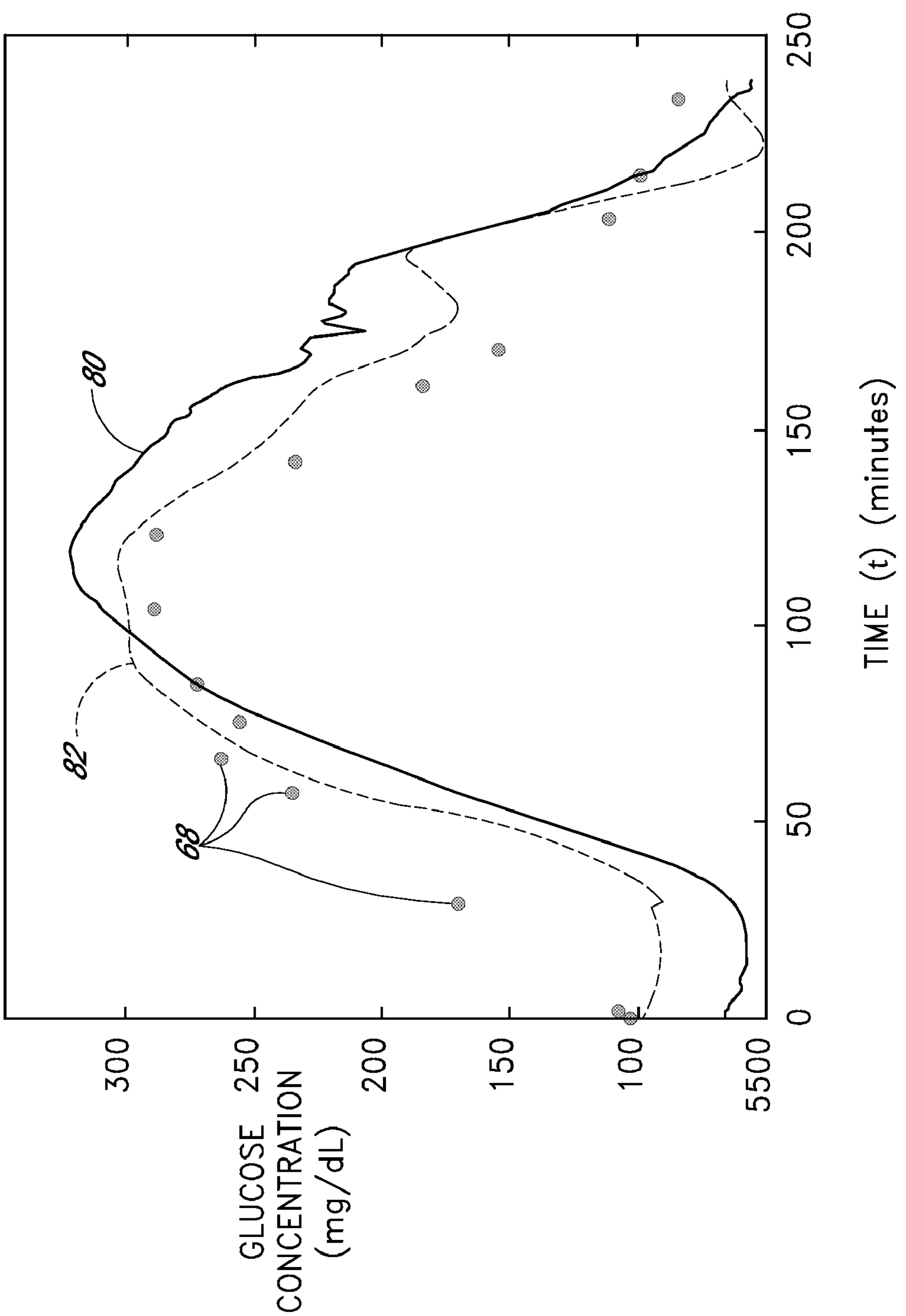
FIG. 7 is a graph that illustrates the data of FIG. 5, including reference analyte data and corresponding calibrated sensor analyte and estimated sensor analyte data, showing compensation for time lag using estimation.

Referring now to FIG. 7, which is a graph that illustrates the data of FIG. 5, including reference analyte data, corresponding calibrated sensor analyte data, and corresponding estimated analyte data, showing compensation for time lag using estimation. The x-axis represents time in minutes and the y-axis represents glucose concentration in mg/dL. Reference glucose values 68 were obtained from the host from the reference glucose monitor during the 4-hour time period and correspond to FIG. 5. Measured glucose data 80 was obtained by smoothing and calibrating the raw data stream 66 of FIG. 5 using reference glucose values 68, such as described in more detail with reference to FIG. 2. Estimated glucose data 82 was obtained by estimating using dynamic and intelligent estimation of the preferred embodiments, which is described in more detail below.

The measured glucose data 80 has been smoothed and thereby includes a data processing-related time lag, which may be in addition to physiological or membrane-related time lag, for example. Therefore, the measured glucose data 80 visibly lags behind the reference glucose values 68 on the graph. The estimated glucose data 82 includes dynamic and intelligent estimation of the preferred embodiments in order to compensate for the time lag, thereby better correlating with the reference glucose values 68. In this embodiment, the time lag compensation (estimation) is 15 minutes, however in other embodiments the time lag compensation (estimation) can be more or less.

In some embodiments, the estimation can be programmed to compensate for a predetermined time lag (for example, 0 to 60 minutes, or more). In some alternative embodiments, the estimation can be dynamically adjusted based on a measured time lag; for example, when estimation is used to dynamically match sensor analyte data with reference analyte data such as described below, the time difference between best corresponding sensor analyte data and reference analyte data can be used to determine the time lag.

Figure 8:
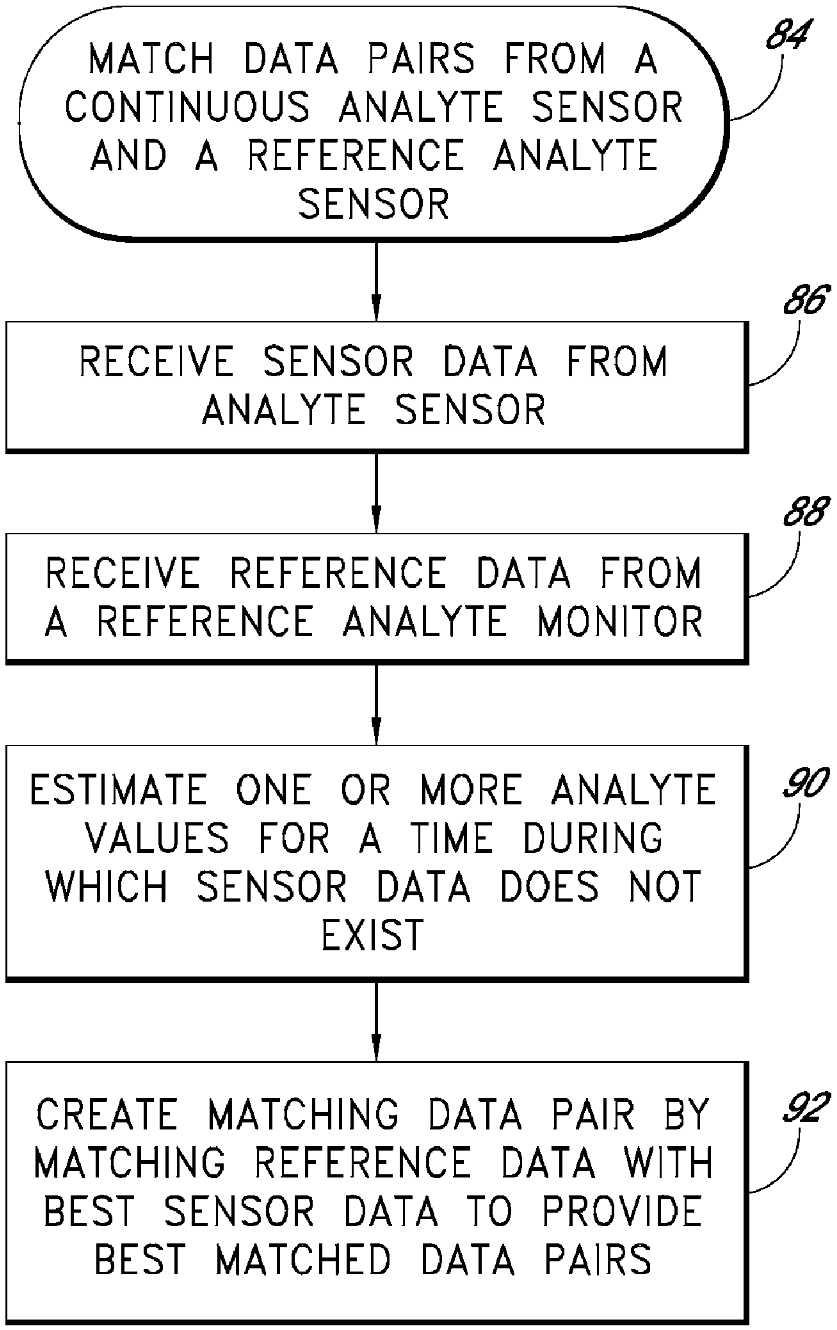
FIG. 8 is a flow chart that illustrates the process of matching data pairs from a continuous analyte sensor and a reference analyte sensor in one embodiment.

FIG. 8 is a flow chart that illustrates the process 84 of matching data pairs from a continuous analyte sensor and a reference analyte sensor in one embodiment. Estimative algorithms of the preferred embodiments are useful when selectively applied during the process of matching corresponding sensor and reference analyte data, for example during outlier detection, such as described in more detail with reference to FIG. 2 at block 42, and/or matching data pairs for calibration, such as described in more detail with reference to FIG. 2 at block 44. For the reasons stated above with reference to FIGS. 5 to 7, for example, a time lag associated with the continuous analyte sensor and/or the reference analyte monitor can hinder the ability to accurately match data from the analyte sensor with corresponding data from the reference analyte monitor using time-correspondence only.

At block 86, the data matching process 84 obtains sensor data, which can be raw, smoothed, and/or otherwise processed. In some embodiments, data matching can use data from a raw data stream received from an analyte sensor, such as described at the block 40. In some embodiments, data matching can use calibrated data, such as described at the block 50.

At block 88, the data matching process 84, receives analyte values from a reference analyte monitor, including one or more reference glucose data points, hereinafter referred as “reference data” or “reference analyte data.” In an example wherein the analyte sensor is a continuous glucose sensor, the reference analyte monitor can be a self-monitoring blood glucose (SMBG) meter. Other examples are described with reference to block 42, above.

At block 90, the data matching process 84 estimates one or more analyte values for a time period during which no data exists (or when data is unreliable or inaccurate, for example) based on the data stream. For example, the estimated analyte values can include values at intervals from about 30 seconds to about 5 minutes, and can be estimated for a time period of about 5 minutes to about 60 minutes in the future. In some embodiments, the time interval and/or time period can be more or less. Known estimation algorithms and/or the dynamic and intelligent estimation algorithms of the preferred embodiments (e.g., such as described with reference to block 58 and FIGS. 9 to 19) can be used in estimating analyte values herein.

At block 92, the data matching process 84 creates at least one matched data pair by matching reference analyte data to a corresponding analyte value from the one or more estimated analyte values. In some embodiments, the best matched pair can be evaluated by comparing a reference data point against individual sensor values over a predetermined time period (for example, +/−0 to 60 minutes). In one such embodiment, the reference data point is matched with sensor data points at intervals (for example, 5-minute intervals of measured historical analyte values and estimated future analyte values) and each matched pair is evaluated. The matched pair with the best correlation (for example, based on statistical deviation, clinical risk analysis, or the like) can be selected as the best matched pair and should be used for data processing. In some alternative embodiments, matching a reference data point with an average of a plurality of sensor data points over a time period can be used to form a matched pair.

Therefore, the preferred embodiments provide for estimation of analyte values based on measured analyte values that can be helpful in more accurately and/or appropriately matching sensor and reference analyte values that represent corresponding data. By increasing the accuracy of matched data pairs, true real-time estimated analyte values (for example, without a time lag) can be provided, calibration can be improved, and outlier detection can be more accurate and convenient, thereby improving overall patient safety and convenience.

While any of the above uses and applications can be applied using conventional algorithms that provide conventional projection based on first or second order regression, for example, it has been found that analyte value estimation can be further improved by adaptively applying algorithms, for example using dynamic intelligence such as described in more detail below. The dynamic and intelligent algorithms described herein can be applied to the uses and applications described above, or for estimating analyte values at any time for any use or application.

Figure 9:
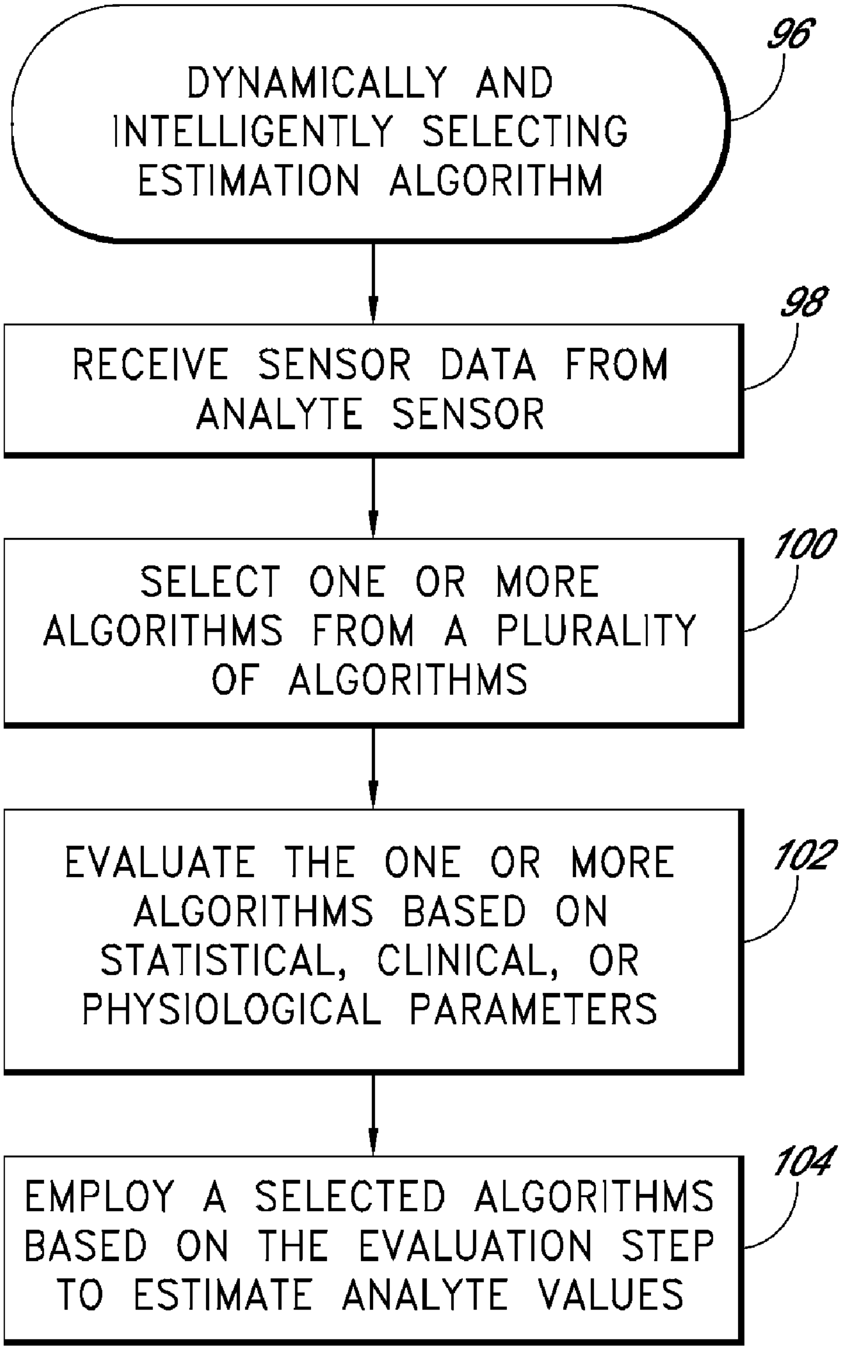
FIG. 9 is a flow chart that illustrates the process of dynamic and intelligent estimation algorithm selection in one embodiment.

FIG. 9 is a flow chart that illustrates the dynamic and intelligent estimation algorithm selection process 96 in one embodiment.

At block 98, the dynamic and intelligent estimation algorithm selection process 96 obtains sensor data, which can be raw, smoothed, and/or otherwise processed. In some embodiments, data matching can use data from a raw data stream received from an analyte sensor, such as described at block 40. In some embodiments, data matching can use calibrated data, such as described at block 50.

At block 100, the dynamic and intelligent estimation algorithm selection process 96 includes selecting one or more algorithms from a plurality of algorithms that best fits the measured analyte values. In some embodiments, the estimative algorithm can be selected based on physiological parameters; for example, in an embodiment wherein the analyte sensor is a glucose sensor, a first order regression can be selected when the rate of change of the glucose concentration is high, indicating correlation with a straight line, while a second order regression can be selected when the rate of change of the glucose concentration is low, indicating correlation with a curved line. In some embodiments, a first order regression can be selected when the reference glucose data is within a certain threshold (for example, 100 to 200 mg/dL), indicating correlation with a straight line, while a second order regression can be selected when the reference glucose data is outside of a certain threshold (for example, 100 to 200 mg/dL), indicating correlation with a curved line because the likelihood of the glucose concentration turning around (for example, having a curvature) is greatest at high and low values.

Generally, algorithms that estimate analyte values from measured analyte values include any algorithm that fits the measured analyte values to a pattern, and/or extrapolates estimated values for another time period (for example, for a future time period or for a time period during which data needs to be replaced). In some embodiments, a polynomial regression (for example, first order, second order, third order, etc.) can be used to fit measured analyte values to a pattern, and then extrapolated. In some embodiments, autoregressive algorithms (for example, IIR filter) can be used to fit measured analyte values to a pattern, and then extrapolated. In some embodiments, measured analyte values can be filtered by frequency before projection (for example, by converting the analyte values with a Fourier transform, filtering out high frequency noise, and converting the frequency data back to time values by using an inverse Fourier transform); this data can then be projected forward (extrapolated) along lower frequencies. In some embodiments, measured analyte values can be represented with a Wavelet transform (for example filtering out specific noise depending on wavelet function), and then extrapolate forward. In some alternative embodiments, computational intelligence (for example, neural network-based mapping, fuzzy logic based pattern matching, genetic-algorithms based pattern matching, or the like) can be used to fit measured analyte values to a pattern, and/or extrapolate forward. In yet other alternative embodiments, time-series forecasting, using methods such as moving average (single or double), exponential smoothing (single, double, or triple), time series decomposition, growth curves, Box-Jenkins, or the like. The plurality of algorithms of the preferred embodiments can utilize any one or more of the above-described algorithms, or equivalents, in order to intelligently select estimative algorithms and thereby estimate analyte values.

In some embodiments, estimative algorithms further include parameters that consider external influences, such as insulin therapy, carbohydrate consumption, or the like. In one such example, these additional parameters can be user input via the user interface 20 or transmitted from an external device 34, such as described in more detail with reference to FIG. 1. By including such external influences in additional to historical trend data (measured analyte values), analyte concentration changes can be better anticipated.

At block 102, the selected one or more algorithms are evaluated based on statistical, clinical, or physiological parameters. In some embodiments, running each algorithm on the data stream tests each of the one or more algorithms, and the algorithmic result with the best correlation to the measured analyte values is selected. In some embodiments, the pluralities of algorithms are each compared for best correlation with physiological parameters (for example, within known or expected rates of change, acceleration, concentration, etc). In some embodiments, the pluralities of algorithms are each compared for best fit within a clinical error grid (for example, within "A" region of Clarke Error Grid). Although first and second order algorithms are exemplified herein, any two or more algorithms such as described in more detail below could be programmed and selectively used based on a variety of conditions, including physiological, clinical, and/or statistical parameters.

At block 104, the algorithm(s) selected from the evaluation step is employed to estimate analyte values for a time period. Accordingly, analyte values are more dynamically and intelligently estimated to accommodate the dynamic nature of physiological data. Additional processes, for example applying physiological boundaries (FIG. 11), evaluation of the estimation algorithms after employing the algorithms (FIG. 13), evaluating a variation of estimated analyte values (FIG. 15), measuring and comparing analyte values (FIG. 18), or the like can be applied to the dynamic and intelligent estimative algorithms described with reference to FIG. 9.

Figure 10:
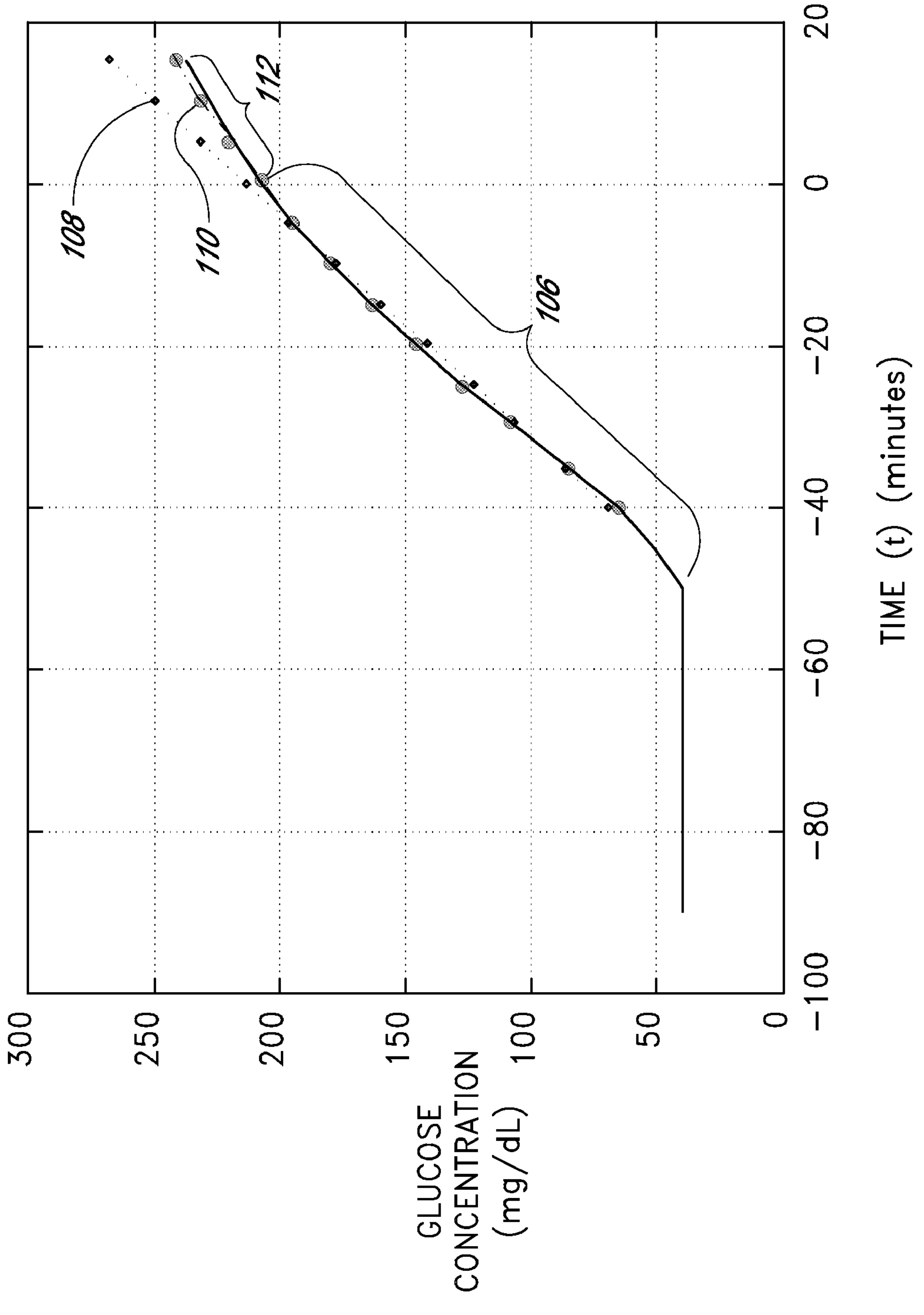
FIG. 10 is a graph that illustrates one case of dynamic and intelligent estimation applied to a data stream, showing first order estimation, second order estimation, and the measured values for a time period, wherein the second order estimation shows a closer correlation to the measured data than the first order estimation.

FIG. 10 is a graph that illustrates dynamic and intelligent estimation algorithm selection applied to a data stream in one embodiment showing first order estimation, second order estimation, and the measured glucose values for the time period, wherein the second order estimation shows a better correlation to the measured glucose data than the first order estimation. The x-axis represents time in minutes. The y-axis represents glucose concentration in mg/dL.

In the data of FIG. 10, measured (calibrated) sensor glucose data 106 was obtained up to time t=0. At t=0, a first order regression 108 was performed on the measured data 106 to estimate the upcoming 15-minute time period. A second order regression 110 was also performed on the data to estimate the upcoming 15-minute time period. The intelligent estimation of the preferred embodiments, such as described in more detail below, chose the second order regression 110 as the preferred algorithm for estimation based on programmed conditions (at t=0). The graph of FIG. 10 further shows the measured glucose values 112 from t=0 to t=15 to illustrate that second order regression 110 does in fact more accurately correlate with the measured glucose data 112 than first order regression 108 from t=0 to t=15.

In the example of FIG. 10, the dynamic and intelligent estimation algorithm selection determined that the second order regression 110 was the preferred algorithm for estimation at t=0 based on conditions. A first condition was based on a set threshold that considers second order regression a better fit when measured glucose values are above 200 mg/dL and trending upwardly. A second condition verifies that the curvature of the second order regression line appropriately shows a deceleration above 200 mg/dL. Although two specific examples of conditions are described herein, dynamic and intelligent estimation can have as many or as few conditions programmed therein as can be imagined or contrived. Some additional examples of conditions for selecting from a plurality of algorithms are listed above, however the scope of this aspect of dynamic and intelligent estimation includes any conditional statements that can be programmed and applied to any algorithms that can be implemented for estimation.

Figure 11:
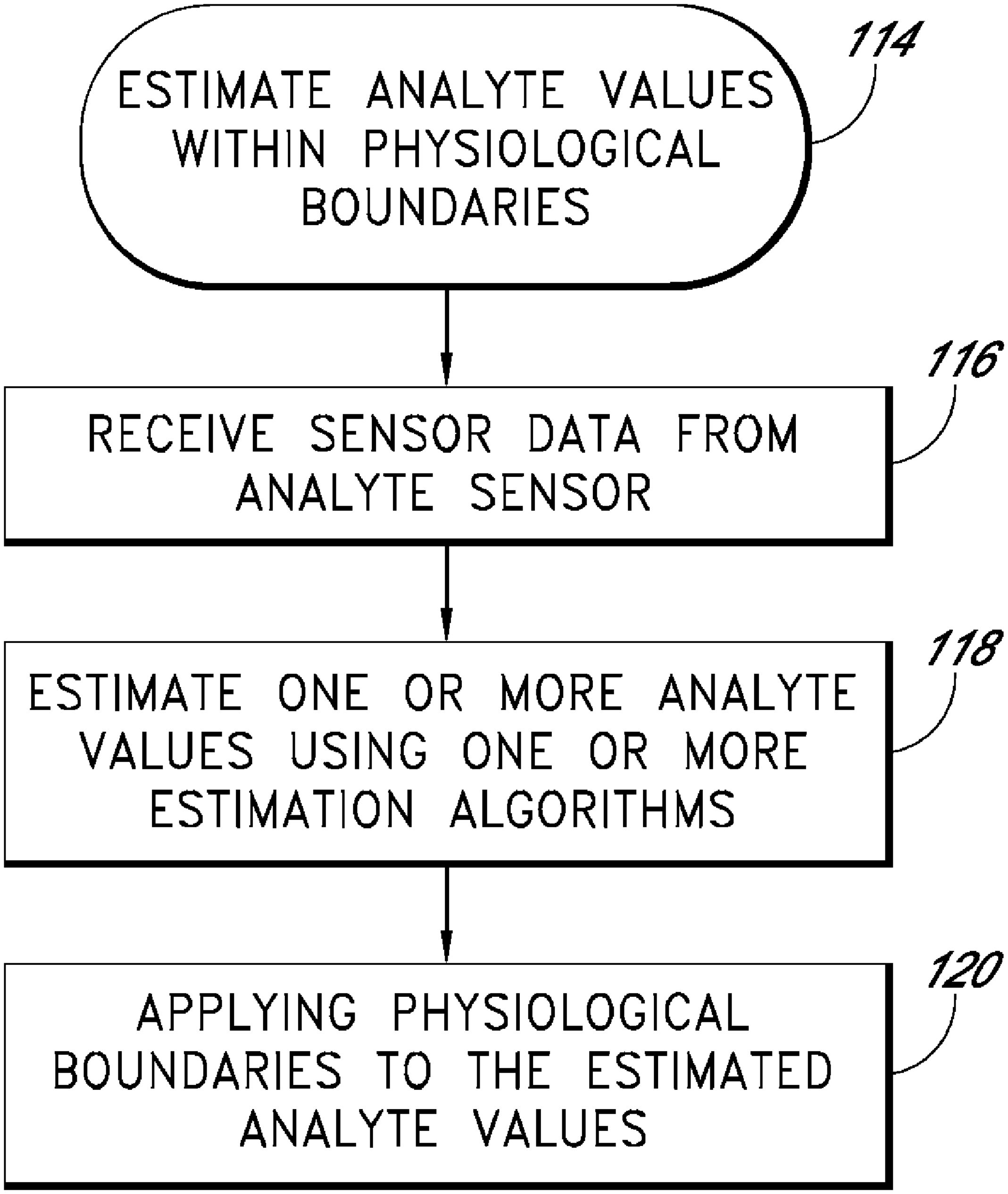
FIG. 11 is a flow chart that illustrates the process of estimating analyte values within physiological boundaries in one embodiment.

FIG. 11 is a flow chart that illustrates the process 114 of estimating analyte values within physiological boundaries in one embodiment. The embodiment described herein is provided because the estimative algorithms such as described with reference to FIG. 9 consider mathematical equations, which may or may not be sufficient to accurately estimate analyte values based on measured analyte values.

At block 116, the analyte value estimation with physiological boundaries process 114 obtains sensor data, which can be raw, smoothed, calibrated and/or otherwise processed.

At block 118, the analyte value estimation with physiological boundaries process 114 estimates one or more analyte values using one or more estimation algorithms. In some embodiments, this analyte value estimation uses conventional projection using first or second order regression, for example. In some embodiments, dynamically and intelligently selecting of one or more algorithms from a plurality of algorithms (FIG. 9), evaluating estimation algorithms after employing the algorithms (FIG. 13), evaluating a variation of estimated analyte values (FIG. 15), measuring and comparing analyte values (FIG. 18), or the like can be applied to the dynamic and intelligent estimative algorithms described with reference to FIG. 9.

At block 120, the analyte value estimation with physiological boundaries process 114 applies physiological boundaries to the estimated analyte values of block 118. In some circumstances, physiological changes in a host and associated sensor data stream follow a relatively mathematical curvature. However there are additional considerations that are not inherently included in the mathematical calculation of estimative algorithms, such as physiological boundaries. One example of a circumstance or consideration that can occur is signal noise or signal artifact on the data stream, for example due to transient ischemia, signal from an interfering species, or the like. In such circumstances, normal mathematical calculations can result in estimated analyte values that fall outside of physiological boundaries. For example, a first order regression can produce a line that exceeds a known physiological rate of change of glucose in humans (for example, about 4 to 5 mg/dL/min). As another example, a second order regression can produce a curvature that exceeds a known physiological acceleration in humans (for example, about 0.1 to 0.2 mg/dL/min$^2$). As yet another example, it has been observed that the best solution for the shape of the curve at any point along a glucose signal data stream over a certain time period (for example, about 20 to 30 minutes) is a straight line, which can be used to set physiological boundaries. As yet another example, a curvature defined by a second order regression at low glucose values (for example, below 80 mg/dL) generally decelerates as it goes down and accelerates as it goes up, while a curvature defined by a second order regression at high glucose values generally decelerates as it goes up and accelerates as it goes down. As yet another example, an individual's physiological patterns can be monitored over a time period (for example, from about one day to about one year) and individual's physiological patterns quantified using pattern recognition algorithms; the individual's physiological patterns could be used to increase the intelligence of the estimation by applying the quantified patterns to the estimated analyte values.

Accordingly, physiological boundaries, includes those described above, or other measured or known physiological analyte boundaries, can compliment an estimative algorithm to ensure that the estimated analyte values fall within known physiological parameters. However, in some alternative embodiments, physiological boundaries can be applied to raw and/or smoothed data, thereby eliminating the need for the estimation step (block 118).

Figure 12:
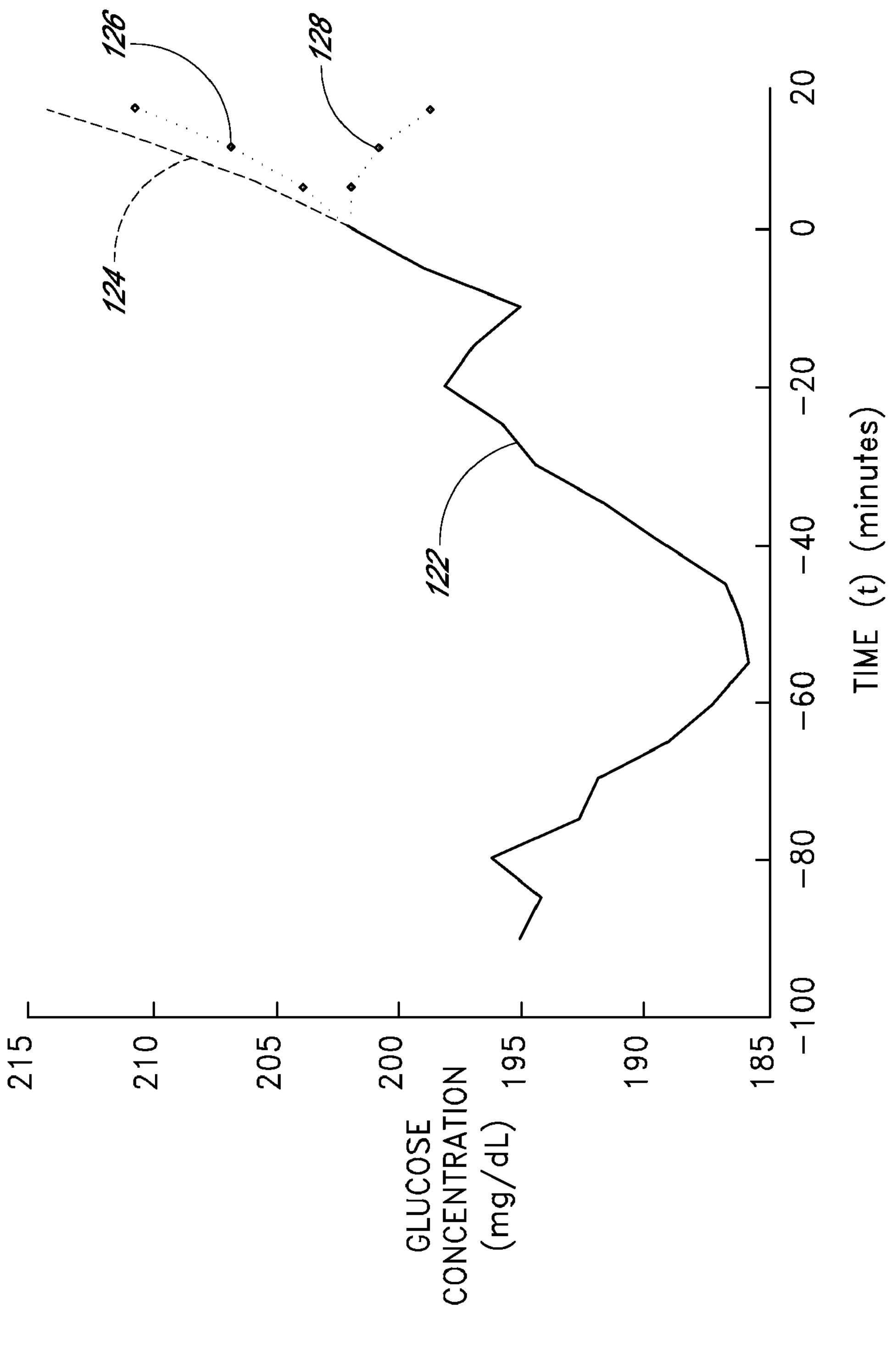
FIG. 12 is a graph that illustrates one case wherein dynamic and intelligent estimation is applied to a data stream, wherein the estimation performs regression and further applies physiological constraints to the estimated analyte data.

FIG. 12 is a graph that illustrates physiological boundaries applied to a data stream in one embodiment, wherein the dynamic and intelligent estimation includes performing an estimative algorithm and further applies physiological boundaries to the estimated analyte data. The x-axis represents time in minutes. The y-axis represents glucose concentration in mg/dL. Measured glucose data 122 is shown for about 90 minutes up to t=0. At t=0, an estimative algorithm performs estimation using a second order regression of the previous 40 minutes to generate a slope and acceleration, which are used to extrapolate the estimated glucose data 124 beginning at the measured analyte data at t=0. At the same time (t=0), the system uses known physiological parameters to determine physiologically feasible boundaries of glucose concentration over the estimated 15-minute period. In this example, the system uses a slope and intercept defined by a first order regression using 25 minutes of data up to t=0, from which the system sets physiological boundaries using a maximum acceleration of glucose of 0.2 mg/dL/min$^2$ and a maximum rate of change of glucose of 4 mg/dL/min for the upcoming 15 minutes. Using the above-described physiological parameters, an upper physiological boundary 126 and a lower physiological boundary 128 are set. Interestingly, the estimated glucose data 124 falls outside of the physiological boundaries, namely above the upper physiological boundary 126. In this case, the second order regression estimated glucose data 124 has either a rate of change greater than 4 mg/dL/min and/or acceleration greater than 0.2 mg/dL/min$^2$. Such circumstances can be caused by noise on the signal, artifact of performing regression over a predetermined time period during which a change in analyte concentration is not best described by a regression line, or numerous other such affects.

In this case, estimated glucose values 124 can be adjusted to be the upper limit 126 in order to better represent physiologically feasible estimated analyte values. In some embodiments, some or all of the estimated analyte values falling outside of the physiological parameters can trigger the dynamic and intelligent estimative algorithms to re-select an algorithm, or to adjust the parameters of the algorithm (for example, increase and/or decrease the number of data points considered by the algorithm) to better estimate during that time period. In some alternative embodiments, statistical and or clinical boundaries can be used to bound estimated analyte values and/or adjust the parameters that drive those algorithms.

Figure 13:
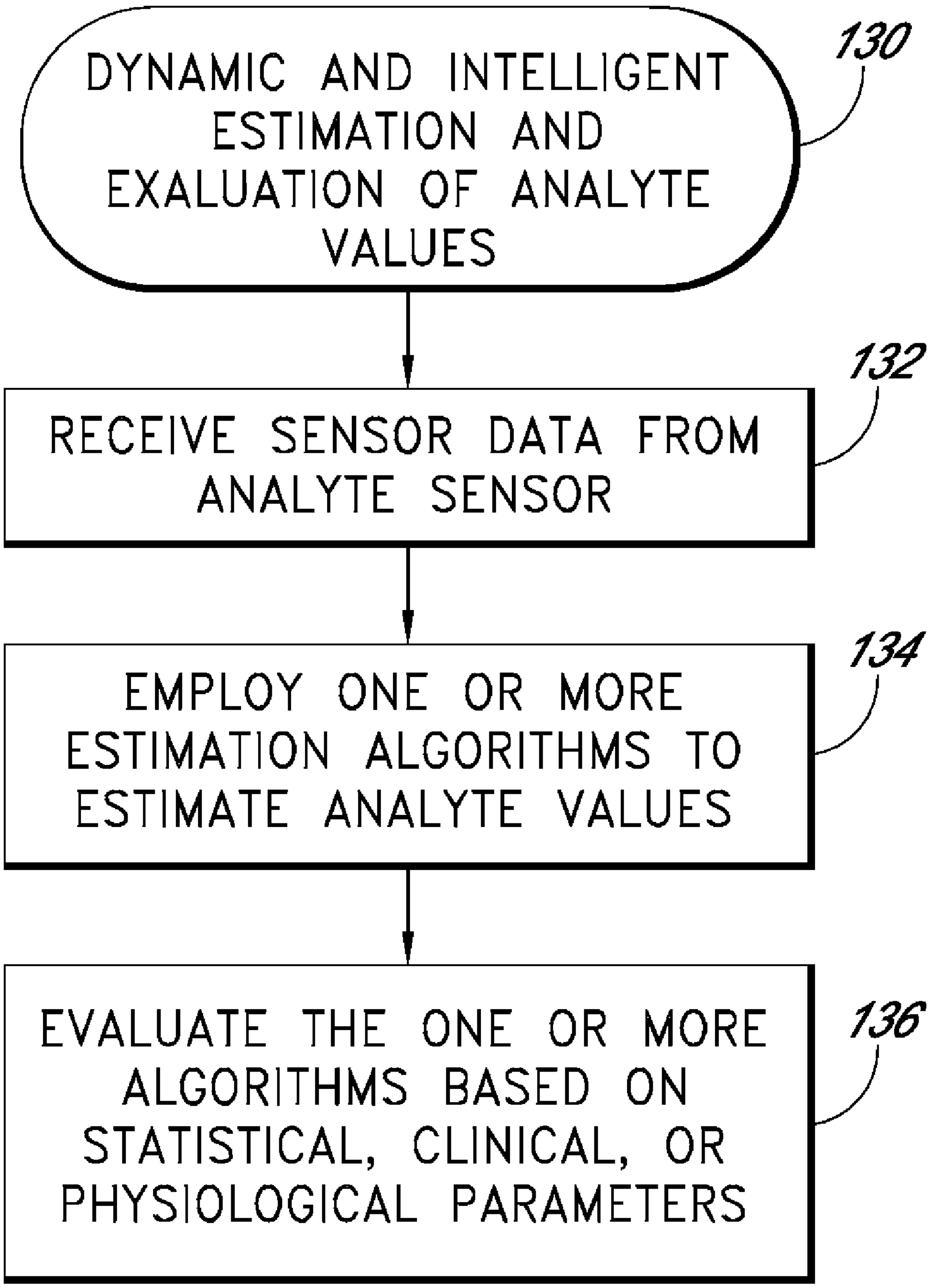
FIG. 13 is a flow chart that illustrates the process of dynamic and intelligent estimation and evaluation of analyte values in one embodiment.

FIG. 13 is a flow chart that illustrates the process 130 of dynamic and intelligent estimation and evaluation of analyte values in one embodiment, wherein the estimation algorithms are continuously, periodically, or intermittently evaluated based on statistical, clinical, or physiological parameters to maintain accuracy of estimation.

At block 132, the dynamic and intelligent estimation and evaluation process 130 obtains sensor data, which can be raw, smoothed, calibrated and/or otherwise processed.

At block 134, the dynamic and intelligent estimation and evaluation process 130 estimates one or more analyte values using one or more estimation algorithms. In some embodiments, this analyte value estimation uses conventional projection using first or second order regression, for example. In some embodiments, dynamically and intelligently selecting of one or more algorithms from a plurality of algorithms (FIG. 9), dynamically and intelligently estimating analyte values within physiological boundaries (FIG. 11), evaluating a variation of estimated analyte values (FIG. 15), measuring and comparing analyte values (FIG. 18), or the like can be applied to the dynamic and intelligent estimation and evaluation process described herein with reference to FIG. 13.

The estimative algorithms described elsewhere herein consider mathematical equations (FIG. 9) and optionally physiological parameters (FIG. 11), which may or may not be sufficient to accurately estimate analyte values in some circumstances due to the dynamic nature of mammalian behavior. For example, in a circumstance where a patient's glucose concentration is trending upwardly at a constant rate of change (for example, 120 mg/dL at 2 mg/dL/min), an expected physiological pattern would likely estimate a continued increase at substantially the same rate of change over the upcoming approximately 40 minutes, which would fall within physiological boundaries. However, if a person with diabetes were to engage in heavy aerobic exercise, which may not be known by the estimative algorithm, a slowing of the upward trend, and possibly a change to a downward trend can possibly result, leading to inaccuracies in the estimated analyte values. Numerous such circumstances can occur in the lifestyle of a person with diabetes. However, although analyte values can sometimes be estimated under "normal" circumstances, other circumstances exist that are not "normal" or "expected" and can result in estimative algorithms that produce apparently erroneous results, for example, if they are based solely on mathematical calculations and/or physiological patterns. Accordingly, evaluation of the estimative algorithms can be performed to ensure the accuracy or quantify a measure of confidence in the estimative algorithms.

At block 136, the dynamic and intelligent estimation and evaluation process 130 evaluates the estimation algorithms employed at block 134 to evaluate a "goodness" of the estimated analyte values. The evaluation process performs an evaluation of the measured analyte data with the corresponding estimated analyte data (e.g., by performing the algorithm on the data stream and comparing the measured with the corresponding analyte data for a time period). In some embodiments, evaluation can be performed continually or continuously so that the dynamic and intelligent algorithms are continuously adapting to the changing physiological analyte data. In some embodiments, the evaluation can be performed periodically so that the dynamic and intelligent algorithms are periodically and systematically adapting to the changing physiological analyte data. In some embodiments, evaluation can be performed intermittently, for example when an estimative algorithm is initiated or other such triggers, so that the dynamic and intelligent algorithms can be evaluated when new or updated data or algorithms are being processed.

This evaluation process 130 uses any known evaluation method, for example based on statistical, clinical, or physiological standards. One example of statistical evaluation is provided below with reference to FIG. 14; however other methods are also possible. In some embodiments, the evaluation process 130 determines a correlation coefficient of regression. In some embodiments wherein the sensor is a glucose sensor, the evaluation process 130 determines if the selected estimative algorithm shows that analyte values fall with the "A" and "B" regions of the Clarke Error Grid. Other parameters or methods for evaluation are considered within the scope of the preferred embodiments. In some embodiments, the evaluation process 130 includes performing a curvature formula to determine fiducial information about the curvature, which results in an evaluation of the amount of noise on the signal.

In some embodiments, the evaluation process 130 calculates physiological boundaries to evaluate whether the estimated analyte values fall within known physiological constraints. This evaluation is particularly helpful when physiological constraints, such as described with reference to FIG. 11 above, have not been applied to the estimative algorithm. In this embodiment, the estimative algorithm(s) are evaluated to ensure that they do not allow estimated analyte values to fall outside of physiological boundaries, some examples of which are described in more detail with reference to FIG. 11 above, and in the definitions section, for example. In some alternative embodiments, clinical or statistical parameters can be used in a similar manner to bound estimated analyte values.

If the result of the evaluation is satisfactory (for example, 10% average deviation, correlation coefficient above 0.79, all estimated analyte values within A or B region of the Clarke Error Grid, all estimated analyte values within physiological boundaries, or the like), the processing continues to the next step, using the selected estimative algorithm. However, if the result of the evaluation is unsatisfactory, the process can start the algorithm selection process again, optionally considering additional information, or the processor can determine that estimation is not appropriate for a certain time period. In one alternative embodiment, a signal noise measurement can be evaluated, and if the signal to noise ratio is unacceptable, the processor can modify its estimative algorithm or other action that can help compensate for signal noise (e.g., signal artifacts, such as described in co-pending U.S. application Ser. No. 10/632,537 filed Aug. 22, 2003 and entitled, "SYSTEMS AND METHODS FOR REPLACING SIGNAL ARTIFACTS IN A GLUCOSE SENSOR DATA STREAM," which is incorporated herein by reference in its entirety).

Figure 14:
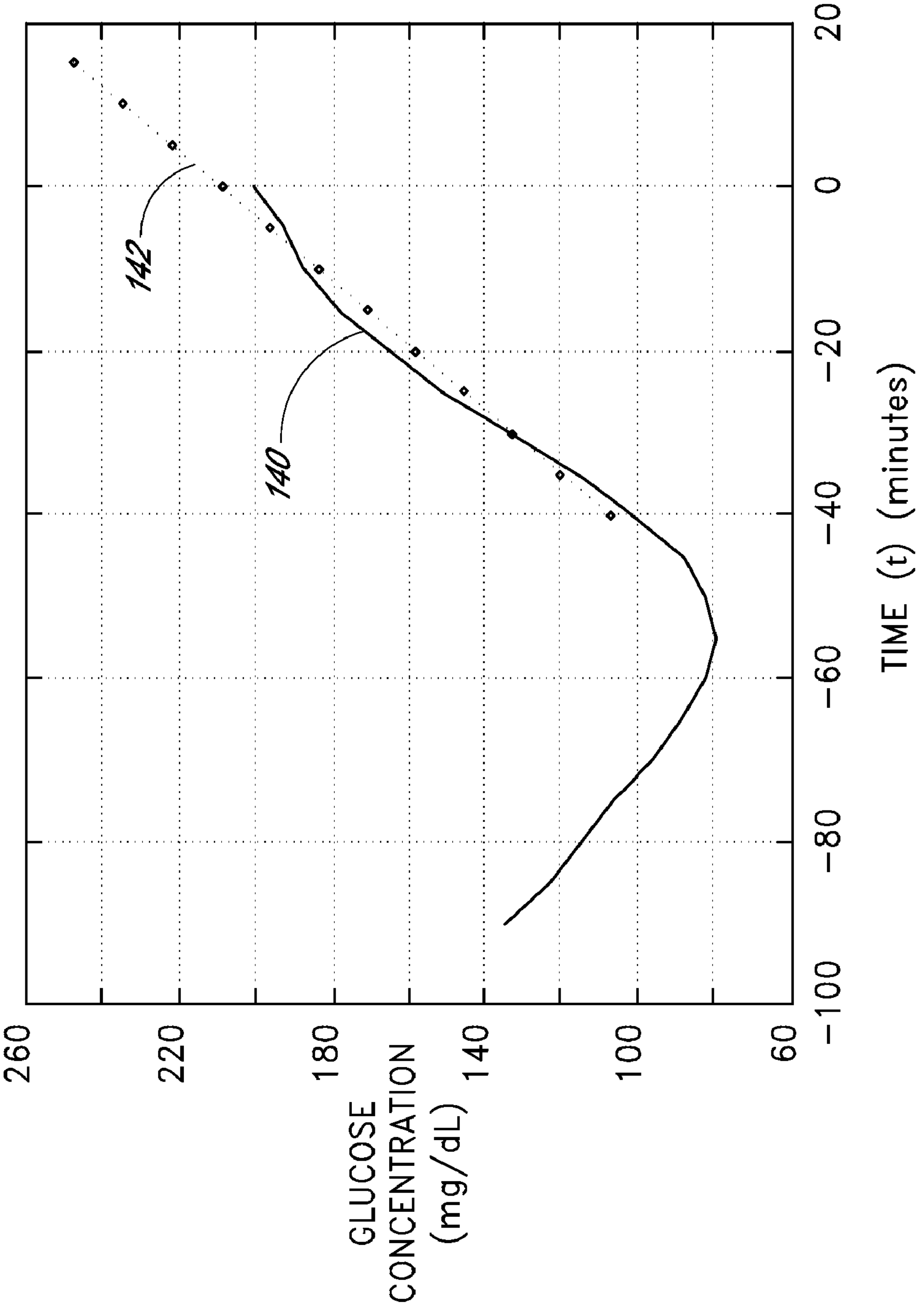
FIG. 14 is a graph that illustrates a case wherein the selected estimative algorithm is evaluated in one embodiment, wherein a correlation is measured to determine a deviation of the measured analyte data with the selected estimative algorithm, if any.

FIG. 14 is a graph that illustrates an evaluation of the selected estimative algorithm in one embodiment, wherein a correlation is measured to determine a deviation of the measured glucose data with the selected estimative algorithm, if any. The x-axis represents time in minutes. The y-axis represents glucose concentration in mg/dL. Measured glucose values 140 are shown for about 90 minutes up to t=0. At t=0, the selected algorithm is performed on 40 minutes of the measured glucose values 140 up to t=0, which is represented by a regression line 142 in this embodiment. A data association function is used to determine a goodness of fit of the estimative algorithm on the measured glucose data 140; namely, the estimative algorithm is performed retrospectively on the measured glucose data 140, and is hereinafter referred to as retrospectively estimated glucose data 142 (e.g., estimation prior to t=0), after which a correlation (or deviation) with the measured glucose data is determined. In this example, the goodness of fit shows a mean absolute relative difference (MARD) of 3.3% between the measured glucose data 140 and the retrospectively estimated glucose data 142. While not wishing to be bound to theory, it is believed that this correlation of the measured glucose data 140 to the retrospectively estimated glucose data 142 can be indicative of the correlation of future estimated glucose data to the measured glucose data for that estimated time period.

Figure 15:
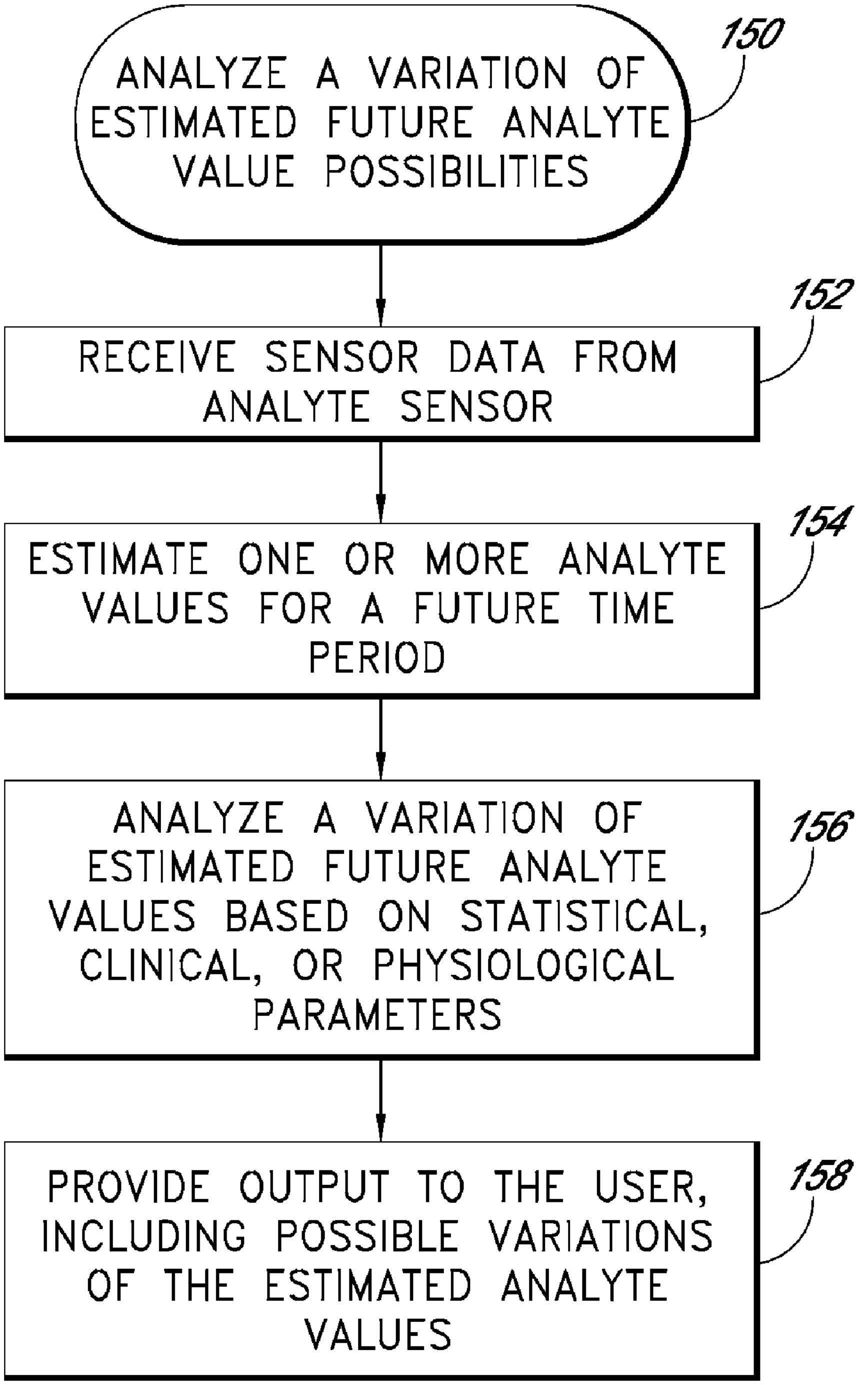
FIG. 15 is a flow chart that illustrates the process of evaluating a variation of estimated future analyte value possibilities in one embodiment.

Reference is now made to FIG. 15, which is a flow chart that illustrates the process 150 of analyzing a variation of estimated future analyte value possibilities in one embodiment. This embodiment takes into consideration that analyte values are subject to a variety of external influences, which can cause the measured analyte values to alter from the estimated analyte values as the time period that was estimated passes. External influences include, but are not limited to, exercise, sickness, consumption of food and alcohol, injections of insulin, other medications, or the like. For a person with diabetes, for example, even when estimation does not accurately predict the upcoming measured analyte values, the estimated analyte values can be valuable to a patient in treatment and in fact can even alter the estimated path by encouraging proactive patient behavior that can cause the patient to avoid the estimated clinical risk. In other words, the deviation of measured analyte values from their corresponding estimated analyte values may not be an "error" in the estimative algorithm, and is in fact one of the benefits of the continuous analyte sensor of the preferred embodiments, namely encouraging patient behavior modification and thereby improving patient health through minimizing clinically risky analyte values. Proactive behavior modification (for example, therapies such as insulin injections, carbohydrate consumption, exercise, or the like) can cause the patient's measured glucose to change from the estimated path, and analyzing a variation that can be associated with the estimated analyte values can encompass many of these changes. Therefore, in addition to estimated analyte values, a variation can be calculated or estimated based on statistical, clinical, and/or physiological parameters that provides a range of values in which the estimated analyte values can fall.

At block 152, the variation of possible estimated analyte values analysis process 150 obtains sensor data, which can be raw, smoothed, calibrated and/or otherwise processed.

At block 154, the variation of possible estimated analyte values analysis process 150 estimates one or more analyte values using one or more estimation algorithms. In some embodiments, this analyte values estimation uses conventional projection using first or second order regression, for example. In some embodiments, dynamically and intelligently selecting of one or more algorithms from a plurality of algorithms (FIG. 9), dynamically and intelligently estimating analyte values within physiological boundaries (FIG. 11), dynamic and intelligent estimation and evaluation of estimated analyte values (FIG. 13), measuring and comparing analyte values (FIG. 18), or the like can be applied to the dynamic and intelligent estimation and evaluation process described herein with reference to FIG. 15.

At block 156, the variation of possible estimated analyte values evaluation process 150 analyzes a variation of the estimated analyte data. Particularly, a statistical, clinical, and/or physiological variation of estimated analyte values can be calculated when applying the estimative algorithms and/or can be calculated at regular intervals to dynamically change as the measured analyte values are obtained. In general, analysis of trends and their variation allows the estimation of the preferred embodiments to dynamically and intelligently anticipate upcoming conditions, by considering internal and external influences that can affect analyte concentration.

In some embodiments, physiological boundaries for analytes in mammals can be used to set the boundaries of variation. For example, known physiological boundaries of glucose in humans are discussed in detail herein, with reference to FIG. 11, and in the definitions section, however any physiological parameters for any measured analyte could be implemented here to provide this variation of physiologically feasible analyte values.

In some embodiments, statistical variation can be used to determine a variation of possible analyte values. Statistical variation can be any known divergence or change from a point, line, or set of data based on statistical information. Statistical information includes patterns or data analysis resulting from experiments, published or unpublished, for example. In some embodiments, statistical information can include normal patterns that have been measured statistically in studies of analyte concentrations in mammals, for example. In some embodiments, statistical information can include errors observed and measured statistically in studies of analyte concentrations in mammals, for example. In some embodiments, statistical information can include predetermined statistical standards, for example, deviation less than or equal to 5% on the analyte value. In some embodiments, statistical variation can be a measured or otherwise known signal noise level.

In some embodiments, a variation is determined based on the fact that the conventional blood glucose meters are known to have up to a +/−20% error in glucose values (namely, on average in the hands of a patient). For example, gross errors in glucose readings are known to occur due to patient error in self-administration of the blood glucose test. In one such example, if the user has traces of sugar on his/her finger while obtaining a blood sample for a glucose concentration test, then the measured glucose value will likely be much higher than the measured glucose value in the blood. Additionally, it is known that self-monitored blood glucose tests (for example, test strips) are occasionally subject to manufacturing error. In view of this statistical information, in an embodiment wherein a continuous glucose sensor relies upon a conventional blood glucose meter for calibration, this +/−20% error should be considered because of the potential for translated effect on the calibrated sensor analyte data. Accordingly, this exemplary embodiment would provide for a +/−20% variation of estimated glucose values based on the above-described statistical information.

In some embodiments, a variation of estimated analyte values can be analyzed based on individual physiological patterns. Physiological patterns are affected by a combination of at least biological mechanisms, physiological boundaries, and external influences such as exercise, sickness, consumption of food and alcohol, injections of insulin, other medications, or the like. Advantageously, pattern recognition can be used with continuous analyte sensors to characterize an individual's physiology; for example the metabolism of a person with diabetes can be individually characterized, which has been difficult to quantify with conventional glucose sensing mechanisms due to the unique nature of an individual's metabolism. Additionally, this information can be advantageously linked with external influences (for example, patient behavior) to better understand the nature of individual human physiology, which can be helpful in controlling the basal rate in a person with diabetes, for example.

While not wishing to be bound to theory, it is believed that monitoring of individual historical physiological analyte data can be used to recognize patterns that can be used to estimate analyte values, or ranges of values, in a mammal. For example, measured analyte data for a patient can show certain peaks of glucose levels during a specific time of day, "normal" AM and PM eating behaviors (for example, that follow a pattern), weekday versus weekend glucose patterns, individual maximum rate of change, or the like, that can be quantified using patient-dependent pattern recognition algorithms, for example. Pattern recognition algorithms that can be used in this embodiment include, but are not limited to, stochastic nonlinear time-series analysis, exponential (nonlinear) autoregressive model, process feedback nonlinear autoregressive (PFNAR) model, neural networks, or the like.

Accordingly, statistically calculated patterns can provide information useful in analyzing a variation of estimated analyte values for a patient that includes consideration of the patient's normal physiological patterns. Pattern recognition enables the algorithmic analysis of analyte data to be customized to a user, which is useful when analyte information is variable with each individual user, such as has been seen in glucose in humans, for example.

In some embodiments, a variation of estimated analyte values is on clinical risk analysis. Estimated analyte values can have higher clinical risk in certain ranges of analyte values, for example analyte values that are in a clinically risky zone or analyte values that are changing at a clinically risky rate of change. When a measured analyte value or an estimated analyte value shows existing or approaching clinical risk, it can be important to analyze the variation of estimated analyte values in view of the clinical risk to the patient. For example, in an effort to aid a person with diabetes in avoiding clinically risky hyper- or hypoglycemia, a variation can be weighted toward the clinically risk zone, which can be used to emphasize the pending danger to the patient, doctor, or care taker, for example. As another example, the variation of measured or estimated analyte values can be based on values that fall within the "A" and/or "B" regions of an error grid Analysis Method.

In case of variation analysis based on clinical risk, the estimated analyte values are weighted in view of pending clinical risk. For example, if estimated glucose values show a trend toward hypoglycemia at a certain rate of change, a variation of possible trends toward hypoglycemia are weighted to show how quickly the glucose concentration could reach 40 mg/dL, for example. As another example, if estimated glucose values show a trend toward hyperglycemia at a certain acceleration, a variation of possible trends toward hyperglycemia are weighted to show how quickly the glucose concentration could reach 200 mg/dL, for example.

In some embodiments, when a variation of the estimated analyte values shows higher clinical risk as a possible path within that variation analysis as compared to the estimated analyte path, the estimated analyte values can be adjusted to show the analyte values with the most clinical risk to a patient. While not wishing to be bound by theory, adjusting the estimated analyte values for the highest variation of clinical risk exploits the belief that by showing the patient the "worst case scenario," the patient is more likely to address the clinical risk and make timely behavioral and therapeutic modifications and/or decisions that will slow or reverse the approaching clinical risk.

Figure 24:
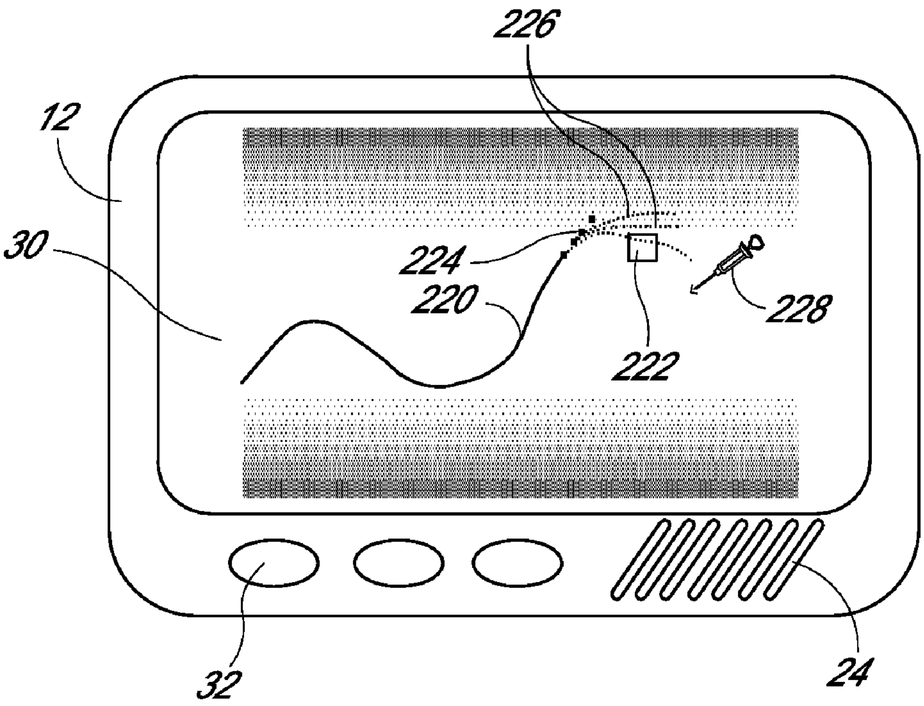
FIG. 24 is an illustration of the receiver of FIG. 23, further including a variation of estimated analyte values and therapy recommendations on the same screen to help the user obtain the displayed target analyte values.
Figure 25:
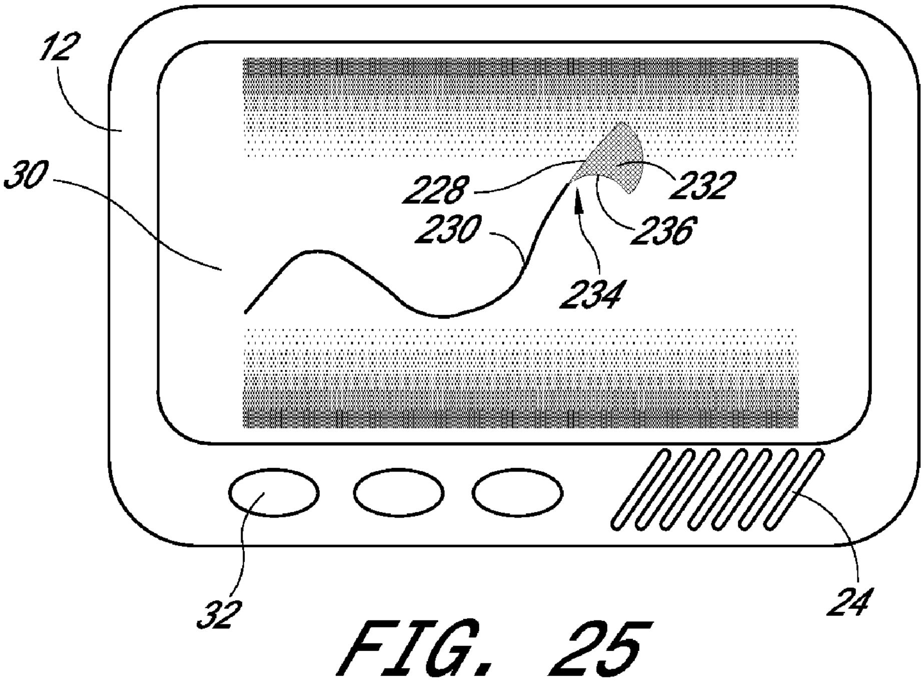
FIG. 25 is an illustration of the receiver in one embodiment, showing measured analyte values and a dynamic visual representation of a range of estimated analyte values based on a variation analysis.
Figure 26:
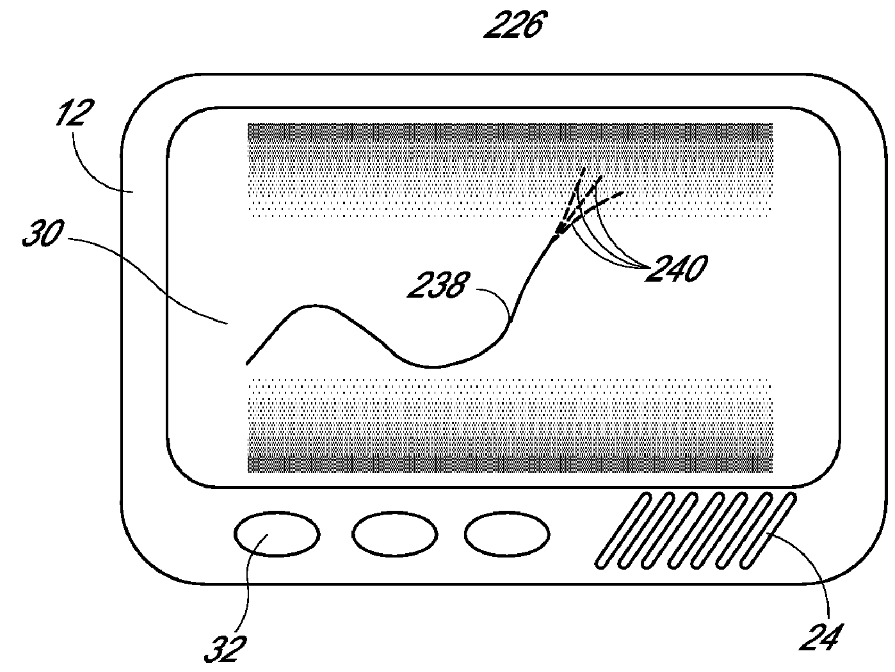
FIG. 26 is an illustration of the receiver in another embodiment, showing measured analyte values and a visual representation of range of estimated analyte values based on a variation analysis.

At block 158, the variation of possible estimated analyte values evaluation process 150 provides output based on the variation analysis. In some embodiments, the result of this variation analysis provides a "zone" of possible values, which can be displayed to the user, considered in data analysis, and/or used in evaluating of performance of the estimation, for example. A few examples of variation analysis display are shown in FIGS. 24 to 26; however other methods of formatting or displaying variation analysis data are contemplated within the scope of the invention.

Figure 16:
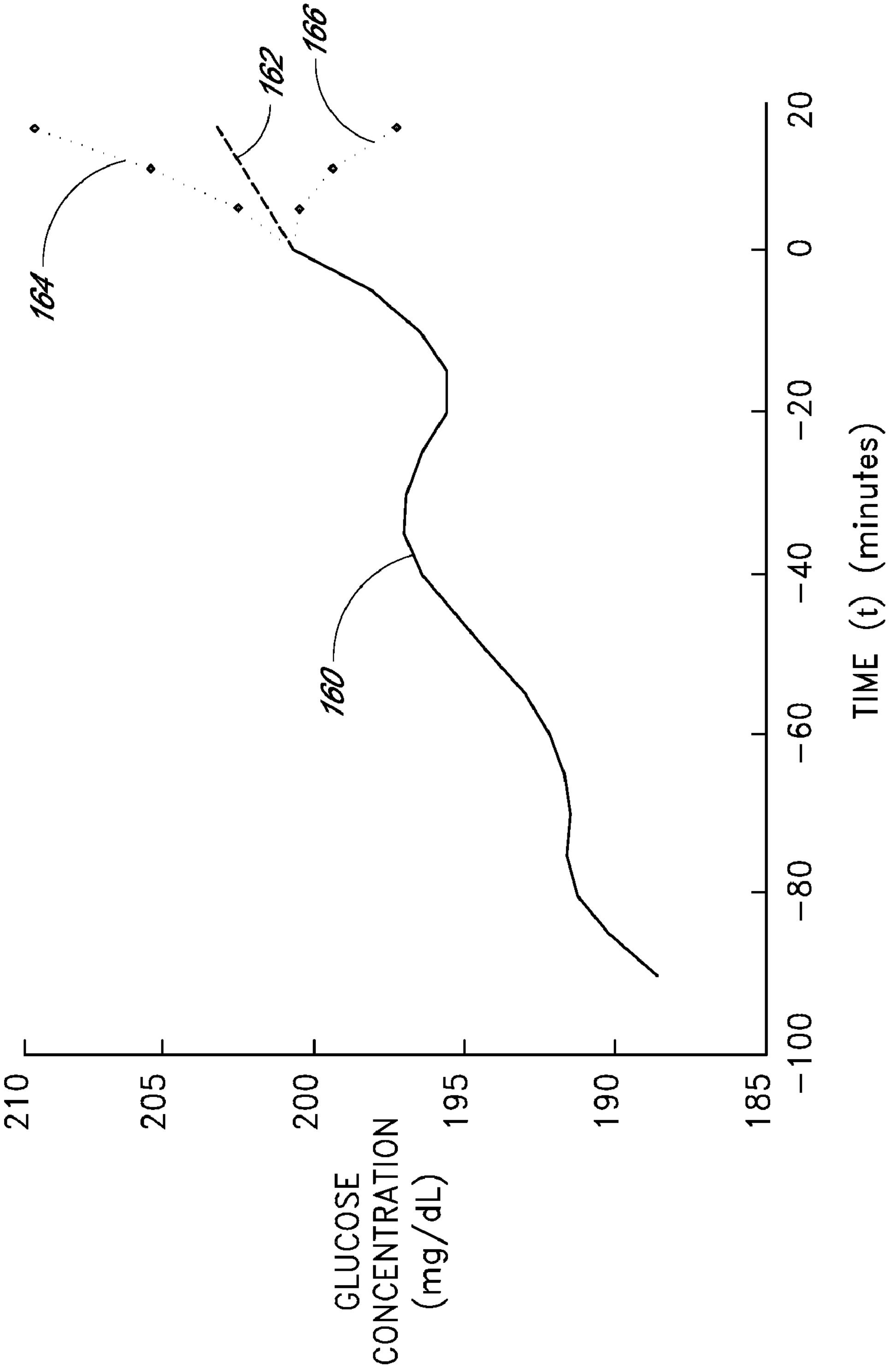
FIG. 16 is a graph that illustrates a case wherein a variation of estimated analyte values is based on physiological parameters.

FIG. 16 is a graph that illustrates variation analysis of estimated glucose values in one embodiment, wherein a variation of the estimated glucose values is analyzed and determined based on known physiological parameters. The x-axis represents time in minutes. The y-axis represents glucose concentration in mg/dL. In this embodiment, the known maximum rate of change and acceleration of glucose in humans are used to provide the variation about the estimated glucose path.

The measured glucose values 160 are shown for about 90 minutes up to t=0. At t=0, intelligent and dynamic estimation of the preferred embodiments is performed to obtain estimated glucose values 162. A variation of estimated glucose values is then determined based on physiological parameters, including an upper limit 164 and a lower limit 166 of variation defined by known physiological parameters, including rate of change and acceleration of glucose concentration in humans.

Figure 17:
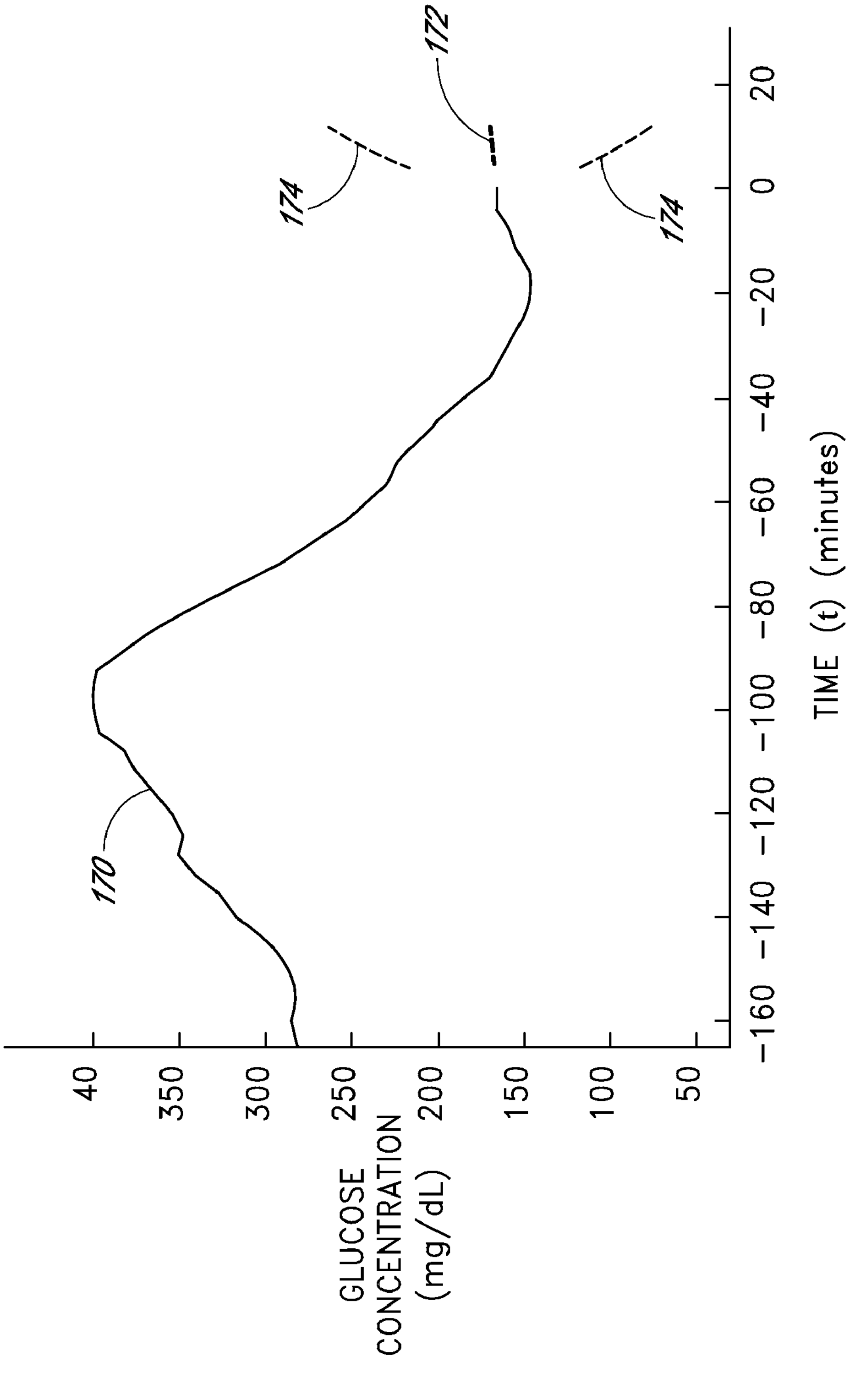
FIG. 17 is a graph that illustrates a case wherein a variation of estimated analyte values is based on statistical parameters.

FIG. 17 is a graph that illustrates variation of estimated analyte values in another embodiment, wherein the variation is based on statistical parameters. The x-axis represents time in minutes and the y-axis represents glucose concentration in mg/dL. The measured glucose values 170 are shown for about 160 minutes up to t=0. At t=0, intelligent and dynamic estimation of the preferred embodiments is employed to obtain estimated glucose values 172. A variation is defined by upper and lower limits 174 that were determined using 95% confidence intervals. Bremer, T.; Gough, D. A. "Is blood glucose predictable from previous values? A solicitation for data." *Diabetes* 1999, 48, 445-451, which is incorporated by reference herein in its entirety, teaches a method of determining a confidence interval in one embodiment.

Although some embodiments have been described for a glucose sensor, any measured analyte pattern, data analysis resulting from an experiment, or otherwise known statistical information, whether official or unofficial, published or unpublished, proven or anecdotal, or the like, can be used to provide the statistical variation described herein.

Figure 18:
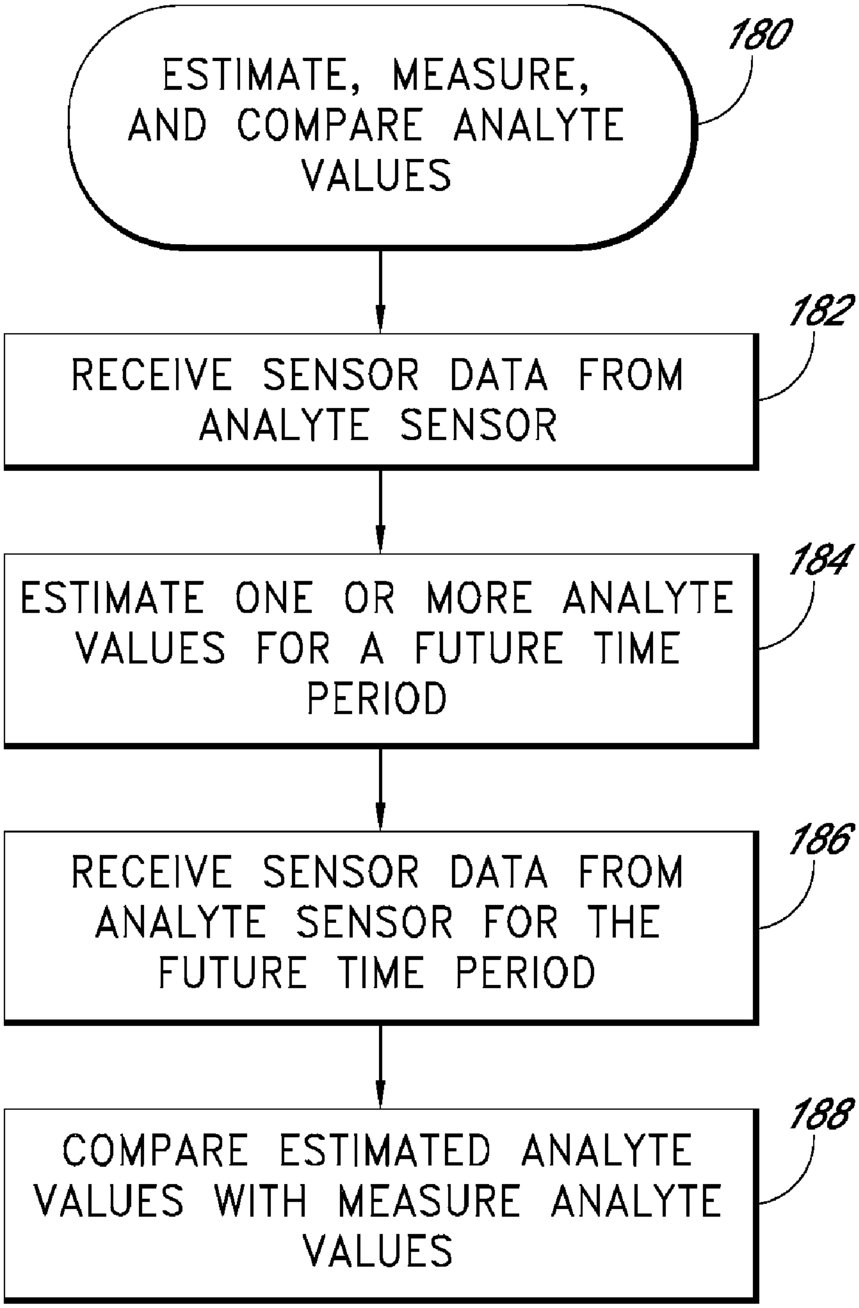
FIG. 18 is a flow chart that illustrates the process of estimating, measuring, and comparing analyte values in one embodiment.

FIG. 18 is a flow chart that illustrates the process 180 of estimating, measuring, and comparing analyte values in one embodiment.

At block 182, the estimating, measuring, and comparing analyte values process 180 obtains sensor data, which can be raw, smoothed, calibrated and/or otherwise processed.

At block 184, the estimating, measuring, and comparing analyte values process 180 estimates one or more analyte values for a time period. In some embodiments, this analyte values estimation uses conventional projection using first or second order regression, for example. In some embodiments, dynamically and intelligently selecting of one or more algorithms from a plurality of algorithms (FIG. 9), dynamically and intelligently estimating analyte values within physiological boundaries (FIG. 11), dynamic and intelligent estimation and evaluation of estimated analyte values (FIG. 13), variation analysis (FIG. 15), or the like can be applied to the process described herein with reference to FIG. 18.

At block 186, the estimating, measuring, and comparing analyte values process 180 obtains sensor data for the time period for which the estimated analyte values were calculated at block 184. In some embodiments, the measured analyte data can be raw, smoothed, calibrated and/or otherwise processed.

At block 188, the estimating, measuring, and comparing analyte values process 180 compares the estimated analyte data to the measured analyte data for that estimated time period. In general, it can be useful to compare the estimated analyte data to the measured analyte data for that estimated time period after estimation of analyte values. This comparison can be performed continuously, namely, at regular intervals as data streams are processed into measured analyte values. Alternatively, this comparison can be performed based on events, such as during estimation of measured analyte values, selection of a estimative algorithm, evaluation of estimative algorithms, variation analysis of estimated analyte values, calibration and transformation of sensor analyte data, or the like.

Figure 19:
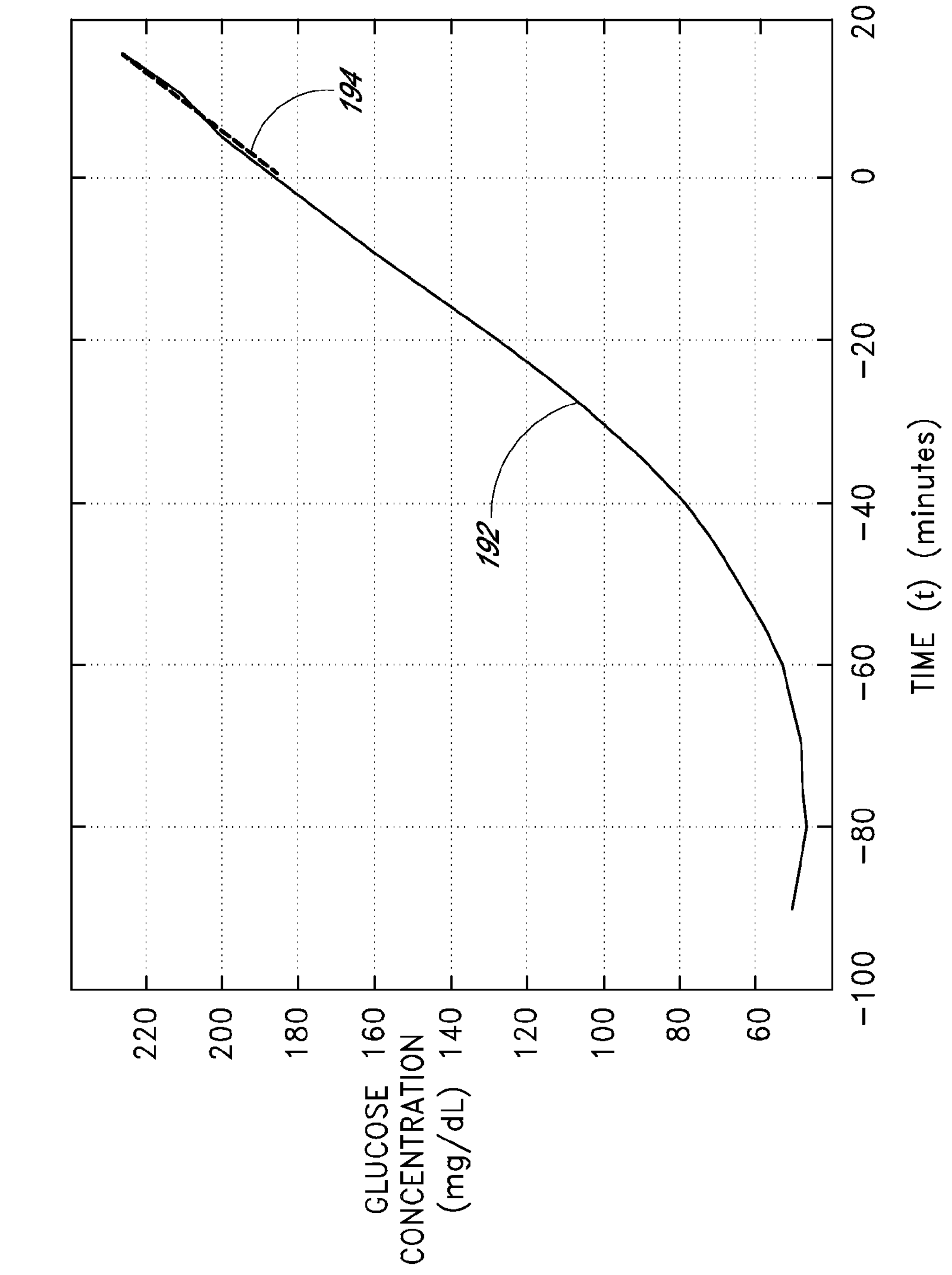
FIG. 19 is a graph that illustrates a case wherein a comparison of estimated analyte values to time corresponding measured analyte values is used to determine correlation of estimated to measured analyte data.

One embodiment is shown in FIG. 19, wherein MARD is used to determine a correlation (or deviation), if any, between the estimated and measured data sets. In other embodiments, other methods, such as linear regression, non-linear mapping/regression, rank (for example, non-parametric) correlation, least mean square fit, mean absolute deviation (MAD), or the like, can be used to compare the estimated analyte data to the measured analyte data to determine a correlation (or deviation), if any.

In one embodiment, wherein estimation is used in outlier detection and/or in matching data pairs for a continuous glucose sensor (see FIGS. 6 and 7), the estimated glucose data can be plotted against reference glucose data on a clinical error grid (for example, Clarke Error Grid or rate grid) and then compared to the measured glucose data for that estimated time period plotted against the same reference analyte data on the same clinical error grid. In alternative embodiments, other clinical error analysis methods can be used, such as Consensus Error Grid, rate of change calculation, consensus grid, and standard clinical acceptance tests, for example. The deviation can be quantified by percent deviation, or can be classified as pass/fail, for example.

In some embodiments, the results of the comparison provide a quantitative deviation value, which can be used to provide a statistical variation; for example, if the % deviation is calculated as 8%, then the statistical variation such as described with reference to FIG. 15 can be updated with a +/−8% variation. In some alternative embodiments, the results of the comparison can be used to turn on/off the estimative algorithms, estimative output, or the like. In general, the comparison produces a confidence interval (for example, +/−8% of estimated values) which can be used in data analysis, output of data to a user, or the like.

A resulting deviation from this comparison between estimated and corresponding measured analyte values may or may not imply error in the estimative algorithms. While not wishing to be bound by theory, it is believed that the deviation between estimated and corresponding measured analyte values is due, at least in part, to behavioral changes by a patient, who observes estimated analyte values and determines to change the present trend of analyte values by behavioral and/or therapeutic changes (for example, medication, carbohydrate consumption, exercise, rest, or the like). Accordingly, the deviation can also be used to illustrate positive changes resulting from the educational aspect of providing estimated analyte values to the user, which is described in more detail with reference to FIGS. 20 to 26.

FIG. 19 is a graph that illustrates comparison of estimated analyte values in one embodiment, wherein previously estimated analyte values are compared to time corresponding measured analyte values to determine a correlation (or deviation), if any. The x-axis represents time in minutes. The y-axis represents glucose concentration in mg/dL. The measured glucose values 192 are shown for about 105 minutes up to t=15. The estimated analyte values 194, which were estimated at t=0 for 15 minutes, are shown superimposed over the measured analyte values 192. Using a 3-point MARD for t=0 to t=15, the estimated analyte values 194 can be compared with the measured analyte values 192 to determine a 0.55% average deviation.

Input and Output

In general, the above-described estimative algorithms, including estimation of measured analyte values and variation analysis of the estimated analyte values are useful when provided to a patient, doctor, family member, or the like. Even more, the estimative algorithms are useful when they are able to provide information helpful in modifying a patient's behavior so that they experience less clinically risky situations and higher quality of life than may otherwise be possible. Therefore, the above-described data analysis can be output in a variety of forms useful in caring for the health of a patient.

Output can be provided via a user interface, including but not limited to, visually on a screen, audibly through a speaker, or tactilely through a vibrator. Additionally, output can be provided via wired or wireless connection to an external device, including but not limited to, computer, laptop, server, personal digital assistant, modem connection, insulin delivery mechanism, medical device, or other device that can be useful in interfacing with the receiver.

Output can be continuously provided, or certain output can be selectively provided based on events, analyte concentrations or the like. For example, an estimated analyte path can be continuously provided to a patient on an LCD screen, while audible alerts can be provided only during a time of existing or approaching clinical risk to a patient. As another example, estimation can be provided based on event triggers (for example, when an analyte concentration is nearing or entering a clinically risky zone). As yet another example, analyzed deviation of estimated analyte values can be provided when a predetermined level of variation (for example, due to known error or clinical risk) is known.

In contrast to alarms that prompt or alert a patient when a measured or projected analyte value or rate of change simply passes a predetermined threshold, the clinical risk alarms of the preferred embodiments combine intelligent and dynamic estimative algorithms to provide greater accuracy, more timeliness in pending danger, avoidance of false alarms, and less annoyance for the patient. In general, clinical risk alarms of the preferred embodiments include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms.

In some embodiments, clinical risk alarms can be activated for a predetermined time period to allow for the user to attend to his/her condition. Additionally, the clinical risk alarms can be de-activated when leaving a clinical risk zone so as not to annoy the patient by repeated clinical risk alarms, when the patient's condition is improving.

In some embodiments, the dynamic and intelligent estimation of the preferred embodiments determines a possibility of the patient avoiding clinical risk, based on the analyte concentration, the rate of change, and other aspects of the dynamic and intelligent estimative algorithms of the preferred embodiments. If there is minimal or no possibility of avoiding the clinical risk, a clinical risk alarm will be triggered. However, if there is a possibility of avoiding the clinical risk, the system can wait a predetermined amount of time and re-analyze the possibility of avoiding the clinical risk. In some embodiments, when there is a possibility of avoiding the clinical risk, the system will further provide targets, therapy recommendations, or other information that can aid the patient in proactively avoiding the clinical risk.

In some embodiments, a variety of different display methods are used, such as described in the preferred embodiments, which can be toggled through or selectively displayed to the user based on conditions or by selecting a button, for example. As one example, a simple screen can be normally shown that provides an overview of analyte data, for example present analyte value and directional trend. More complex screens can then be selected when a user desired more detailed information, for example, historical analyte data, alarms, clinical risk zones, or the like.

Figure 20:
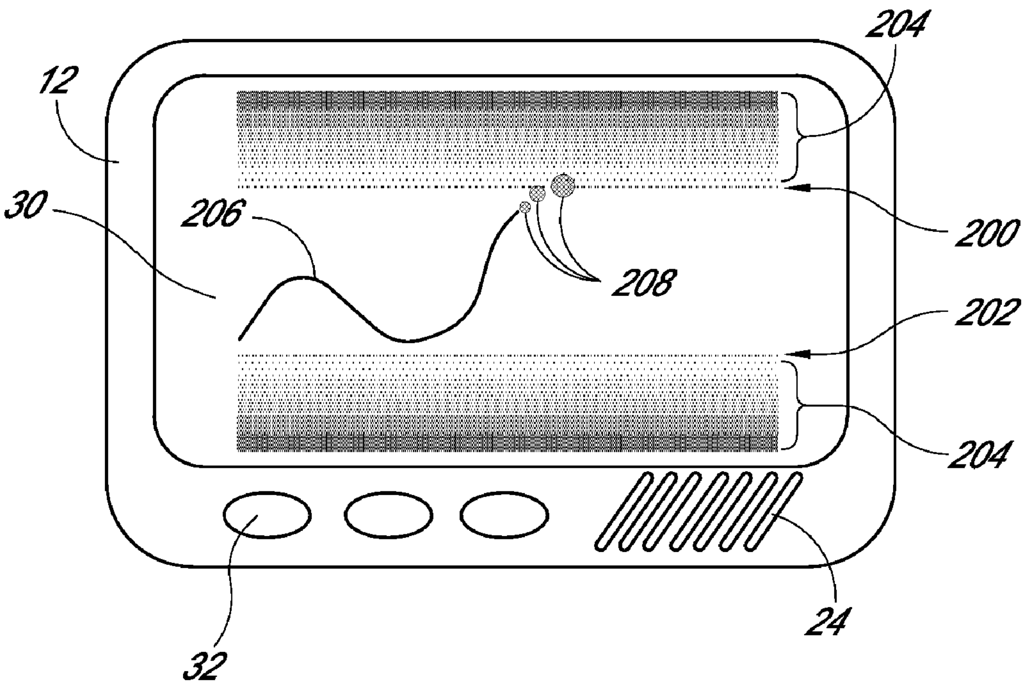
FIG. 20 is an illustration of the receiver in one embodiment showing an analyte trend graph, including measured analyte values, estimated analyte values, and a zone of clinical risk.

FIG. 20 is an illustration of the receiver in one embodiment showing an analyte trend graph, including measured analyte values, estimated analyte values, and a clinical risk zone. The receiver 12 includes an LCD screen 30, buttons 32, and a speaker 24 and/or microphone. The screen 30 displays a trend graph in the form of a line representing the historical trend of a patient's analyte concentration. Although axes may or may not be shown on the screen 30, it is understood that a theoretical x-axis represents time and a theoretical y-axis represents analyte concentration.

In some embodiments such as shown in FIG. 20, the screen shows thresholds, including a high threshold 200 and a low threshold 202, which represent boundaries between clinically safe and clinically risky conditions for the patients. In one exemplary embodiment, a normal glucose threshold for a glucose sensor is set between about 100 and 160 mg/dL, and the clinical risk zones 204 are illustrated outside of these thresholds. In alternative embodiments, the normal glucose threshold is between about 80 and about 200 mg/dL, between about 55 and about 220 mg/dL, or other threshold that can be set by the manufacturer, physician, patient, computer program, or the like. Although a few examples of glucose thresholds are given for a glucose sensor, the setting of any analyte threshold is not limited by the preferred embodiments.

In some embodiments, the screen 30 shows clinical risk zones 204, also referred to as danger zones, through shading, gradients, or other graphical illustrations that indicate areas of increasing clinical risk. Clinical risk zones 204 can be set by a manufacturer, customized by a doctor, and/or set by a user via buttons 32, for example. In some embodiments, the danger zone 204 can be continuously shown on the screen 30, or the danger zone can appear when the measured and/or estimated analyte values fall into the danger zone 204. Additional information that can be displayed on the screen, such as an estimated time to clinical risk. In some embodiments, the danger zone can be divided into levels of danger (for example, low, medium, and high) and/or can be color-coded (for example, yellow, orange, and red) or otherwise illustrated to indicate the level of danger to the patient. Additionally, the screen or portion of the screen can dynamically change colors or illustrations that represent a nearness to the clinical risk and/or a severity of clinical risk.

In some embodiments, such as shown in FIG. 20, the screen 30 displays a trend graph of measured analyte data 206. Measured analyte data can be smoothed and calibrated such as described in more detail elsewhere herein. Measured analyte data can be displayed for a certain time period (for example, previous 1 hour, 3 hours, 9 hours, etc.) In some embodiments, the user can toggle through screens using buttons 32 to view the measured analyte data for different time periods, using different formats, or to view certain analyte values (for example, highs and lows).

In some embodiments such as shown in FIG. 20, the screen 30 displays estimated analyte data 208 using dots. In this illustration, the size of the dots can represent the confidence of the estimation, a variation of estimated values, or the like. For example, as the time gets farther away from the present (t=0) the confidence level in the accuracy of the estimation can decline as is appreciated by one skilled in the art. In some alternative embodiments, dashed lines, symbols, icons, or the like can be used to represent the estimated analyte values. In some alternative embodiments, shaded regions, colors, patterns, or the like can also be used to represent the estimated analyte values, a confidence in those values, and/or a variation of those values, such as described in more detail in preferred embodiments.

Axes, including time and analyte concentration values, can be provided on the screen, however are not required. While not wishing to be bound by theory, it is believed that trend information, thresholds, and danger zones provide sufficient information to represent analyte concentration and clinically educate the user. In some embodiments, time can be represented by symbols, such as a sun and moon to represent day and night. In some embodiments, the present or most recent measured analyte concentration, from the continuous sensor and/or from the reference analyte monitor can be continually, intermittently, or selectively displayed on the screen.

The estimated analyte values 208 of FIG. 20 include a portion, which extends into the danger zone 204. By providing data in a format that emphasizes the possibility of clinical risk to the patient, appropriate action can be taken by the user (for example, patient or caretaker) and clinical risk can be preempted.

Figure 21:
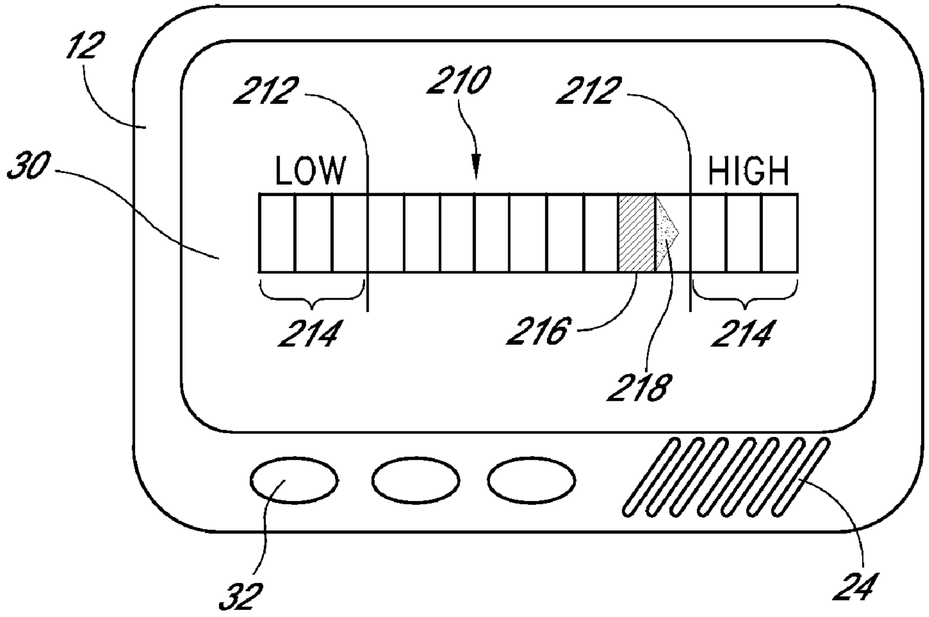
FIG. 21 is an illustration of the receiver in one embodiment showing a gradient bar, including measured analyte values, estimated analyte values, and a zone of clinical risk.

FIG. 21 is an illustration of the receiver in another embodiment showing a representation of analyte concentration and directional trend using a gradient bar. In this embodiment, the screen illustrates the measured analyte values and estimated analyte values in a simple but effective manner that communicates valuable analyte information to the user.

In this embodiment, a gradient bar 210 is provided that includes thresholds 212 set at high and lows such as described in more detail with reference to FIG. 20, above. Additionally, colors, shading, or other graphical illustration can be present to represent danger zones 214 on the gradient bar 210 such as described in more detail with reference to FIG. 20, above.

The measured analyte value is represented on the gradient bar 210 by a marker 216, such as a darkened or colored bar. By representing the measured analyte value with a bar 216, a low-resolution analyte value is presented to the user (for example, within a range of values). For example, each segment on the gradient bar 210 can represent about 10 mg/dL of glucose concentration. As another example, each segment can dynamically represent the range of values that fall within the "A" and "B" regions of the Clarke Error Grid. While not wishing to be bound by theory, it is believe that inaccuracies known both in reference analyte monitors and/or continuous analyte sensors are likely due to known variables such as described in more detail elsewhere herein, and can be de-emphasized such that a user focuses on proactive care of the condition, rather than inconsequential discrepancies within and between reference analyte monitors and continuous analyte sensors.

Additionally, the representative gradient bar communicates the directional trend of the analyte concentration to the user in a simple and effective manner, namely by a directional arrow 218. For example, in conventional diabetic blood glucose monitoring, a person with diabetes obtains a blood sample and measures the glucose concentration using a test strip, or the like. Unfortunately, this information does not tell the person with diabetes whether the blood glucose concentration is rising or falling. Rising or falling directional trend information can be particularly important in a situation such as illustrated in FIG. 21, wherein if the user does not know that the glucose concentration is rising, he/she may assume that the glucose concentration is falling and not attend to his/her condition. However, because rising directional trend information 218 is provided, the person with diabetes can preempt the clinical risk by attending to his/her condition (for example, administer insulin). Estimated analyte data can be incorporated into the directional trend information by characteristics of the arrow, for example, size, color, flash speed, or the like.

In some embodiments, the gradient bar can be a vertical instead of horizontal bar. In some embodiments, a gradient fill can be used to represent analyte concentration, variation, or clinical risk, for example. In some embodiments, the bar graph includes color, for example the center can be green in the safe zone that graduates to red in the danger zones; this can be in addition to or in place of the divided segments. In some embodiments, the segments of the bar graph are clearly divided by lines; however color, gradation, or the like can be used to represent areas of the bar graph. In some embodiments, the directional arrow can be represented by a cascading level of arrows to a represent slow or rapid rate of change. In some embodiments, the directional arrow can be flashing to represent movement or pending danger.

The screen 30 of FIG. 21 can further comprise a numerical representation of analyte concentration, date, time, or other information to be communicated to the patient. However, a user can advantageously extrapolate information helpful for his/her condition using the simple and effective representation of this embodiment shown in FIG. 21, without reading a numeric representation of his/her analyte concentration.

In some alternative embodiments, a trend graph or gradient bar, a dial, pie chart, or other visual representation can provide analyte data using shading, colors, patterns, icons, animation, or the like.

Figure 22:
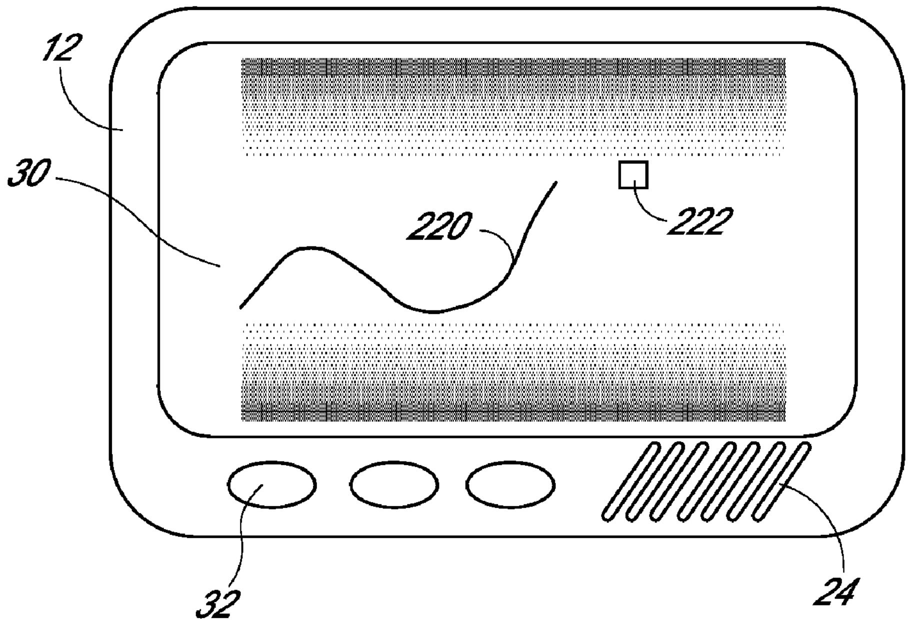
FIG. 22 is an illustration of the receiver in one embodiment showing an analyte trend graph, including measured analyte values and one or more clinically acceptable target analyte values.
Figure 23:
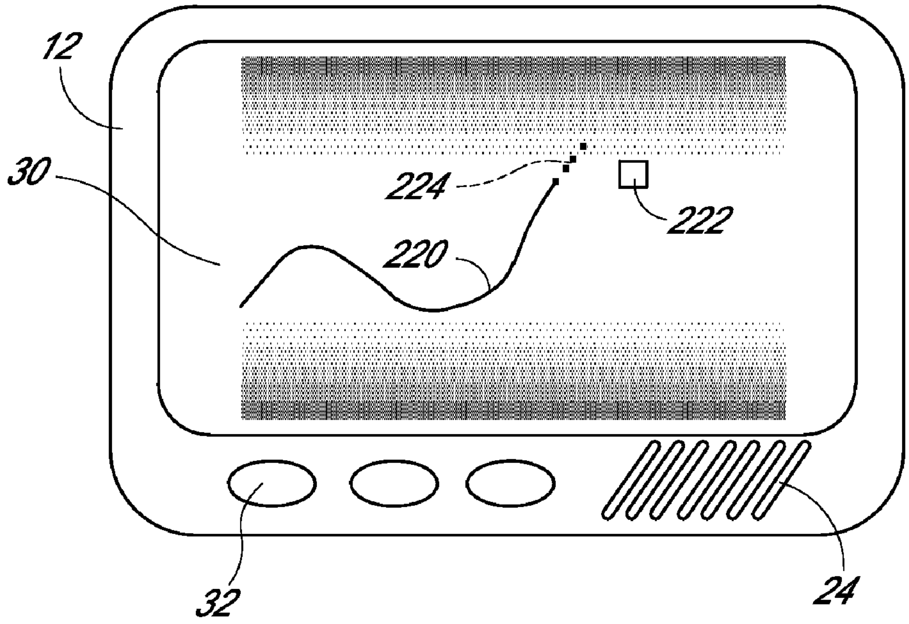
FIG. 23 is an illustration of the receiver of FIG. 22, further including estimated analyte values on the same screen.

FIG. 22 is an illustration of a receiver in one embodiment, which includes measured analyte values and a target analyte value(s). FIG. 23 is an illustration of the receiver of 22 further including estimated analyte values. FIG. 24 is an illustration of the receiver of 23 further including variations of estimated analyte values and including therapy recommendations to aid a user in obtaining the target analyte value.

FIG. 22 is an illustration of the receiver 12 in one embodiment, wherein the screen 30 shows measured analyte values 220 and one (or more) clinically acceptable target analyte values 222. The measured analyte values 220 are illustrated as a trend graph, such as described with reference to FIG. 20, however other representations are also possible.

Additionally, one or more clinically acceptable target analyte values 222 are provided as output, for example such as shown in FIG. 22. In some embodiments, the clinically acceptable target analyte values can be obtained from a variation analysis of clinical, physiological, or statistical variation, such as described in more detail elsewhere herein. Namely, the variation analysis provides the analyzed variation of the estimated analyte values, and the output module 18 (or processor 16) further analyzes the variation of estimated analyte values for those that are clinically acceptable and optionally also ensures physiological feasibility. For example, analysis of clinical risk can visually direct a patient to aim for an analyte value in a safe zone (for example, outside of the clinically risky zone).

In some embodiments, the output displays a point representing a target analyte value. In some embodiments, the output displays an object representing a general target analyte area. In some embodiments, the output displays a path of target analyte values. In some embodiments, the output displays a range of target analyte values along that path.

Humans are generally particularly responsive to targets, namely, able to understand the intention of targets and desire to obtain them. Advantageously, the output of target analyte values provides a goal towards which the user will aim. In the example shown on FIG. 20, the measured analyte values 220 indicate an upward trend of analyte concentration, and a user can likely visualize that the trend of the measured analyte values 220 will not likely hit the target 222 without intervention or action. Therefore, a user will be prompted to proactively care for his/her analyte concentration in an effort to hit the target analyte value(s) 222 (for example, administer insulin).

In some embodiments, the manufacturer, physician, patient, computer program, or the like can set the target analyte values. In some embodiments, a physician can set static target analyte values based on age, time of day, meal time, severity of medical condition, or the like; in such embodiments, the targets can be regularly or intermittently displayed in an effort to modify patient behavior through habitual reminders and training. Targets can be continually maintained on the screen or selectively displayed, for example when clinical risk is estimated, but can be avoided. In some embodiments, the target values can be dynamic targets, namely, targets that are dependent upon variable parameters such as age, time of day, meal time, severity of medical condition, medications received (for example, insulin injections) or the like, which can be input by a user or external device.

In one example of targets useful for a person with diabetes monitoring glucose concentration, the target glucose levels for a person with diabetes are typically between about 80 and about 130 mg/dL before meals and less than about 180 mg/dL one to two hours after a meal. In another exemplary embodiment, the amount and timing of insulin injections can be considered in determining the estimation of and target glucose ranges for a person with diabetes.

FIG. 23 is an illustration of the receiver 12 in another embodiment showing the measured analyte values 220 and clinically acceptable target analyte value(s) 222 of FIG. 22 and further showing estimated analyte values 224 on the same screen. In some embodiments, the data can be separated onto different screens that can be selectively viewed. However, viewing both estimated analyte values and the target analyte values can be useful in educating the patient regarding control of his/her analyte levels, since estimated and target analyte values are physiologically feasible in view of known physiological parameters described elsewhere herein. Estimated analyte values can be calculated and displayed in any manner described in the preferred embodiments.

FIG. 24 is an illustration of a receiver in another embodiment, including measured analyte values 220, target analyte values 222, estimated analyte values 224, such as described in more detail above with reference to FIGS. 22 and 23, and further including variations of estimated analyte values 226 and therapy recommendations 228 on the screen to help the user obtain the displayed target analyte values 222. The variations of estimated analyte values are calculated such as described in more detail with reference to FIG. 15.

The target analyte values presented should be physiologically feasible; therefore, type and/or amount of therapy can be determined (or estimated) to aid the patient in obtaining those therapy goals. In some embodiments, the therapy recommendations are representative icons, such as the injection icon 228 shown in FIG. 24. In alternative embodiments, icons can include an apple, orange juice, candy bar, or any icon representative of eating, drinking, or medicating, for example. In some embodiments, the therapy recommendations are preset alphanumeric messages (for example, "consume carbohydrates", "inject insulin", or "no therapy required"). In some embodiments therapy recommendations can be customized (for example, by a manufacturer, physician, patient, computer program, and/or the like) in order to provide more reliable, accurate, clinically safe, and/or individualized goals. For example, a physician can input information helpful in determining therapy recommendations using individual physiological considerations. As another example, data can be input via the user interface or via a wired or wireless connection to the receiver, such as age, time of day, meal time, severity of medical condition, medications received (for example, insulin injections) or the like, which can be used to determine the appropriate therapy recommendations.

In some embodiments, the therapy recommendations include a variety of scenarios, which the viewer can view and/or select. In these embodiments, the patient is given more control and able to make decisions based that fits best with their lifestyle or present circumstance, or considering external influences of which the system was unaware.

In some embodiments, therapy recommendations are sent to an external device (for example, insulin delivery mechanism), which is described in more detail with reference to FIGS. 27 to 30.

FIGS. 25 and 26 are views of the receiver showing an analyte trend graph, including measured analyte values and dynamic visual representation of range of estimated analyte values based on a variation analysis, such as described in more detail with reference to FIG. 15.

FIG. 25 is an illustration of a receiver 12 in another embodiment, including a screen 30 that shows the measured analyte values 230 and a variation of estimated analyte values 232 in one exemplary embodiment. In this embodiment, the visual representation of the variation of estimated analyte values 232 includes exemplary paths representative of the analyzed variation of estimated analyte values that illustrates a range of possible future analyte values. In some embodiments, the variation of estimated analyte values 232 is represented by a shape that begins at the most recently measured analyte value 234 and includes boundaries 236 that represent the range of possible variations of estimated analyte values for a future time period. The shape can be static or dynamic depending on the type of variation analyzed by the estimative algorithm, for example a fan, teardrop, or other shaped object.

FIG. 26 is an illustration of a receiver 12 in another embodiment, including a screen 30 that shows the measured analyte values 238 and a variation of estimated analyte values 240 in another exemplary embodiment. In this embodiment, the variation can include an estimated path and boundaries, for example, which can be obtained from a variation analysis and/or from physiological parameters, for example. In some alternative embodiments, color or other illustrative representation of levels of safety or danger can be provided on the screen.

Figure 27:
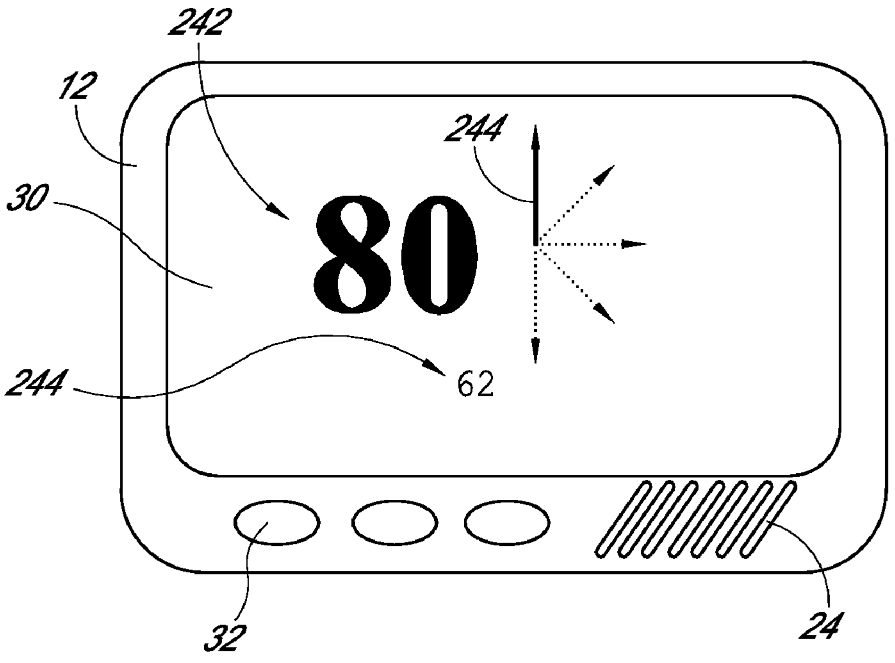
FIG. 27 is an illustration of the receiver in another embodiment, showing a numerical representation of the most recent measured analyte value, a directional arrow indicating rate of change, and a secondary numerical value representing a variation of the measured analyte value.

FIG. 27 is an illustration of a receiver 12 in another embodiment, including a screen 30 that shows a numerical representation of the most recent measured analyte value 242. This numerical value 242 is preferably a calibrated analyte value, such as described in more detail with reference to FIG. 2. Additionally, this embodiment preferably provides an arrow 244 on the screen 30, which represents the rate of change of the host's analyte concentration. A bold "up" arrow is shown on the drawing, which preferably represents a relatively quickly increasing rate of change. The arrows shown with dotted lines illustrate examples of other directional arrows (for example, rotated by 45 degrees), which can be useful on the screen to represent various other positive and negative rates of change. Although the directional arrows shown have a relative low resolution (45 degrees of accuracy), other arrows can be rotated with a high resolution of accuracy (for example one degree of accuracy) to more accurately represent the rate of change of the host's analyte concentration. In some alternative embodiments, the screen provides an indication of the acceleration of the host's analyte concentration.

A second numerical value 246 is shown, which is representative of a variation of the measured analyte value 242. The second numerical value is preferable determined from a variation analysis based on statistical, clinical, or physiological parameters, such as described in more detail elsewhere herein. In one embodiment, the second numerical value 246 is determined based on clinical risk (for example, weighted for the greatest possible clinical risk to a patient). In another embodiment, the second numerical representation 246 is an estimated analyte value extrapolated to compensate for a time lag, such as described in more detail elsewhere herein. In some alternative embodiments, the receiver displays a range of numerical analyte values that best represents the host's estimated analyte value (for example, +/−10%). In some embodiments, the range is weighted based on clinical risk to the patient. In some embodiments, the range is representative of a confidence in the estimated analyte value and/or a variation of those values. In some embodiments, the range is adjustable.

Patient Display

The potential of continuous glucose monitoring as an aid to both diabetic patients and their caregivers is well recognized. For the patient, continuous monitoring provides hour-to-hour glucose information that enables intensive therapy: it can be used to reduce the extent of hyperglycemic excursions without increasing the risk of hypoglycemic events. For caregivers of patients with diabetes, continuous monitoring provides day-to-day glucose information that can be used to optimize therapy. Despite these differences in purpose/perspective (hour-to-hour data for the patient, day-to-day information for the caregiver), the conventional display of continuous glucose data has heretofore not been adapted to the intended use/user. Accordingly, continuous glucose display methods that are utility-driven, and that allow the data to be easily perceived and interpreted is desirable.

Figure 28:
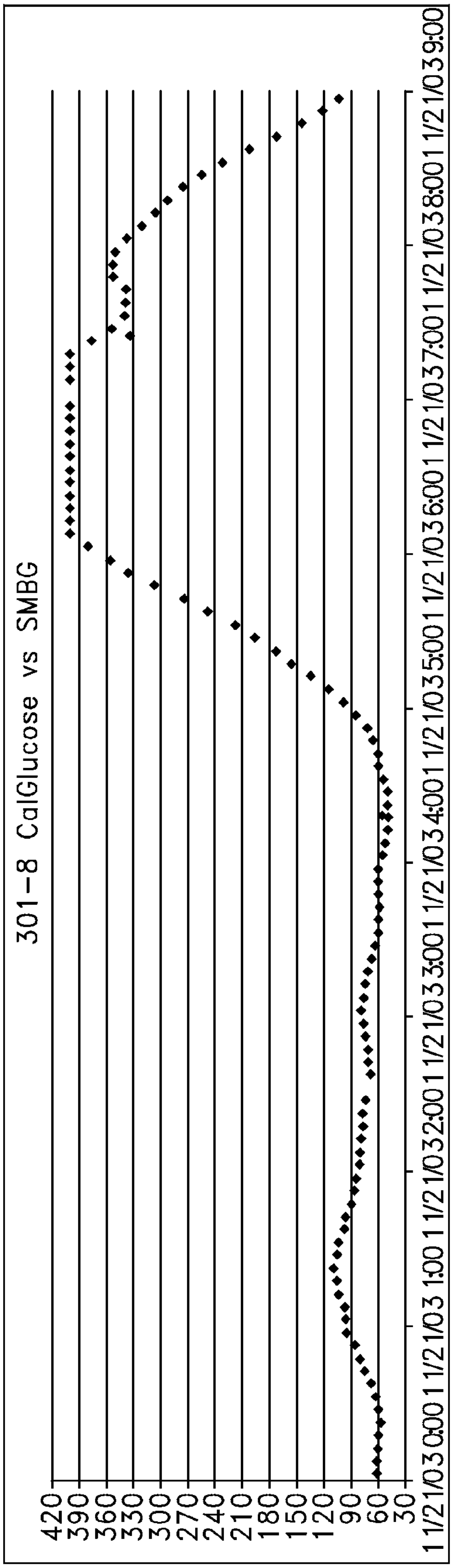
FIG. 28 depicts a conventional display of glucose data (uniform y-axis), 9-hour trend graph.
Figure 29:
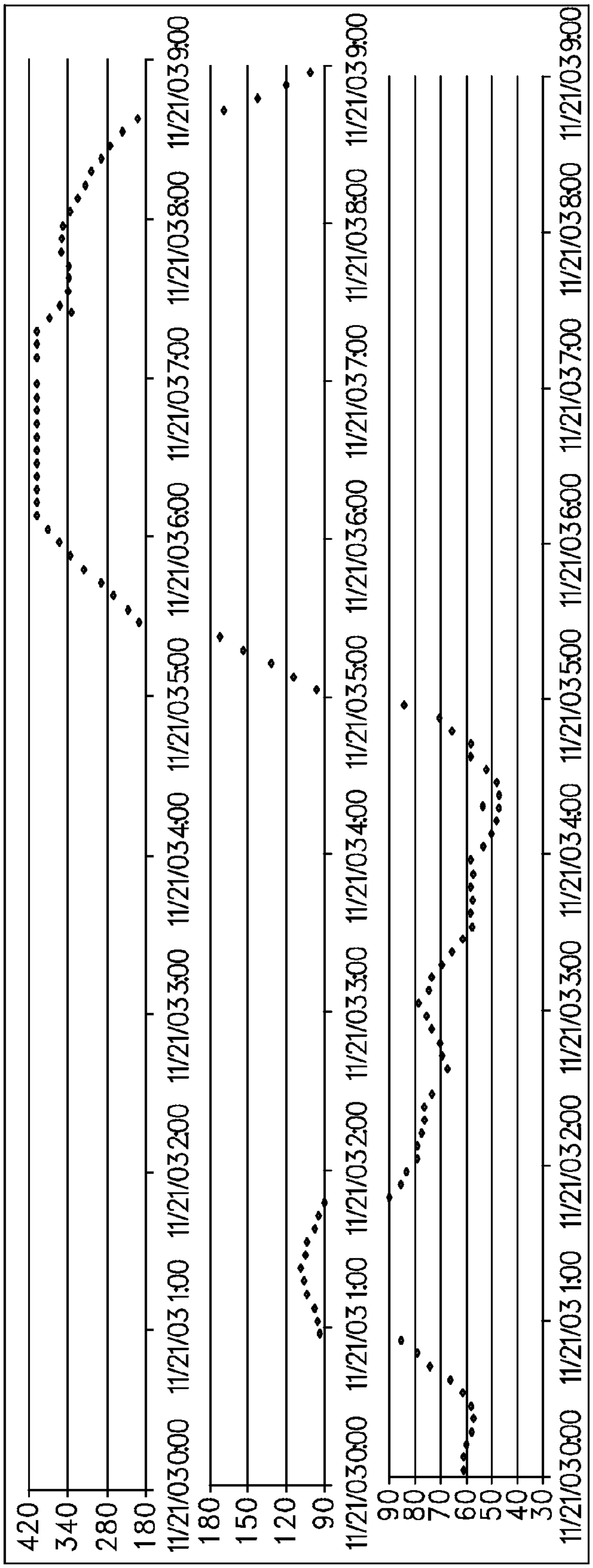
FIG. 29 depicts a utility-driven display of glucose data (non-uniform y-axis), 9-hour trend graph.

Glucose data are typically displayed on a graph with y-axis that spans a physiologic range of glucose (e.g. 40-400 mg/dl) and is uniform, i.e. the distance on the graph between 60 and 80 mg/dl is the same as the distance between 160 and 180 mg/dl, even though the clinical meanings of these two differences are significantly different. An alternative display uses a non-uniform y-axis that makes differences at low glucose levels easier to perceive. The difference in appearance of these two graphs is depicted in FIG. 28, which illustrates the conventional display of a 9-hour trend graph; FIG. 29 illustrates a display with a y-axis that has been equally divided into three zones (low, medium, and high glucose) though the glucose range (max-min) of each zone is different (40-90 mg/dl, 90-180 mg/dl, 180-400 mg/dl). The non-uniform y-axis in FIG. 29 appears to cause distortion to the glucose trend but does not appear to be misleading. More importantly, the dynamics at low glucose are more easily perceived in FIG. 29 than in FIG. 28.

Figure 30:
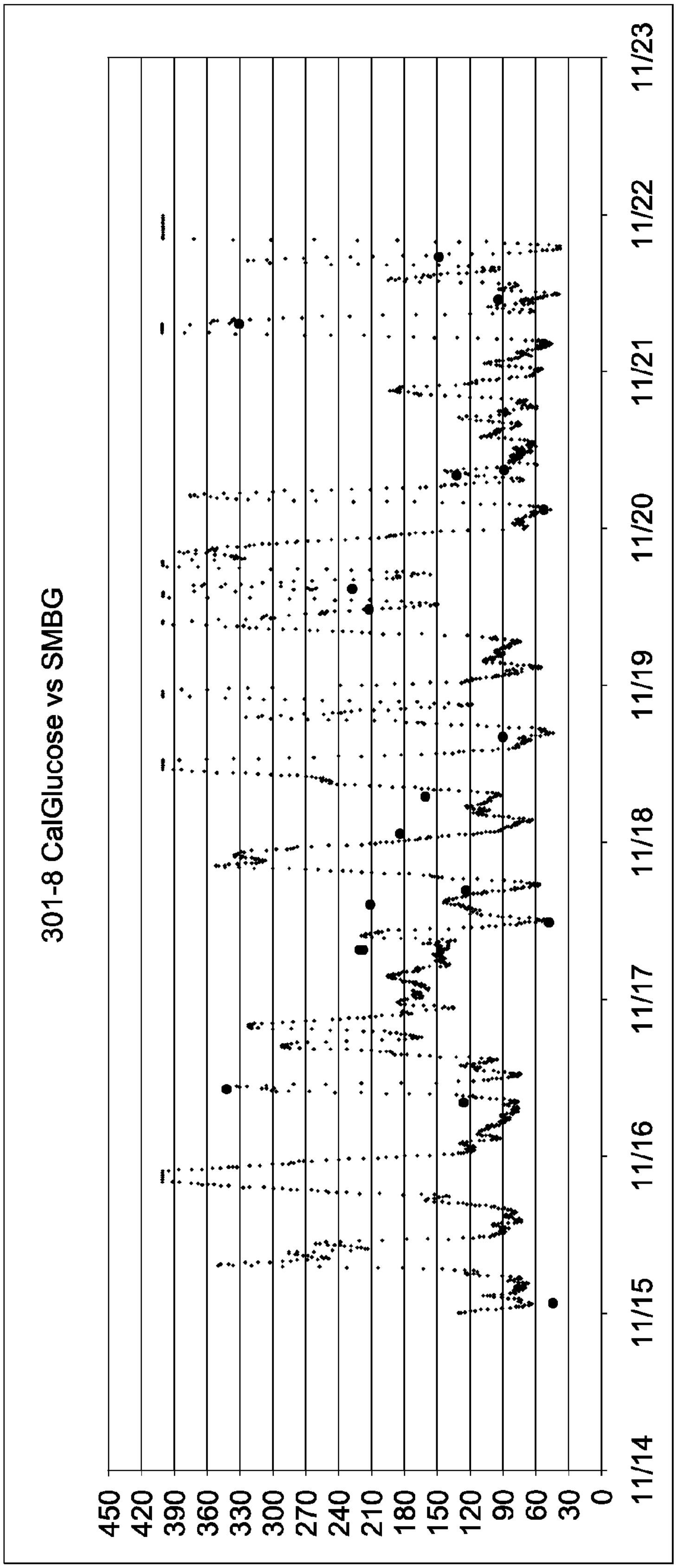
FIG. 30 depicts a conventional display of glucose data, 7-day glucose chart.
Figure 31:
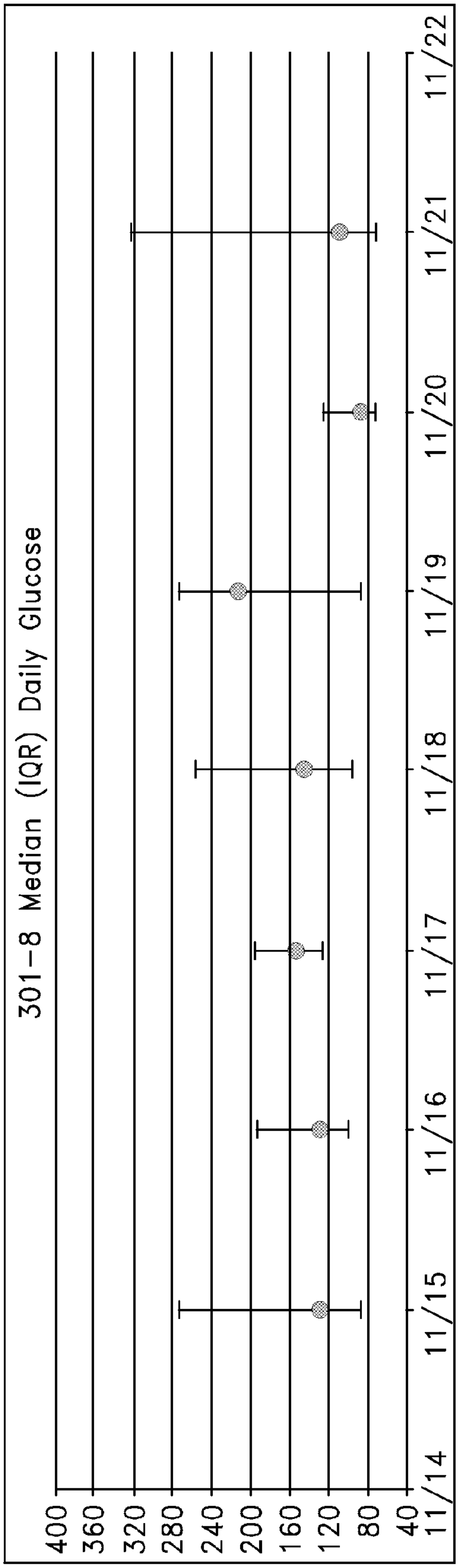
FIG. 31 depicts a utility-driven display of glucose data, 7-day control chart, median (interquartile range) of daily glucose.

Physicians use continuous glucose monitoring primarily for therapy optimization. Though the hour-to-hour dynamics of glucose can contain information related to therapy adjustment, a longer-term/summary perspective is perhaps easier perceive and interpret, and more reflective of changes in a patient's glycemic control. In this way, physician monitoring of a patient's glycemic control is similar to process monitoring used in quality control of manufactured products: the aim of both is to rapidly detect when the system/process is in or out of control, or to detect trends that can indicate changes in control. Control charts, which plot averages and ranges of process parameters over time, are a well-established and powerful illustration of process control and can be applicable to continuous glucose monitoring. FIGS. 30 and 31 illustrate the difference in how well the data reflect changes in glycemic control. FIG. 30 is a conventional plot of glucose over one week; FIG. 31 is a plot of the 24-hour (12 AM-12 AM) median (+/−interquartile range) glucose.

The display provides improved utility of continuous glucose data, enabling improved clinical outcomes, and offers advantages over prior art displays wherein the display of continuous glucose data is not tailored to the intended use.

Figure 32:
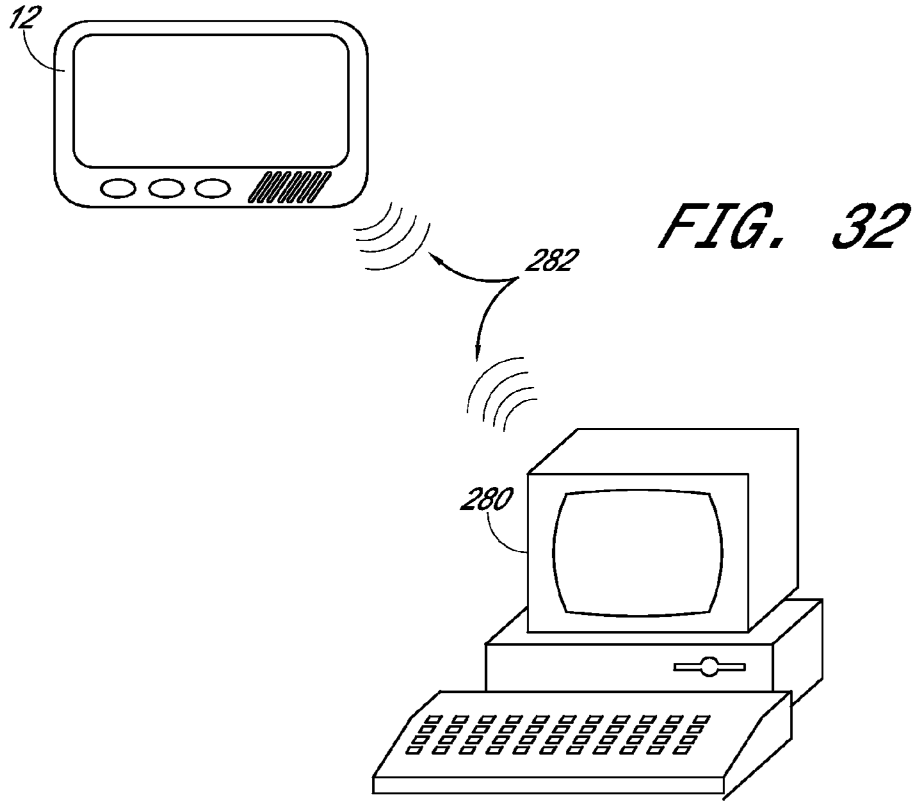
FIG. 32 is an illustration of a receiver in one embodiment that interfaces with a computer.

FIG. 32 is an illustration of a receiver that interfaces with a computer. A receiver 12 is provided that is capable of communication with a computer 280. The communication can include one-way or two-way wired or wireless transmissions 282. The computer 280 can be any system that processes information, such as a PC, server, personal digital assistant (PDA), or the like.

In some embodiments, the receiver sends information to the computer, for example, measured analyte data, estimated analyte data, target analyte data, therapy recommendations, or the like. The computer can include software that processes the data in any manner known in the art.

In some embodiments, the computer sends information to the receiver; for example, updating software, customizing the receiver programming (for example, setting individualized parameters), providing real time information (for example, mealtime and exercise that has been entered into a PDA), or the like.

Figure 33:
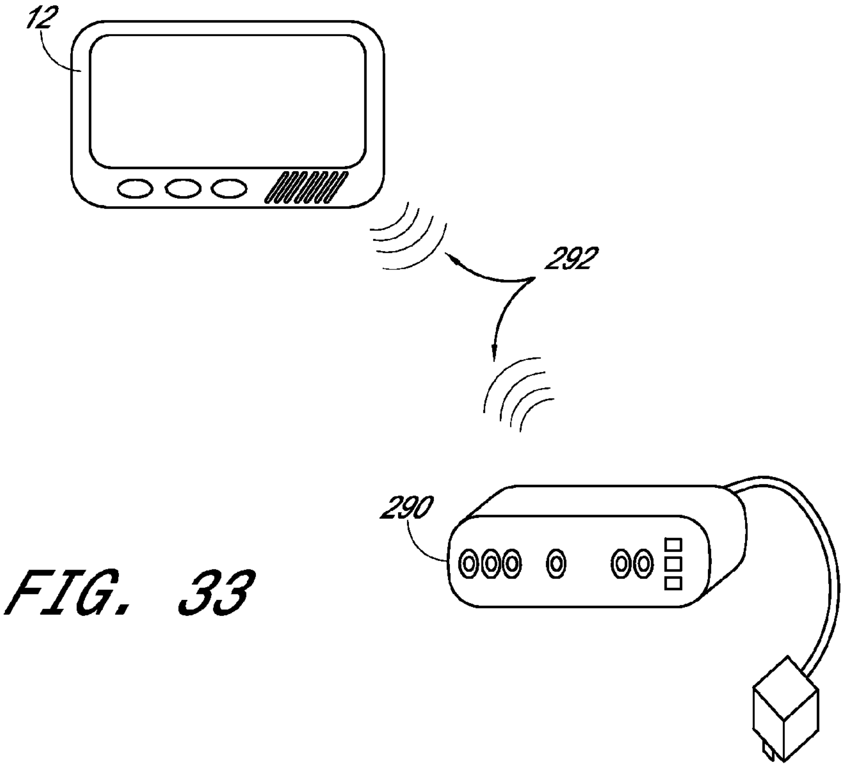
FIG. 33 is an illustration of a receiver in one embodiment that interfaces with a modem.

FIG. 33 is an illustration of a receiver 12 that interfaces with a modem 290, wherein data is transmitted via wireless transmissions 292 between the receiver and a modem in order to interface with a telecommunications line (for example, phone, pager, internet, network, etc). By providing an interface with a telecommunications line, the receiver can send and receive information from parties remote from the receiver, such as at a hospital, doctor's office, caretaker's computer, nationally-based server, or the like.

In some embodiments, the modem allows the receiver to send emergency messages to an emergency contact, such as a family member, hospital, Public Safety Answering Point (PSAP), or the like when analyte concentration are in a zone of extreme clinical risk. In some embodiments, a patient's doctor monitors his/her analyte concentration remotely and is able to request an appointment when certain conditions are not being met with the patient's analyte concentration. Numerous other uses can be contrived for communicating information via a modem 290 between the receiver 12 and another party, all of which are encompassed in the preferred embodiments.

Figure 34:
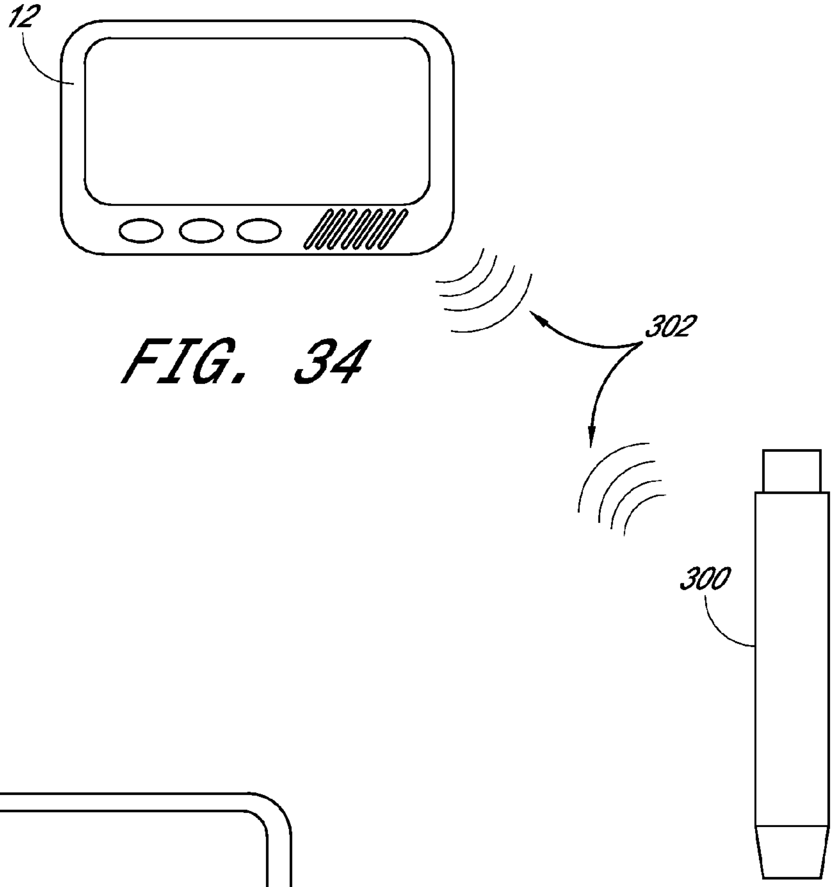
FIG. 34 is an illustration of a receiver in one embodiment that interfaces with an insulin pen.

FIG. 34 is an illustration of a receiver 12 that interfaces with an insulin pen 300, wherein data is transmitted via wireless transmission 302 between the receiver and the insulin pen 300. In some embodiments, the receiver sends therapy recommendations to the insulin pen, such as amount and time of insulin injection. In some embodiments, the insulin pen sends amount of therapy administered by a patient, such as type, amount, and time of administration. Such information can be used in data analysis, including estimation of analyte values, output of therapy recommendations, and trend analysis, for example.

Figure 35:
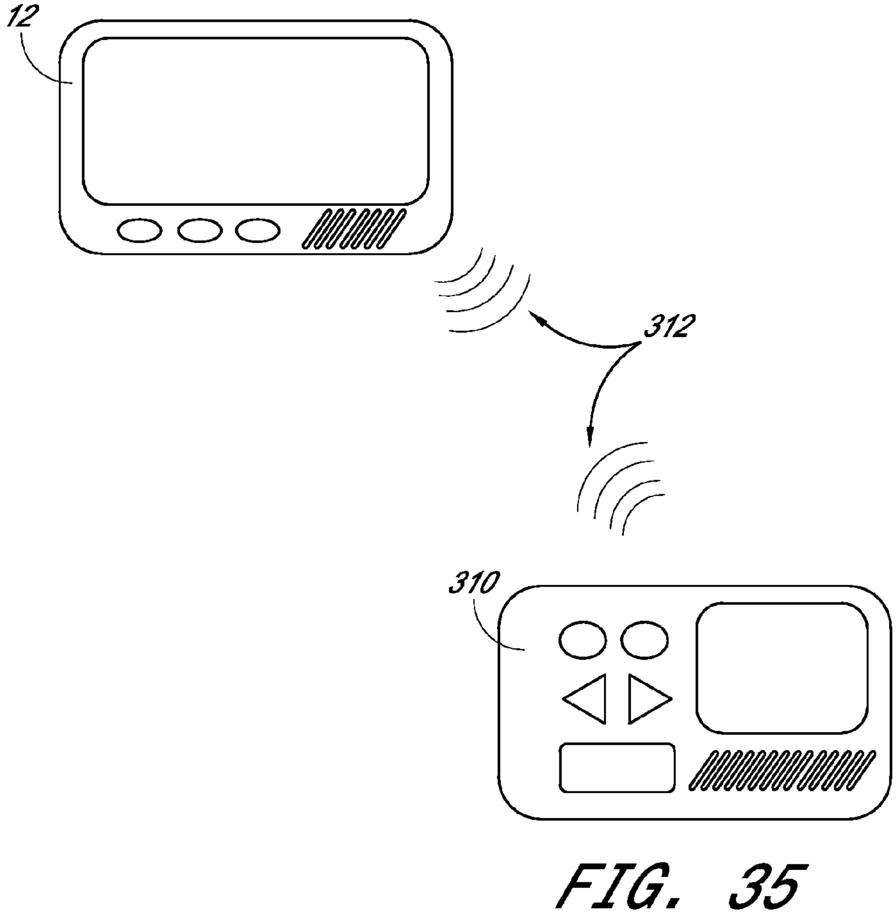
FIG. 35 is an illustration of a receiver in one embodiment that interfaces with an insulin pump.

FIG. 35 is an illustration of a receiver 12 that interfaces with an insulin pump 310, wherein data is transmitted via wireless transmission 312 between the receiver 12 and the insulin pump 310. In some embodiments, the receiver sends therapy recommendations to the insulin pump 310, such as amount and time of insulin administration. In some embodiments, the insulin pump 310 sends information regarding therapy to be administered such as type, amount, and time of administration. Such information can be used in data analysis, including estimation of analyte values, output of therapy recommendations, and trend analysis, for example.

In general, any of the above methods of data input and output can be combined, modified, selectively viewed, selectively applied, or otherwise altered without departing from the scope of the present invention.

Methods and devices that can be suitable for use in conjunction with aspects of the preferred embodiments are disclosed in copending applications including U.S. application Ser. No. 10/695,636 filed Oct. 28, 2003 and entitled, "SILICONE COMPOSITION FOR BIOCOMPATIBLE MEMBRANE"; U.S. application Ser. No. 10/632,537 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE." All of the above patents and patent applications are incorporated in their entirety herein by reference.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. All patents, applications, and other references cited herein are hereby incorporated by reference in their entirety.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

What is claimed is:

1. A glucose sensor system for monitoring glucose concentration in a biological sample of a host, the system comprising:

a continuous glucose sensor configured to produce sensor data indicative of a host's glucose concentration; and an electronics module configured to receive sensor data from the continuous glucose sensor, wherein the electronics module comprises a processor configured to process sensor data received from the continuous glucose sensor, to calibrate the sensor data, and to determine a rate of change of the host's glucose concentration based on the calibrated sensor data; and a display;

wherein the system is configured to present, on the display, a rate-of-change icon in at least three different configurations, and wherein the system is configured to select a configuration in which to present the icon on the display from the at least three different configurations based on the determined rate of change in the host's glucose concentration.

2. The glucose sensor system of claim 1, wherein the system is further configured to allow a user to toggle between presenting a first display comprising calibrated sensor data and a second display comprising at least one glucose concentration measurement by the reference glucose monitor.

3. The glucose sensor system of claim 1, wherein the system is further configured to allow a user to simultaneously present, on the display, calibrated sensor data and at least one glucose concentration measurement by the reference glucose monitor.

4. The glucose sensor system of claim 1, wherein the system is configured to select and display the icon in a first configuration when the determined rate of change is a first level, select and display the icon in a second configuration when the determined rate of change is a second level that is different than the first level, and select and display the icon in a third configuration when the determined rate of change is a third level that is different from the first level and the second level.

5. The glucose sensor system of claim 4, wherein each of the at least three different configurations of the icon comprises a directional arrow pointing in a different direction.

6. The glucose sensor system of claim 1, wherein the icon comprises a directional arrow symbol.

7. The glucose sensor system of claim 1, wherein the system is configured to select and present on the display a first configuration of the icon comprising a directional arrow symbol pointing in an upward direction when the determined rate of change is increasing at a first level, wherein the system is configured to select and present on the display a second configuration of the icon comprising a directional arrow symbol pointing in an upward direction when the determined rate of change is increasing at a second level that greater than the first level, wherein the system is configured to select and present on the display a third configuration of the icon comprising a directional arrow symbol pointing in a downward direction when the determined rate of change is decreasing at a third level, wherein the system is configured to select and present on the display a fourth configuration of the icon comprising a directional arrow symbol pointing in a downward direction when the determined rate of change is decreasing at a fourth level that is greater than the third level, and wherein each of the first, second, third and fourth configurations are different.

8. The glucose sensor system of claim 1, wherein the electronics module is further configured receive reference data from a reference glucose monitor operatively linked to the electronics module and to calibrate the sensor data using at least one glucose concentration measurement from the reference glucose monitor.

9. A system for processing continuous glucose sensor data, the system comprising:

a receiver configured for receiving sensor data from a continuous glucose sensor;

a processor;

a display; and a computer readable memory comprising instructions configured to cause the processor to determine a rate of change of glucose concentration based on the sensor data and to present, on the display, a first directional arrow pointing in an upward direction when the determined rate of change is increasing at a first level, a second directional arrow pointing in an upward direction when the determined rate of change is increasing at a second level that is greater than the first level, a third directional arrow symbol pointing in a downward direction when the determined rate of change is decreasing at a third level, and a fourth directional arrow pointing in a downward direction when the determined rate of change is decreasing at a fourth level that is greater than the third level, wherein each of the first, second, third and fourth directional arrows are displayed at different positions on the display.

10. The system of claim 9, wherein each of the first, second, third and fourth directional arrows are presented on the display rotated from one another in a range of 1 degree to 45 degrees.

11. The system of claim 9, wherein the system is configured to allow a user to toggle between presenting a first display comprising calibrated sensor data and a second display comprising at least one glucose concentration measurement by the reference glucose monitor.

12. The system of claim 9, wherein the system is configured to simultaneously display calibrated sensor data and at least one glucose concentration measurement by the reference glucose monitor.

13. The system of claim 9, further comprising a hand-held device, and wherein the receiver, the processor, the computer readable memory, and the display are incorporated in the hand-held device.

14. The system of claim 9, further comprising a reference glucose monitor, wherein the computer readable memory further comprises instructions configured to cause the processor to the calibrate the sensor data using at least one glucose concentration measurement by the reference glucose monitor, and wherein the rate of change is determined based on the calibrated sensor data.

15. The system of claim 9, wherein the first directional arrow points in an upward direction at an angle in a range between 1 to 45 degrees from the upward direction in which the second directional arrow points and wherein the third directional arrow points in a downward direction at an angle in a range between 1 to 45 degrees from the downward direction in which the third directional arrow points.

16. A method for processing sensor data, the method comprising:

receiving, with an electronic device, sensor data from a continuous glucose sensor;

determining a change in glucose concentration based on the sensor data; and displaying, on a display, a directional arrow at a first position on the display when the determined change in glucose concentration is a first level, a directional arrow at a second position on the display when the determined change in glucose concentration is a second level, a directional arrow at a third position on the display when the determined change in glucose concentration is a third level, and a directional arrow at a fourth position on the display when the determined change in glucose concentration is a fourth level, wherein each of the first, second, third and fourth positions are different and wherein each of the first, second, third and fourth levels are different.

17. The method of claim 16, wherein each of the first, second, third and fourth positions is a position rotated in a range of 1 degree to 45 degrees from at least one of the other positions.

18. The method of claim 16, further comprising simultaneously displaying at least one glucose concentration measurement by the reference glucose monitor, a calibrated sensor data with a glucose concentration target range, and one of the first, second, third or fourth directional arrow.

19. The method of claim 16, wherein the determined change is a rate of change.

20. The method of claim 19, wherein the first level is a first increasing rate of change the second level is a second increasing rate of change that is greater than the first increasing rate of change, the third level is a first decreasing rate of change and the fourth level is a decreasing rate of change that is greater than the first decreasing rate of change.

21. A glucose sensor system for monitoring glucose concentration in a biological sample of a host, the system comprising:

a continuous glucose sensor configured to produce sensor data indicative of a host's glucose concentration, wherein the continuous glucose sensor comprises a sensing region and a sensing membrane located over the sensing region, and wherein at least a portion of the continuous glucose sensor is configured for transcutaneous implantation; and an electronics module configured to receive sensor data from the continuous glucose sensor, the electronics module comprising a processor module and computer readable memory having instructions configured to cause the processor module to:

process sensor data received from the continuous glucose sensor, calibrate sensor data using at least one glucose concentration measurement from a reference glucose monitor operatively linked to the electronics module, determine a rate of change of glucose concentration using the calibrated sensor data, and display a directional arrow in at least one of three different positions on a display depending upon the determined rate of change.

22. The glucose sensor system of claim 21, additionally comprising instructions configured to cause the processor module to toggle between a display output comprising calibrated sensor data and a display output comprising at least one glucose concentration measurement by the reference glucose monitor.

23. The system of claim 21, wherein the at least three different positions comprise a plurality of different positions associated with increasing rates of change and a plurality of different positions associated with decreasing rates of change.

24. The system of claim 21, wherein the at least three different positions comprise a first position in which the directional arrow is pointing in a horizontal direction, a second position in which the directional arrow is pointing in an upward vertical direction and a third position in which the directional arrow is pointing in a downward vertical direction.

* * * * *

UNITED STATES PATENT AND TRADEMARK OFFICE

CERTIFICATE OF CORRECTION

PATENT NO. : 8,257,259 B2
APPLICATION NO. : 12/252952
DATED : September 4, 2012
INVENTOR(S) : Brauker et al.

It is certified that error appears in the above-identified patent and that said Letters Patent is hereby corrected as shown below:

| Issued Patent Column | Line | Description of Discrepancy |
|---|---|---|
| (Item 56) Page 7 Col. 1 | 4 | Under Other Publications, change “Filder” to --Filter--. |
| (Item 56) Page 7 Col. 1 | 36 | Under Other Publications, change “Senso” to --Sensor--. |
| (Item 56) Page 7 Col. 1 | 43 | Under Other Publications, change “basedon” to --based on--. |
| (Item 56) Page 7 Col. 2 | 40 | Under Other Publications, change “Membran,” to --Membrane,--. |
| (Item 56) Page 8 Col. 1 | 38 | Under Other Publications, change “hypoglycaemic” to --hypoglycemic--. |
| (Item 56) Page 8 Col. 1 | 51 | Under Other Publications, change “patents” to --patients--. |
| (Item 56) Page 9 Col. 1 | 6 | Under Other Publications, change ““xenogenic.”” to --“xenogeneic.”--. |
| (Item 56) Page 9 Col. 1 | 8 | Under Other Publications, change “xenogenic.” to --xenogeneic.--. |
| (Item 56) Page 9 Col. 1 | 34 | Under Other Publications, change “Thechnol.” to --Technol.--. |

Signed and Sealed this
Nineteenth Day of February, 2013

Teresa Stanek Rea
*Acting Director of the United States Patent and Trademark Office*

| | | |
|---|---|---|
| (Item 56) Page 9 Col. 2 | 37 | Under Other Publications, change "impintable," to --imprintable,--. |
| (Item 56) Page 9 Col. 2 | 42 | Under Other Publications, change "reliablity" to --reliability--. |
| (Item 56) Page 9 Col. 2 | 53 | Under Other Publications, change "Enzymlology," to --Enzymology,--. |
| (Item 56) Page 9 Col. 2 | 61 | Under Other Publications, change "systme" to --system--. |
| (Item 56) Page 9 Col. 2 | 66 | Under Other Publications, change "artifical" to --artificial--. |
| (Item 56) Page 10 Col. 1 | 12 | Under Other Publications, change "your and your" to --you and your--. |
| (Item 56) Page 10 Col. 1 | 25 | Under Other Publications, change "dynamcs" to --dynamics--. |
| (Item 56) Page 10 Col. 1 | 28 | Under Other Publications, change "glocuse" to --glucose--. |
| (Item 56) Page 10 Col. 1 | 29 | Under Other Publications, change "Diabetese" to --Diabetes--. |
| (Item 56) Page 10 Col. 1 | 42 | Under Other Publications, change "Hypoglycaemia" to --Hypoglycemia--. |
| (Item 56) Page 10 Col. 1 | 55 | Under Other Publications, change "Thechnol." to --Technol.--. |
| (Item 56) Page 10 Col. 1 | 60 | Under Other Publications, change "Diabetese" to --Diabetes--. |
| (Item 56) Page 10 Col. 2 | 10 | Under Other Publications, change "inactiviation" to --inactivation--. |
| (Item 56) Page 10 Col. 2 | 65 | Under Other Publications, change "Aniodic" to --Anodic--. |
| (Item 56) Page 11 Col. 1 | 51 | Under Other Publications, change "activitiy," to --activity,--. |

| | | |
|---|---|---|
| (Item 56) Page 11 Col. 1 | 68 | Under Other Publications, change "Beioelectronics," to --Bioelectronics,--. |
| (Item 56) Page 11 Col. 1 | 69 | Under Other Publications, change "glocuse" to --glucose--. |
| (Item 56) Page 11 Col. 2 | 8 | Under Other Publications, change "valication" to --validation--. |
| (Item 56) Page 11 Col. 2 | 9 | Under Other Publications, change "iunsulin interaaction in tyhpe" to --insulin interaction in type--. |
| (Item 56) Page 11 Col. 2 | 24 | Under Other Publications, change "Electronanalysis" to --Electroanalysis--. |
| (Item 56) Page 11 Col. 2 | 47 | Under Other Publications, change "artifical" to --artificial--. |
| (Item 56) Page 11 Col. 2 | 59 | Under Other Publications, change "amperometeric" to --amperometric--. |
| (Item 56) Page 11 Col. 2 | 66 | Under Other Publications, change "Thechnol." to --Technol.--. |
| (Item 56) Page 12 Col. 1 | 36 | Under Other Publications, change "termistor" to --thermistor--. |
| (Item 56) Page 12 Col. 1 | 37 | Under Other Publications, change "metobolites," to --metabolites,--. |
| (Item 56) Page 12 Col. 1 | 39 | Under Other Publications, change "cholesteral and cholesteral" to --cholesterol and cholesterol--. |
| (Item 56) Page 12 Col. 1 | 43 | Under Other Publications, change "Apllied" to --Applied--. |
| (Item 56) Page 12 Col. 2 | 46 | Under Other Publications, change "Subcutaenous" to --Subcutaneous--. |
| (Item 56) Page 12 Col. 2 | 59 | Under Other Publications, change "assitance" to --assistance--. |
| (Item 56) Page 12 Col. 2 | 60 | Under Other Publications, change "Thechnol." to --Technol.--. |

| | | |
|---|---|---|
| (Item 56) Page 13 Col. 1 | 24 | Under Other Publications, change “pancrease” to --pancreas--. |
| (Item 56) Page 13 Col. 1 | 34 | Under Other Publications, change “Thechnol.” to --Technol.--. |
| (Item 56) Page 13 Col. 1 | 62 | Under Other Publications, change “Membrance” to --Membranes--. |
| (Item 56) Page 13 Col. 1 | 70 | Under Other Publications, change “cholesteral” to --cholesterol--. |
| (Item 56) Page 13 Col. 2 | 23 | Under Other Publications, change “Deabetes” to --Diabetes--. |
| (Item 56) Page 13 Col. 2 | 45 | Under Other Publications, change “Tranducers” to --Transducers--. |
| (Item 56) Page 14 Col. 2 | 1 | Under Other Publications, change “Immoblized” to --Immobilized--. |
| (Item 56) Page 14 Col. 2 | 20 | Under Other Publications, change “continous” to --continuous--. |
| (Item 56) Page 14 Col. 2 | 23 | Under Other Publications, change “Decarbozylase” to --Decarboxylase--. |
| (Item 56) Page 15 Col. 1 | 33 | Under Other Publications, change “Respons(es)” to --Response(s)--. |
| Sheet 7 of 29 (Y-axis) FIG. 7 | 6 | Change “5500” to --50--. |
| Sheet 13 of 29 (Reference Numeral 130) FIG. 13 | 3 | Change “EXALUATION” to --EVALUATION--. |
| Sheet 17 of 29 (Y-axis) FIG. 17 | 1 | Change “40” to --400--. |
| 12 | 22-23 | Change “andrenostenedione;” to --androstenedione;--. |
| 12 | 38 | Change “diptheria/” to --diphtheria/--. |
| 12 | 45 | Change “perioxidase;” to --peroxidase;--. |
| 12 | 58 | Change “duodenalisa,” to --duodenalis,--. |

| | | |
|---|---|---|
| 12 | 66 | Change “Trepenoma pallidium,” to --Treponema pallidum,--. |
| 12 | 67 | Change “stomatis” to --stomatitis--. |
| 13 | 20 | Change “(barbituates,” to --(barbiturates,--. |
| 20 | 50 | Change “”filed” to --” filed--. |
| 36 | 6-7 | Change “and or” to --and/or--. |
| 53 | 14 (Approx.) | In claim 7, change “that greater” to --that is greater--. |
| 53 | 28 (Approx.) | In claim 8, change “configured receive” to --configured to receive--. |
| 54 | 13 (Approx.) | In claim 14, change “to the calibrate” to --to calibrate--. |